US011052175B2

(12) United States Patent
Nasert et al.

(10) Patent No.: US 11,052,175 B2
(45) Date of Patent: Jul. 6, 2021

(54) CARTILAGE-DERIVED IMPLANTS AND METHODS OF MAKING AND USING SAME

(71) Applicant: MUSCULOSKELETAL TRANSPLANT FOUNDATION, Edison, NJ (US)

(72) Inventors: Michael A. Nasert, Hazlet, NJ (US); Florence Stoffel, Whitehouse Station, NJ (US); Paul R. Williams, Boise, ID (US); Alex Callahan, Eatontown, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 0 days.

(21) Appl. No.: 15/236,975

(22) Filed: Aug. 15, 2016

(65) Prior Publication Data

US 2017/0049930 A1 Feb. 23, 2017

Related U.S. Application Data

(60) Provisional application No. 62/207,146, filed on Aug. 19, 2015.

(51) Int. Cl.
*A61L 27/36* (2006.01)
*B29C 65/56* (2006.01)
*B29B 13/04* (2006.01)
*B29L 31/00* (2006.01)

(52) U.S. Cl.
CPC ....... *A61L 27/3612* (2013.01); *A61L 27/3654* (2013.01); *B29B 13/04* (2013.01); *B29C 65/565* (2013.01); *A61L 2430/06* (2013.01); *B29K 2995/0056* (2013.01); *B29L 2031/7532* (2013.01)

(58) Field of Classification Search
None
See application file for complete search history.

(56) References Cited

U.S. PATENT DOCUMENTS

| 831,812 | A | 9/1906 | Weber |
| 4,707,369 | A | 11/1987 | Suresky |
| 4,767,746 | A | 8/1988 | Catsimpoolas |
| 4,776,853 | A | 10/1988 | Klement |
| 4,801,299 | A | 1/1989 | Brendel |

(Continued)

FOREIGN PATENT DOCUMENTS

| CA | 2563082 | 11/2005 |
| CA | 2717725 | 9/2009 |

(Continued)

OTHER PUBLICATIONS

Beaudoin et al., Journal of Otolaryngology—Head and Neck Surgery 42: 7 (2013).*

(Continued)

*Primary Examiner* — Erin M. Bowers
(74) *Attorney, Agent, or Firm* — Marcella M. Bodner; Cole Schotz, P.C.

(57) ABSTRACT

Cartilage fibers and implants made therefrom are disclosed, with and without cartilage particles. Methods for making the cartilage fibers and the implants containing them are also disclosed. The implants may be pre-shaped and may be reshapable and provide good shape retention and little swelling when placed into a cartilage defect.

12 Claims, 8 Drawing Sheets

(56) References Cited

U.S. PATENT DOCUMENTS

| | | |
|---|---|---|
| 4,820,626 A | 4/1989 | Williams |
| 5,035,708 A | 7/1991 | Alchas |
| 5,079,160 A | 1/1992 | Lacy |
| 5,131,907 A | 7/1992 | Williams |
| 5,196,185 A | 3/1993 | Silver et al. |
| 5,230,693 A | 7/1993 | Williams |
| 5,284,655 A | 2/1994 | Bogdansky et al. |
| 5,290,558 A | 3/1994 | O'Leary et al. |
| 5,298,254 A | 3/1994 | Prewett et al. |
| 5,326,357 A | 7/1994 | Kandel |
| 5,336,616 A | 8/1994 | Livesey |
| 5,436,135 A | 7/1995 | Tayot |
| 5,516,532 A | 5/1996 | Atala |
| 5,628,781 A | 5/1997 | Williams |
| 5,632,778 A | 5/1997 | Goldstein |
| 5,674,292 A | 10/1997 | Tucker et al. |
| 5,744,360 A | 4/1998 | Hu |
| 5,800,537 A | 9/1998 | Bell |
| 5,804,366 A | 9/1998 | Hu |
| 5,837,235 A | 11/1998 | Mueller |
| 5,843,182 A | 12/1998 | Goldstein |
| 5,855,619 A | 1/1999 | Caplan |
| 5,869,037 A | 2/1999 | Crystal |
| 5,888,220 A | 3/1999 | Felt et al. |
| 5,893,888 A | 4/1999 | Bell |
| 5,899,936 A | 5/1999 | Goldstein |
| 5,899,939 A | 5/1999 | Boyce et al. |
| 5,964,805 A | 10/1999 | Stone |
| 5,968,556 A | 10/1999 | Atala et al. |
| 5,993,844 A | 11/1999 | Abraham |
| 6,020,196 A | 2/2000 | Hu |
| 6,099,567 A | 8/2000 | Badylak |
| 6,123,731 A | 9/2000 | Boyce et al. |
| 6,127,143 A | 10/2000 | Gunasekaran |
| 6,149,906 A | 11/2000 | Mosca |
| 6,277,555 B1 | 8/2001 | Duran |
| 6,284,284 B1 | 9/2001 | Naughton |
| 6,316,247 B1 | 11/2001 | Katz |
| 6,326,029 B1 | 12/2001 | Geistlich |
| 6,348,069 B1 | 2/2002 | Vacanti |
| 6,355,239 B1 | 3/2002 | Bruder |
| 6,371,992 B1 | 4/2002 | Tanagho |
| 6,387,693 B2 | 5/2002 | Reiser |
| 6,391,297 B1 | 5/2002 | Halvorsen |
| 6,398,819 B1 | 6/2002 | Bell |
| 6,429,013 B1 | 8/2002 | Halvorsen |
| 6,436,138 B1 | 8/2002 | Dowd et al. |
| 6,440,444 B2 | 8/2002 | Boyce et al. |
| 6,451,060 B2 | 9/2002 | Masuda et al. |
| 6,461,630 B1 | 10/2002 | Tucker et al. |
| 6,468,314 B2 | 10/2002 | Schwartz et al. |
| 6,504,079 B2 | 1/2003 | Tucker et al. |
| 6,576,015 B2 | 1/2003 | Geistlich et al. |
| 6,511,958 B1 | 2/2003 | Atkinson et al. |
| 6,596,274 B1 | 7/2003 | Abatangelo |
| 6,652,872 B2 | 11/2003 | Nevo |
| 6,662,805 B2 | 12/2003 | Frondoza et al. |
| 6,676,969 B2 | 1/2004 | Geistlich et al. |
| 6,696,073 B2 | 2/2004 | Boyce et al. |
| 6,696,074 B2 | 2/2004 | Dai |
| 6,734,018 B2 | 5/2004 | Wolfinbarger |
| 6,764,517 B2 | 7/2004 | Yamamoto et al. |
| 6,777,231 B1 | 8/2004 | Katz |
| 6,841,150 B2 | 1/2005 | Halvorsen |
| 6,849,594 B1 | 2/2005 | Chen et al. |
| 6,866,686 B2 | 3/2005 | Ollerenshaw |
| 6,886,568 B2 | 5/2005 | Frondoza et al. |
| 6,893,653 B2 | 5/2005 | Abraham |
| 6,942,961 B1 | 9/2005 | Baumgartner |
| 6,991,652 B2 | 1/2006 | Burg |
| 7,001,430 B2 | 2/2006 | Mills |
| 7,004,977 B2 | 2/2006 | Ashman |
| 7,008,591 B2 | 3/2006 | Kafesjian |
| 7,019,192 B2 | 3/2006 | Gertzman et al. |
| 7,029,666 B2 | 4/2006 | Bruder |
| 7,029,689 B2 | 4/2006 | Berglund |
| 7,029,838 B2 | 4/2006 | Williams |
| 7,030,157 B2 | 4/2006 | HuaZhu |
| 7,033,587 B2 | 4/2006 | Halvorsen |
| 7,052,829 B2 | 5/2006 | Williams |
| 7,060,022 B2 | 6/2006 | Chen |
| 7,067,123 B2 | 6/2006 | Gomes |
| 7,078,230 B2 | 7/2006 | Wilkison |
| 7,078,232 B2 | 7/2006 | Konkle |
| 7,131,994 B2 | 11/2006 | Mills |
| 7,153,518 B2 | 12/2006 | Wironen et al. |
| 7,186,557 B2 | 3/2007 | Marki |
| 7,201,917 B2 | 4/2007 | Malaviya |
| 7,208,177 B2 | 4/2007 | Geistlich |
| 7,252,685 B2 | 8/2007 | Bindsell |
| 7,294,509 B2 | 11/2007 | Darimont |
| 7,297,540 B2 | 11/2007 | Mitrani |
| 7,316,822 B2 | 1/2008 | Binette et al. |
| 7,323,190 B2 | 1/2008 | Chu |
| 7,335,381 B2 | 2/2008 | Malinin et al. |
| 7,338,757 B2 | 3/2008 | Wolfinbarger |
| 7,354,702 B2 | 4/2008 | Dai |
| 7,354,749 B2 | 4/2008 | Fisher |
| 7,390,484 B2 | 6/2008 | Fraser |
| 7,402,319 B2 | 7/2008 | Schmidt |
| 7,429,488 B2 | 9/2008 | Fraser |
| 7,445,793 B2 | 11/2008 | Niwa |
| 7,470,537 B2 | 12/2008 | Hedrick |
| 7,473,420 B2 | 1/2009 | Fraser |
| 7,476,257 B2 | 1/2009 | Sah |
| 7,488,348 B2 | 2/2009 | Truncale |
| 7,498,040 B2 | 3/2009 | Masinaei |
| 7,498,041 B2 | 3/2009 | Masinaei |
| 7,501,115 B2 | 3/2009 | Fraser |
| 7,514,075 B2 | 4/2009 | Hedrick |
| 7,520,888 B2 | 4/2009 | Trieu |
| 7,521,234 B2 | 4/2009 | Kobayashi et al. |
| 7,531,355 B2 | 5/2009 | Rodriguez |
| 7,550,152 B2 | 7/2009 | Pandit |
| 7,582,292 B2 | 9/2009 | Wilkison |
| 7,585,323 B2 | 9/2009 | Masini et al. |
| 7,585,670 B2 | 9/2009 | Hedrick |
| 7,592,174 B2 | 9/2009 | Sylvester |
| 7,595,043 B2 | 9/2009 | Hedrick |
| 7,595,062 B2 | 9/2009 | Pedrozo |
| 7,621,963 B2 | 11/2009 | Simon |
| 7,625,581 B2 | 12/2009 | Laredo |
| 7,648,676 B2 | 1/2010 | Mills |
| 7,651,684 B2 | 1/2010 | Hedrick |
| 7,682,822 B2 | 3/2010 | Noll |
| 7,687,059 B2 | 3/2010 | Fraser |
| RE41,286 E | 4/2010 | Atkinson et al. |
| 7,709,442 B2 | 5/2010 | Mao |
| 7,732,126 B2 | 6/2010 | Zhang |
| 7,763,081 B2 | 7/2010 | Ollerenshaw |
| 7,767,452 B2 | 8/2010 | Kleinsek |
| 7,771,716 B2 | 8/2010 | Hedrick |
| 7,775,965 B2 | 8/2010 | McFetridge |
| 7,776,596 B2 | 8/2010 | Badylak |
| 7,785,582 B2 | 8/2010 | Johnson |
| 7,795,022 B2 | 9/2010 | Badylak |
| 7,807,461 B2 | 10/2010 | Kang |
| 7,815,686 B2 | 10/2010 | Badylak |
| 7,815,926 B2 | 10/2010 | Syring |
| 7,824,609 B2 | 11/2010 | Konertz |
| 7,824,701 B2 | 11/2010 | Binette |
| 7,824,711 B2 | 11/2010 | Kizer et al. |
| 7,837,740 B2 | 11/2010 | Semler |
| 7,838,040 B2 | 11/2010 | Malinin |
| 7,846,728 B2 | 12/2010 | Brooks |
| 7,871,605 B2 | 1/2011 | Hampson |
| 7,875,296 B2 | 1/2011 | Binette |
| 7,883,541 B2 | 2/2011 | Mills |
| 7,887,795 B2 | 2/2011 | Fraser |
| 7,892,724 B2 | 2/2011 | Shimko |
| RE42,208 E | 3/2011 | Truncale |
| 7,901,457 B2 | 3/2011 | Truncale |
| 7,901,461 B2 | 3/2011 | Harmon |
| 7,901,672 B2 | 3/2011 | Fraser |

(56) References Cited

U.S. PATENT DOCUMENTS

| | | |
|---|---|---|
| 7,906,110 B2 | 3/2011 | Chancellor |
| 7,914,808 B2 | 3/2011 | Malaviya |
| 7,915,039 B2 | 3/2011 | Teplyashin |
| 7,931,687 B2 | 4/2011 | Masuda |
| 7,932,084 B2 | 4/2011 | Katz |
| 7,939,108 B2 | 5/2011 | Morris |
| 7,947,266 B2 | 5/2011 | Gronthos |
| 7,960,098 B2 | 6/2011 | Roy |
| 7,968,329 B2 | 6/2011 | Dancu |
| 7,977,094 B2 | 7/2011 | Masinaei |
| 7,993,679 B2 | 8/2011 | Ingram |
| 7,998,472 B2 | 8/2011 | Huss |
| 7,998,735 B2 | 8/2011 | Morrison |
| 8,017,389 B2 | 9/2011 | Phillips |
| 8,017,390 B2 | 9/2011 | Park |
| 8,021,869 B2 | 9/2011 | Chu |
| 8,025,896 B2 | 9/2011 | Malaviya |
| 8,067,149 B2 | 11/2011 | Livesey |
| 8,067,234 B2 | 11/2011 | March |
| 8,070,827 B2 | 12/2011 | Shortkroff |
| 8,071,083 B2 | 12/2011 | De Bruijn |
| 8,093,047 B2 | 1/2012 | Takakura |
| 8,105,580 B2 | 1/2012 | Fraser |
| 8,106,251 B2 | 1/2012 | Ayares |
| 8,114,668 B2 | 2/2012 | Stolen |
| 8,119,121 B2 | 2/2012 | Fraser |
| 8,119,398 B2 | 2/2012 | Sayre |
| RE43,258 E | 3/2012 | Truncale |
| 8,137,702 B2 | 3/2012 | Binette |
| 8,137,703 B2 | 3/2012 | Binette |
| 8,163,018 B2 | 4/2012 | Trieu |
| 8,163,276 B2 | 4/2012 | Hedrick |
| 8,163,495 B2 | 4/2012 | Buhring |
| 8,163,549 B2 | 4/2012 | Yao et al. |
| 8,187,619 B2 | 5/2012 | Johnson |
| 8,192,348 B2 | 6/2012 | Tranquillo |
| 8,192,763 B2 | 6/2012 | Johnson |
| 8,202,493 B2 | 6/2012 | Buss |
| 8,221,500 B2 | 7/2012 | Truncale |
| 8,226,715 B2 | 7/2012 | Hwang |
| 8,241,902 B2 | 8/2012 | Itskovitz-Eldor |
| 8,246,947 B2 | 8/2012 | Hedrick |
| 8,263,359 B2 | 9/2012 | Reschiglian |
| 8,273,253 B2 | 9/2012 | Curran |
| 8,292,799 B2 | 10/2012 | Xu |
| 8,292,968 B2 | 10/2012 | Truncale et al. |
| 8,308,814 B2 | 11/2012 | Sengun |
| 8,309,106 B2 | 11/2012 | Masinaei |
| 8,309,342 B2 | 11/2012 | Stubbers |
| 8,334,135 B2 | 12/2012 | Rodriguez |
| 8,337,711 B2 | 12/2012 | Dorian |
| 8,337,834 B2 | 12/2012 | Fraser |
| 8,354,221 B2 | 1/2013 | Roy |
| 8,361,503 B2 | 1/2013 | Badylak |
| 8,367,405 B2 | 2/2013 | Gronthos |
| 8,377,143 B2 | 2/2013 | Hamby |
| 8,394,141 B2 | 3/2013 | Mills |
| 8,394,631 B2 | 3/2013 | Hampson |
| 8,404,229 B2 | 3/2013 | Fraser |
| 8,425,600 B2 | 4/2013 | Maxwell |
| 8,435,943 B2 | 5/2013 | Garigapati |
| 8,446,586 B2 | 5/2013 | Wu |
| 8,455,008 B2 | 6/2013 | Johnson |
| 8,460,691 B2 | 6/2013 | Lauritzen |
| 8,460,860 B2 | 6/2013 | Williams et al. |
| 8,470,520 B2 | 6/2013 | Ott |
| 8,470,595 B2 | 6/2013 | Torihashi |
| 8,475,824 B2 | 7/2013 | McKay |
| 8,475,827 B2 | 7/2013 | Hamby |
| 8,481,253 B2 | 7/2013 | Wouters |
| 8,491,885 B2 | 7/2013 | Oh |
| 8,496,970 B2 | 7/2013 | Binette |
| 8,497,121 B2 | 7/2013 | Yao et al. |
| 8,497,236 B2 | 7/2013 | Benedict |
| 8,512,695 B2 | 8/2013 | Austen, Jr. |
| 8,524,253 B2 | 9/2013 | Kinnane |
| 8,529,962 B2 | 9/2013 | Morris |
| 8,530,415 B2 | 9/2013 | Naughton |
| 8,541,372 B2 | 9/2013 | Shah |
| 8,545,855 B2 | 10/2013 | Boyden |
| 8,545,856 B2 | 10/2013 | Boyden |
| 8,545,857 B2 | 10/2013 | Boyden |
| 8,551,506 B2 | 10/2013 | Boyden |
| 8,557,581 B2 | 10/2013 | Ngo |
| 8,563,012 B2 | 10/2013 | Boyden |
| 8,568,363 B2 | 10/2013 | Boyden |
| 8,574,614 B2 | 11/2013 | Liu |
| 8,574,826 B2 | 11/2013 | Wolfinbarger |
| 8,592,209 B2 | 11/2013 | Khurgel |
| 8,597,352 B2 | 12/2013 | Schwartz |
| 8,603,494 B2 | 12/2013 | Boyden |
| 8,603,495 B2 | 12/2013 | Boyden |
| 8,603,496 B2 | 12/2013 | Boyden et al. |
| 8,603,819 B2 | 12/2013 | Allon |
| 8,631,397 B2 | 1/2014 | Brar et al. |
| 8,637,066 B2 | 1/2014 | Binnette |
| 8,641,775 B2 | 2/2014 | Harmon |
| 8,679,809 B2 | 3/2014 | Chan |
| 8,685,407 B2 | 4/2014 | Weiner et al. |
| 8,691,542 B2 | 4/2014 | Guilak |
| 8,691,946 B2 | 4/2014 | Sanford |
| 8,693,653 B1 | 4/2014 | Abraham |
| 8,715,733 B2 | 5/2014 | Kadiyala |
| 8,734,525 B2 | 5/2014 | Behnam et al. |
| 8,735,054 B1 | 5/2014 | Sun |
| 8,747,467 B2 | 6/2014 | Mills |
| 8,753,689 B2 | 6/2014 | Morris |
| 8,758,781 B2 | 6/2014 | Ward |
| 8,784,499 B2 | 6/2014 | Owens |
| 8,779,089 B2 | 7/2014 | Sanford |
| 8,784,890 B2 | 7/2014 | Farrell |
| 8,791,071 B1 | 7/2014 | Malinin |
| 8,802,081 B2 | 8/2014 | Wang |
| 8,828,724 B2 | 9/2014 | Blanc-Brude |
| 8,834,928 B1 | 9/2014 | Truncale et al. |
| 8,835,170 B2 | 9/2014 | Katz |
| 8,858,981 B2 | 10/2014 | Geistlich |
| 8,865,199 B2 | 10/2014 | Coleman |
| 8,883,210 B1 | 11/2014 | Truncale et al. |
| 8,883,408 B2 | 11/2014 | Hamby |
| 8,906,110 B2 | 12/2014 | Semler |
| 8,927,202 B2 | 1/2015 | Shimko |
| 8,936,651 B2 | 1/2015 | Yang |
| 8,940,692 B2 | 1/2015 | Malinin |
| 8,940,698 B2 | 1/2015 | Malinin |
| 8,945,920 B2 | 2/2015 | Casteilla |
| 8,962,044 B2 | 2/2015 | Anderson |
| 8,962,324 B2 | 2/2015 | Matheny |
| 8,986,377 B2 | 3/2015 | Richter |
| 8,986,378 B2 | 3/2015 | Koob |
| 8,992,628 B2 | 3/2015 | Drapeau |
| 8,999,709 B2 | 4/2015 | Fernandez Miguel et al. |
| 9,005,646 B2 | 4/2015 | Masinaei |
| 9,011,537 B2 | 4/2015 | Wei |
| 9,011,985 B2 | 4/2015 | Dai |
| 9,023,416 B2 | 5/2015 | Moore |
| 9,034,386 B2 | 5/2015 | Flynn |
| 9,034,644 B2 | 5/2015 | Masinaei |
| 9,044,455 B2 | 6/2015 | Shah |
| 9,056,084 B2 | 6/2015 | Yilkomi |
| 9,057,052 B2 | 6/2015 | Kobayashi |
| 9,074,190 B2 | 7/2015 | Yoshimura |
| 9,089,117 B2 | 7/2015 | Grande |
| 9,089,523 B2 | 7/2015 | Xu |
| 9,090,678 B2 | 7/2015 | Gronthos |
| 9,102,913 B2 | 8/2015 | Roach |
| 9,115,176 B2 | 8/2015 | Hocquaux |
| 9,125,743 B2 | 9/2015 | Chen et al. |
| 9,125,971 B2 | 9/2015 | Wolfinbarger |
| 9,132,208 B2 | 9/2015 | Chen |
| 9,133,431 B2 | 9/2015 | Peterson |
| 9,149,562 B2 | 10/2015 | Shortkroff et al. |
| 9,162,011 B2 | 10/2015 | Stilwell |
| 9,173,903 B2 | 11/2015 | Singh |

(56) References Cited

U.S. PATENT DOCUMENTS

| | | |
|---|---|---|
| 9,186,253 B2 | 11/2015 | Barrett et al. |
| 9,186,380 B2 | 11/2015 | Shi et al. |
| 9,192,695 B2 | 11/2015 | Shi |
| 9,199,002 B2 | 12/2015 | Mao |
| 9,200,255 B2 | 12/2015 | Halvorsen |
| 9,205,172 B2 | 12/2015 | Neethling |
| 9,206,442 B2 | 12/2015 | Chen |
| 9,211,307 B2 | 12/2015 | McDevitt |
| 9,216,194 B2 | 12/2015 | Ratcliffe |
| 9,216,236 B2 | 12/2015 | Machluf |
| 9,220,803 B2 | 12/2015 | Lidgren |
| 9,238,090 B1 | 1/2016 | Fette |
| 9,238,793 B2 | 1/2016 | Chen |
| 9,249,393 B2 | 2/2016 | Gimble |
| 9,271,821 B2 | 3/2016 | Roock |
| 9,278,165 B2 | 3/2016 | Park |
| 9,296,781 B2 | 3/2016 | Schendel |
| 9,301,975 B2 | 4/2016 | Rouy |
| 9,352,003 B1 | 5/2016 | Semler et al. |
| 9,358,327 B1 | 6/2016 | Venturi |
| 9,370,536 B2 | 6/2016 | Sun |
| 9,370,606 B2 | 6/2016 | Nakamura |
| 9,375,513 B2 | 6/2016 | Sun |
| 9,381,273 B2 | 7/2016 | Gazit |
| 9,382,422 B2 | 7/2016 | Owens |
| 9,382,514 B2 | 7/2016 | Hantash |
| 9,393,097 B2 | 7/2016 | McCullen et al. |
| 9,393,195 B2 | 7/2016 | Mizuno et al. |
| 9,408,875 B2 | 8/2016 | Masinaei |
| 9,421,304 B2 | 8/2016 | Shortkroff et al. |
| 9,433,702 B2 | 9/2016 | Malinin |
| 9,441,200 B2 | 9/2016 | Rosson |
| 9,446,077 B2 | 9/2016 | Southard |
| 9,504,770 B2 | 11/2016 | Xu |
| 9,511,171 B2 | 12/2016 | Binette et al. |
| 9,655,951 B2 | 5/2017 | Moore |
| 9,700,415 B2 | 7/2017 | Barrett et al. |
| 9,744,043 B2 | 8/2017 | Chen et al. |
| 9,855,393 B2 | 1/2018 | Schmieding et al. |
| 9,889,233 B2 | 2/2018 | Lidgren |
| 9,962,467 B2 | 5/2018 | Masinaei et al. |
| 9,993,326 B2 | 6/2018 | Shortkroff et al. |
| 10,092,600 B2 | 10/2018 | Huang et al. |
| 10,130,736 B1 | 11/2018 | Semler et al. |
| 2001/0012965 A1 | 8/2001 | Masuda |
| 2001/0038848 A1 | 11/2001 | Donda |
| 2001/0043940 A1 | 11/2001 | Boyce et al. |
| 2001/0051834 A1 | 12/2001 | Frondoza |
| 2002/0076400 A1 | 6/2002 | Katz |
| 2002/0106394 A1 | 8/2002 | Tucker |
| 2003/0009237 A1 | 1/2003 | Bonutti |
| 2003/0039676 A1 | 2/2003 | Boyce |
| 2003/0054331 A1 | 3/2003 | Fraser |
| 2003/0082152 A1 | 5/2003 | Hedrick |
| 2003/0099620 A1 | 5/2003 | Zaleske |
| 2003/0104026 A1 | 6/2003 | Wironen |
| 2003/0152558 A1 | 8/2003 | Luft |
| 2003/0161816 A1 | 8/2003 | Fraser |
| 2003/0162707 A1 | 8/2003 | Fraser |
| 2003/0170214 A1 | 9/2003 | Bader |
| 2003/0181978 A1 | 9/2003 | Brown |
| 2003/0211130 A1 | 11/2003 | Sanders |
| 2004/0030406 A1 | 2/2004 | Ochi |
| 2004/0048375 A1 | 3/2004 | Alt |
| 2004/0052768 A1 | 3/2004 | Morrison |
| 2004/0052830 A1 | 3/2004 | Konertz |
| 2004/0059364 A1 | 3/2004 | Gaskins |
| 2004/0067218 A1 | 4/2004 | Castiella |
| 2004/0078090 A1 | 4/2004 | Binette et al. |
| 2004/0082063 A1 | 4/2004 | Deshpande |
| 2004/0092011 A1 | 5/2004 | Wilkison |
| 2004/0117033 A1 | 6/2004 | Frondoza |
| 2004/0151705 A1 | 8/2004 | Mizuno et al. |
| 2004/0170663 A1 | 9/2004 | Wane |
| 2004/0171146 A1 | 9/2004 | Katz |
| 2004/0191226 A1 | 9/2004 | Badylak |
| 2004/0197367 A1 | 10/2004 | Rezania |
| 2004/0228901 A1 | 11/2004 | Trieu |
| 2004/0230303 A1 | 11/2004 | Gomes |
| 2004/0241146 A1 | 12/2004 | Biscup |
| 2004/0265971 A1 | 12/2004 | Sato |
| 2005/0008626 A1 | 1/2005 | Fraser |
| 2005/0009000 A1 | 1/2005 | Wilhelm |
| 2005/0013870 A1 | 1/2005 | Freyman |
| 2005/0033449 A1 | 2/2005 | Ashman |
| 2005/0048035 A1 | 3/2005 | Fraser |
| 2005/0048036 A1 | 3/2005 | Fraser |
| 2005/0064042 A1 | 3/2005 | Vunjak-Novakovic |
| 2005/0076396 A1 | 4/2005 | Katz |
| 2005/0095228 A1 | 5/2005 | Fraser |
| 2005/0113937 A1 | 5/2005 | Binette |
| 2005/0118228 A1 | 6/2005 | Trieu |
| 2005/0125077 A1 | 6/2005 | Harmon |
| 2005/0136042 A1 | 6/2005 | Betz |
| 2005/0152882 A1 | 7/2005 | Kizer |
| 2005/0152941 A1 | 7/2005 | Hunter |
| 2005/0152944 A1 | 7/2005 | Hunter |
| 2005/0152945 A1 | 7/2005 | Hunter |
| 2005/0152947 A1 | 7/2005 | Hunter |
| 2005/0152948 A1 | 7/2005 | Hunter |
| 2005/0153442 A1 | 7/2005 | Katz |
| 2005/0171616 A1 | 8/2005 | Sung |
| 2005/0182463 A1 | 8/2005 | Hunter |
| 2005/0182496 A1 | 8/2005 | Hunter |
| 2005/0186286 A1 | 8/2005 | Takami |
| 2005/0187639 A1 | 8/2005 | Hunter |
| 2005/0203635 A1 | 9/2005 | Hunter |
| 2005/0209705 A1 | 9/2005 | Niederauer |
| 2005/0222687 A1 | 10/2005 | Vunjak-Novakovic |
| 2005/0250202 A1 | 11/2005 | March |
| 2005/0256588 A1 | 11/2005 | Sawa |
| 2005/0260176 A1 | 11/2005 | Ayares |
| 2005/0260748 A1 | 11/2005 | Chang |
| 2005/0266390 A1 | 12/2005 | Ueda |
| 2005/0282275 A1 | 12/2005 | Katz |
| 2005/0288796 A1 | 12/2005 | Awad et al. |
| 2006/0045872 A1 | 3/2006 | Miguel |
| 2006/0051865 A1 | 3/2006 | Higgins |
| 2006/0073124 A1 | 4/2006 | Castro |
| 2006/0078993 A1 | 4/2006 | Phan |
| 2006/0083720 A1 | 4/2006 | Fraser |
| 2006/0153797 A1 | 7/2006 | Bortolotto |
| 2006/0171932 A1 | 8/2006 | Hendricks |
| 2006/0193885 A1 | 8/2006 | Neethling et al. |
| 2006/0203636 A1 | 9/2006 | Ko |
| 2006/0204556 A1 | 9/2006 | Daniels |
| 2006/0210643 A1 | 9/2006 | Truncale |
| 2006/0228796 A1 | 10/2006 | Kolkin |
| 2006/0282173 A1 | 12/2006 | McFetridge |
| 2007/0010897 A1 | 1/2007 | Stone |
| 2007/0026518 A1 | 2/2007 | Healy |
| 2007/0027543 A1 | 2/2007 | Gimble |
| 2007/0036768 A1 | 2/2007 | Fraser |
| 2007/0077649 A1 | 4/2007 | Sammak |
| 2007/0083270 A1 | 4/2007 | Masinaei |
| 2007/0104692 A1 | 5/2007 | Quijano |
| 2007/0104693 A1 | 5/2007 | Quijano |
| 2007/0134343 A1 | 6/2007 | Trieu et al. |
| 2007/0148766 A1 | 6/2007 | Yoshimura |
| 2007/0172812 A1 | 6/2007 | Ochi |
| 2007/0185585 A1 | 8/2007 | Bracy |
| 2007/0196421 A1 | 8/2007 | Hunter |
| 2007/0202592 A1 | 8/2007 | Kitagawa |
| 2007/0207125 A1 | 9/2007 | Bothwell |
| 2007/0212336 A1 | 9/2007 | Fulkerson |
| 2007/0212396 A1 | 9/2007 | Zheng |
| 2007/0213822 A1 | 9/2007 | Trieu |
| 2007/0244568 A1 | 10/2007 | Matsuda |
| 2007/0248580 A1 | 10/2007 | Castro |
| 2007/0249044 A1 | 10/2007 | Desai |
| 2007/0258956 A1 | 11/2007 | Higgins |
| 2007/0264239 A1 | 11/2007 | Huard |
| 2007/0269791 A1 | 11/2007 | Takami |
| 2007/0276489 A1 | 11/2007 | Bindell et al. |

(56) References Cited

U.S. PATENT DOCUMENTS

| | | |
|---|---|---|
| 2007/0282456 A1 | 12/2007 | Geng |
| 2007/0292401 A1 | 12/2007 | Harmon |
| 2007/0299508 A1 | 12/2007 | Morrison |
| 2008/0014179 A1 | 1/2008 | Ferree |
| 2008/0026461 A1 | 1/2008 | Deshpande |
| 2008/0071385 A1 | 3/2008 | Binette et al. |
| 2008/0077251 A1 | 3/2008 | Chen |
| 2008/0097601 A1 | 4/2008 | Codori-Hurff |
| 2008/0133008 A1 | 6/2008 | Truncale |
| 2008/0138414 A1 | 6/2008 | Huckle |
| 2008/0154386 A1 | 6/2008 | Morris |
| 2008/0160085 A1 | 7/2008 | Boland |
| 2008/0160496 A1 | 7/2008 | Rzepakovsky et al. |
| 2008/0187518 A1 | 8/2008 | Ogle |
| 2008/0195229 A1 | 8/2008 | Quijano |
| 2008/0206208 A1 | 8/2008 | Casteilla |
| 2008/0213235 A1 | 9/2008 | Katz |
| 2008/0220044 A1 | 9/2008 | Semler |
| 2008/0260794 A1 | 10/2008 | Lauritzen |
| 2008/0269762 A1 | 10/2008 | Simon |
| 2008/0274157 A1 | 11/2008 | Vunjak-Novakovic |
| 2008/0274184 A1 | 11/2008 | Hunt |
| 2008/0274185 A1 | 11/2008 | Mao |
| 2008/0279825 A1* | 11/2008 | Malinin ............ A61F 2/30756 424/93.7 |
| 2008/0279939 A1 | 11/2008 | Firestone |
| 2008/0286241 A1 | 11/2008 | Lee |
| 2008/0306610 A1 | 12/2008 | Wang |
| 2008/0318317 A1 | 12/2008 | Roche |
| 2009/0012629 A1 | 1/2009 | Yao |
| 2009/0022773 A1 | 1/2009 | Springer |
| 2009/0024224 A1 | 1/2009 | Chen |
| 2009/0024229 A1 | 1/2009 | Chen et al. |
| 2009/0041729 A1 | 2/2009 | Wolfinbarger |
| 2009/0041825 A1 | 2/2009 | Kotov |
| 2009/0053277 A1 | 2/2009 | Nagaya |
| 2009/0054983 A1 | 2/2009 | Ignatius |
| 2009/0068154 A1 | 3/2009 | Ueda |
| 2009/0069901 A1 | 3/2009 | Truncale et al. |
| 2009/0123509 A1 | 5/2009 | Berkland et al. |
| 2009/0130067 A1 | 5/2009 | Buscher |
| 2009/0130756 A1 | 5/2009 | Klann |
| 2009/0138095 A1 | 5/2009 | Giordano |
| 2009/0142409 A1 | 6/2009 | Firestone |
| 2009/0148487 A1 | 6/2009 | Siedler et al. |
| 2009/0149893 A1 | 6/2009 | Semler et al. |
| 2009/0157087 A1 | 6/2009 | Wei et al. |
| 2009/0163990 A1 | 6/2009 | Yang |
| 2009/0169642 A1 | 7/2009 | Fradette |
| 2009/0181104 A1 | 7/2009 | Rigotti |
| 2009/0181456 A1 | 7/2009 | Hedrick |
| 2009/0187245 A1 | 7/2009 | Steiner |
| 2009/0192602 A1 | 7/2009 | Kuehn |
| 2009/0209020 A1 | 8/2009 | Park |
| 2009/0220569 A1 | 9/2009 | Williams |
| 2009/0252711 A1 | 10/2009 | Boquest |
| 2009/0269315 A1 | 10/2009 | Fraser |
| 2009/0291112 A1 | 11/2009 | Truncale |
| 2009/0292311 A1 | 11/2009 | Olmo |
| 2009/0297488 A1 | 12/2009 | Fraser |
| 2009/0304644 A1 | 12/2009 | Hedrick |
| 2009/0304646 A1 | 12/2009 | Sakurada |
| 2009/0304654 A1 | 12/2009 | Lue |
| 2009/0312842 A1 | 12/2009 | Bursac et al. |
| 2009/0319045 A1 | 12/2009 | Truncale et al. |
| 2010/0015104 A1 | 1/2010 | Fraser |
| 2010/0015204 A1 | 1/2010 | Hedrick |
| 2010/0040687 A1 | 2/2010 | Pedrozo |
| 2010/0047213 A1 | 2/2010 | Zeitlin |
| 2010/0082113 A1 | 4/2010 | Gingras |
| 2010/0098739 A1 | 4/2010 | Katz |
| 2010/0105100 A1 | 4/2010 | Sakurada |
| 2010/0111850 A1 | 5/2010 | Boyden et al. |
| 2010/0112031 A1 | 5/2010 | Katz |
| 2010/0112543 A1 | 5/2010 | Ngo |
| 2010/0112695 A1 | 5/2010 | Min |
| 2010/0112696 A1 | 5/2010 | Min |
| 2010/0119492 A1 | 5/2010 | Hans |
| 2010/0119496 A1 | 5/2010 | Wilkison |
| 2010/0120069 A1 | 5/2010 | Sakurada |
| 2010/0129330 A1 | 5/2010 | Wilkison |
| 2010/0136114 A1 | 6/2010 | Mao |
| 2010/0145473 A1 | 6/2010 | Yannas |
| 2010/0151435 A1 | 6/2010 | Thatte |
| 2010/0151574 A1 | 6/2010 | Matsuyama |
| 2010/0158876 A1 | 6/2010 | Alessandri |
| 2010/0267107 A1 | 6/2010 | Zuba-Surma |
| 2010/0166824 A1 | 7/2010 | Naughton |
| 2010/0173411 A1 | 7/2010 | Katz |
| 2010/0178681 A1 | 7/2010 | Lee |
| 2010/0179639 A1 | 7/2010 | Bloor |
| 2010/0183568 A1 | 7/2010 | Matsuyama |
| 2010/0196333 A1 | 8/2010 | Gaskins et al. |
| 2010/0196439 A1 | 8/2010 | Beck |
| 2010/0196478 A1 | 8/2010 | Masters |
| 2010/0227399 A1 | 9/2010 | Funaki |
| 2010/0233131 A1 | 9/2010 | Kang |
| 2010/0239540 A1 | 9/2010 | Brinchmann |
| 2010/0239542 A1 | 9/2010 | Young |
| 2010/0239543 A1 | 9/2010 | Young |
| 2010/0274362 A1 | 10/2010 | Yayon |
| 2010/0285521 A1 | 11/2010 | Vossman |
| 2010/0285580 A1 | 11/2010 | Evans |
| 2010/0286795 A1 | 11/2010 | Stone et al. |
| 2010/0291219 A1 | 11/2010 | Karp |
| 2010/0303766 A1 | 12/2010 | Miyaji |
| 2010/0303774 A1 | 12/2010 | Hedrick |
| 2010/0304477 A1 | 12/2010 | Buscher |
| 2010/0310527 A1 | 12/2010 | Alt |
| 2010/0322908 A1 | 12/2010 | Everland et al. |
| 2010/0322994 A1 | 12/2010 | Kizer et al. |
| 2010/0330047 A1 | 12/2010 | Valorani |
| 2011/0002972 A1 | 1/2011 | Bosserhoff et al. |
| 2011/0002996 A1 | 1/2011 | McQuillan et al. |
| 2011/0009963 A1 | 1/2011 | Binnette et al. |
| 2011/0010023 A1 | 1/2011 | Kunzig et al. |
| 2011/0014701 A1 | 1/2011 | Ghosh |
| 2011/0027879 A1 | 2/2011 | Katz |
| 2011/0035004 A1 | 2/2011 | Maxwell |
| 2011/0039332 A1 | 2/2011 | Sakurada |
| 2011/0045044 A1 | 2/2011 | Masinaei |
| 2011/0052705 A1 | 3/2011 | Malinin |
| 2011/0064701 A1 | 3/2011 | Young |
| 2011/0064782 A1 | 3/2011 | Bloor |
| 2011/0070271 A1 | 3/2011 | Truncale et al. |
| 2011/0070647 A1 | 3/2011 | Dezawa |
| 2011/0086426 A1 | 4/2011 | Freund |
| 2011/0087338 A1 | 4/2011 | Siemionow |
| 2011/0091517 A1 | 4/2011 | Binette |
| 2011/0097381 A1 | 4/2011 | Binette et al. |
| 2011/0098826 A1 | 4/2011 | Mauck |
| 2011/0104133 A1 | 5/2011 | Tseng |
| 2011/0104242 A1 | 5/2011 | Malinin |
| 2011/0104735 A1 | 5/2011 | Buehrer |
| 2011/0110898 A1 | 5/2011 | Kleinsek |
| 2011/0111497 A1 | 5/2011 | Tamai |
| 2011/0112655 A1 | 5/2011 | Brekke |
| 2011/0117171 A1 | 5/2011 | Melican |
| 2011/0117650 A1 | 5/2011 | Riordan |
| 2011/0129447 A1 | 6/2011 | Meretzki |
| 2011/0143429 A1 | 6/2011 | Chun |
| 2011/0150845 A1 | 6/2011 | Perekkadan |
| 2011/0150846 A1 | 6/2011 | Van Epps |
| 2011/0158959 A1 | 6/2011 | McIntosh |
| 2011/0161011 A1 | 6/2011 | Flynn |
| 2011/0166669 A1 | 7/2011 | Truncale et al. |
| 2011/0171726 A1 | 7/2011 | Kang |
| 2011/0177134 A1 | 7/2011 | Harmon et al. |
| 2011/0177593 A1 | 7/2011 | Funaki |
| 2011/0182962 A1 | 7/2011 | McKay |
| 2011/0189140 A1 | 8/2011 | Christman |
| 2011/0195107 A1 | 8/2011 | Min |
| 2011/0196508 A1 | 8/2011 | Truncale et al. |
| 2011/0202142 A1 | 8/2011 | Mao |

(56) References Cited

U.S. PATENT DOCUMENTS

| | | |
|---|---|---|
| 2011/0257763 A1 | 10/2011 | Yasuda et al. |
| 2011/0262515 A1 | 10/2011 | Lauritzen et al. |
| 2011/0274668 A1 | 11/2011 | Scarborough |
| 2011/0274742 A1 | 11/2011 | Arinzeh |
| 2011/0282239 A1 | 11/2011 | Conlon et al. |
| 2011/0293667 A1 | 12/2011 | Baksh |
| 2011/0301525 A1 | 12/2011 | Nicoll et al. |
| 2011/0313538 A1 | 12/2011 | Oh |
| 2011/0313541 A1 | 12/2011 | Dennis et al. |
| 2012/0009224 A1 | 1/2012 | Kizer |
| 2012/0010728 A1 | 1/2012 | Sun |
| 2012/0015003 A1 | 1/2012 | Gleeson et al. |
| 2012/0029653 A1 | 2/2012 | Evans et al. |
| 2012/0034191 A1 | 2/2012 | Matheny |
| 2012/0039961 A1 | 2/2012 | Mollenhauer |
| 2012/0053692 A1 | 3/2012 | Voor et al. |
| 2012/0063997 A1 | 3/2012 | Hunter |
| 2012/0087948 A1 | 4/2012 | Kizer |
| 2012/0087958 A1 | 4/2012 | Dufrane |
| 2012/0089238 A1 | 4/2012 | Kang et al. |
| 2012/0109335 A1 | 5/2012 | May et al. |
| 2012/0143334 A1 | 6/2012 | Boyce et al. |
| 2012/0156265 A1 | 6/2012 | Binette et al. |
| 2012/0164116 A1 | 6/2012 | Van Epps |
| 2012/0183586 A1 | 7/2012 | Yao |
| 2012/0189588 A1 | 7/2012 | Nahas |
| 2012/0221118 A1 | 8/2012 | Bartee |
| 2012/0237558 A1 | 9/2012 | Kizer et al. |
| 2012/0263763 A1 | 10/2012 | Sun et al. |
| 2012/0264190 A1 | 10/2012 | Christman |
| 2012/0277152 A1 | 11/2012 | Ringeisen et al. |
| 2012/0282226 A1 | 11/2012 | Ayares |
| 2012/0310367 A1 | 12/2012 | Connor |
| 2012/0329034 A1 | 12/2012 | Chun |
| 2013/0011442 A1 | 1/2013 | Chan |
| 2013/0011446 A1 | 1/2013 | DePaula |
| 2013/0013068 A1 | 1/2013 | Forsell |
| 2013/0028981 A1 | 1/2013 | Gratzer |
| 2013/0030528 A1 | 1/2013 | Chen et al. |
| 2013/0158658 A1 | 6/2013 | Hayzlett |
| 2013/0189339 A1 | 7/2013 | Vachon |
| 2013/0190893 A1 | 7/2013 | Roock et al. |
| 2013/0195805 A1 | 8/2013 | Wei et al. |
| 2013/0202563 A1 | 8/2013 | Badylak |
| 2013/0231288 A1 | 9/2013 | Bhatia |
| 2013/0251687 A1 | 9/2013 | Christman |
| 2013/0251758 A1 | 9/2013 | Everland |
| 2013/0259838 A1 | 10/2013 | Yamanaka et al. |
| 2013/0273121 A1 | 10/2013 | Mizuno et al. |
| 2013/0274890 A1 | 10/2013 | McKay |
| 2013/0330391 A1 | 12/2013 | Malinin |
| 2013/0330415 A1 | 12/2013 | Yao et al. |
| 2013/0338792 A1 | 12/2013 | Schmieding |
| 2013/0345826 A1 | 12/2013 | Li et al. |
| 2014/0017206 A1 | 1/2014 | Barere |
| 2014/0017283 A1 | 1/2014 | Yoo et al. |
| 2014/0017292 A1 | 1/2014 | Yoo et al. |
| 2014/0025166 A1 | 1/2014 | Bonutti |
| 2014/0030309 A1 | 1/2014 | Yoo et al. |
| 2014/0056865 A1 | 2/2014 | Samaniego |
| 2014/0134212 A1 | 5/2014 | Shi et al. |
| 2014/0178343 A1 | 6/2014 | Yao et al. |
| 2014/0178450 A1 | 6/2014 | Christman |
| 2014/0220096 A1 | 7/2014 | Malinin |
| 2014/0227336 A1 | 8/2014 | Guilak |
| 2014/0243993 A1 | 8/2014 | Barrett et al. |
| 2014/0294911 A1 | 10/2014 | Malinin |
| 2014/0302104 A1 | 10/2014 | Harris |
| 2014/0314822 A1 | 10/2014 | Carter et al. |
| 2014/0341871 A1 | 11/2014 | Morris |
| 2014/0377833 A1 | 12/2014 | Chen |
| 2015/0004211 A1 | 1/2015 | Yoo et al. |
| 2015/0017140 A1 | 1/2015 | Bhatra |
| 2015/0017222 A1 | 1/2015 | Yoo et al. |
| 2015/0021058 A1 | 1/2015 | Devloo et al. |
| 2015/0037386 A1 | 2/2015 | Shimp |
| 2015/0037432 A1 | 2/2015 | Malinin |
| 2015/0037436 A1 | 2/2015 | Huang |
| 2015/0079145 A1 | 3/2015 | Garigapati et al. |
| 2015/0093429 A1 | 4/2015 | Carter et al. |
| 2015/0110753 A1 | 4/2015 | Wang |
| 2015/0112089 A1 | 4/2015 | Finch |
| 2015/0119994 A1 | 4/2015 | Kang et al. |
| 2015/0140057 A1 | 5/2015 | Yoo et al. |
| 2015/0182559 A1 | 7/2015 | Masinaei et al. |
| 2015/0202348 A1 | 7/2015 | Dvir |
| 2015/0217023 A1 | 8/2015 | Masinaei et al. |
| 2015/0246072 A1 | 9/2015 | Bhatia et al. |
| 2015/0256309 A1 | 9/2015 | Tong et al. |
| 2015/0290248 A1 | 10/2015 | Peddie |
| 2016/0008511 A1 | 1/2016 | Stilwell |
| 2016/0008512 A1 | 1/2016 | Stilwell |
| 2016/0008515 A1 | 1/2016 | Stilwell |
| 2016/0022740 A1 | 1/2016 | Shi et al. |
| 2016/0024463 A1 | 1/2016 | Roach |
| 2016/0030487 A1 | 2/2016 | Bachrach |
| 2016/0030635 A1 | 2/2016 | Bhatia |
| 2016/0030636 A1 | 2/2016 | Muir |
| 2016/0045639 A1 | 2/2016 | Chen |
| 2016/0051728 A1 | 2/2016 | Flynn |
| 2016/0066563 A1 | 3/2016 | Moscatello |
| 2016/0067377 A1 | 3/2016 | Shi et al. |
| 2016/0090572 A1 | 3/2016 | Chen |
| 2016/0113863 A1 | 4/2016 | Kolle |
| 2016/0135940 A1 | 5/2016 | Roock |
| 2016/0144086 A1 | 5/2016 | Park |
| 2016/0159884 A1 | 6/2016 | Schendel |
| 2016/0160172 A1 | 6/2016 | Cimino |
| 2016/0175479 A1 | 6/2016 | Ratcliffe |
| 2016/0184479 A1 | 6/2016 | Fette |
| 2016/0186125 A1 | 6/2016 | Bertoni |
| 2016/0192640 A1 | 7/2016 | Bertoni |
| 2016/0193382 A1 | 7/2016 | Levenberg |
| 2016/0193386 A1 | 7/2016 | Kennedy |
| 2016/0235892 A1 | 8/2016 | Detamore et al. |
| 2016/0256606 A1 | 9/2016 | Sun |
| 2016/0271295 A1 | 9/2016 | Sun |
| 2016/0326493 A1 | 11/2016 | Malinin et al. |
| 2016/0331507 A1 | 11/2016 | Shortkroff et al. |
| 2016/0354207 A1 | 12/2016 | Li et al. |
| 2016/0367727 A1 | 12/2016 | Mizuno et al. |
| 2017/0049930 A1 | 2/2017 | Nasert et al. |
| 2017/0049931 A1 | 2/2017 | Binette et al. |
| 2017/0065742 A1 | 3/2017 | Detamore et al. |
| 2017/0128633 A1 | 5/2017 | Malinin |
| 2017/0165400 A1 | 6/2017 | Awad et al. |
| 2017/0197011 A1 | 7/2017 | Chu et al. |
| 2017/0232144 A1 | 8/2017 | Kelly et al. |
| 2017/0348458 A1 | 12/2017 | Kesti et al. |
| 2017/0360989 A1 | 12/2017 | Kizer et al. |
| 2018/0078375 A1 | 3/2018 | Barrett et al. |
| 2018/0104062 A1 | 4/2018 | Chen et al. |
| 2018/0177916 A1 | 6/2018 | Masinaei et al. |
| 2019/0008903 A1 | 1/2019 | Huang et al. |
| 2019/0134265 A1 | 5/2019 | Semler et al. |

FOREIGN PATENT DOCUMENTS

| | | |
|---|---|---|
| EP | 0518389 A2 | 12/1992 |
| EP | 1740121 | 1/2007 |
| EP | 2265220 | 12/2010 |
| EP | 2919794 | 9/2015 |
| EP | 3027235 | 6/2016 |
| WO | 1996/039159 | 12/1996 |
| WO | 2002/036049 | 5/2002 |
| WO | 2003/024463 | 3/2003 |
| WO | 2004096983 | 11/2004 |
| WO | 2005/110278 | 11/2005 |
| WO | 2005110278 | 11/2005 |
| WO | 2006042311 | 4/2006 |
| WO | 2006/101885 | 9/2006 |
| WO | 2007/025290 | 3/2007 |
| WO | 2007024238 | 3/2007 |
| WO | 2007037572 A1 | 4/2007 |

(56) References Cited

FOREIGN PATENT DOCUMENTS

| WO | 2007/049125 | | 5/2007 |
|---|---|---|---|
| WO | 2008106254 | | 9/2008 |
| WO | 2008154623 | A2 | 12/2008 |
| WO | 2009/011849 | | 1/2009 |
| WO | 2009102452 | A2 | 8/2009 |
| WO | 2011/019822 | | 2/2011 |
| WO | 2011019822 | A2 | 2/2011 |
| WO | 2011/087743 | | 7/2011 |
| WO | 2011087743 | A2 | 7/2011 |
| WO | 2012/002986 | | 1/2012 |
| WO | 2012002986 | A2 | 1/2012 |
| WO | 2012/080706 | | 6/2012 |
| WO | 2012/166784 | | 12/2012 |
| WO | 2012166784 | A1 | 12/2012 |
| WO | 2014/039429 | | 3/2014 |
| WO | 2014052376 | | 4/2014 |
| WO | 2014/130883 | | 8/2014 |
| WO | 2015017500 | | 2/2015 |
| WO | 2015035115 | | 3/2015 |
| WO | 2015/048317 | | 4/2015 |
| WO | 2015/188020 | | 12/2015 |
| WO | 2016/018710 | | 2/2016 |
| WO | 2016/019170 | | 2/2016 |
| WO | 2016/024025 | | 2/2016 |
| WO | 2016/092106 | | 6/2016 |
| WO | 2015/017500 | | 2/2019 |

OTHER PUBLICATIONS

Sheldon et al., J. Cell Biol. 4(4): 401-406 (1958).*
Australian Patent Examination Report No. 1 regarding Australian Patent Application No. 2014296259, dated Jun. 2, 2016.
International Search Report and Written Opinion for International (PCT) Application No. PCT/US2014/025619, dated Jun. 30, 2014.
International Search Report and Written Opinion of the International Searching Authority in regard to International Application No. PCT/US2014/048797, dated Oct. 9, 2014.
Non-Final Office Action dated Sep. 22, 2016 by the USPTO regarding U.S. Appl. No. 14/446,629.
Choi, J. et al., Human extracellular matrix (ECM) powders for injectable cell delivery and adipose tissue engineering, J Control Release, 139, 1, (2009), p. 2-7.
Clarke, KM, et al., Intestine submucosa and Polypropylene Mesh for Abdominal Wall Repair in Dogs, Journal of Surgical Research, vol. 60, Iss. 1, pp. 107-114, (Jan. 1996).
Coleman III, W. et al., Autologous Collagen? Lipocytic Dermal Augmentation A Histopathologic Study, J. Dermatol. Surg. Oneal., vol. 19, pp. 1032-1040, (1993).
Erdag, et al., Fibroblasts Improve Performance of Cul Tu Red Composite Skin Substitutes on Athymic Mice, Burns, 30 (2004) pp. 322-328.
Grauss, R.W. et al., Decellularization of Rat Aortic Valve Allografts Reduces Leaflet Destruction and Extracellular Matrix Remodeling, Journal Thoracic and Cardiovascular Surgery, 126, 2003-2010, (2003).
Hara, A. et al., Lipid extraction of tissues with a low-toxicity solvent, Analytical Biochemistry, 90, 1, (1978), p. 420-426.
Hubbell, J., Materials as morphogenic guides in tissue engineering, Current Opinion in Biotechnology, 14, pp. 551-558,(2003).
Kropp, BP., et al., Experimental assessment of small intestinal submucosa as a bladder wall substitute, Urology, vol. 46, Iss. 3, pp. 396-400, (Sep. 1995).
Kropp, BP., et al., Regenerative urinary bladder augmentation using small intestinal submucosa: urodynamic and histopathologic assessment in long-term canine bladder augmentations, J. Ural., vol. 155, Iss. 6, pp. 2098-2104 (Jun. 1996).
Oliver, et al., "Reconstruction of Full-Thickness Loss Skin Wounds Using Skin Collagen Allografts", British Journal of Plastic Surgery, 32 (1979), pp. 87-90.
Prevel, CD., et al., Small intestinal submucosa: utilization for repair of rodent abdominal wall defects, Ann. Plast. Surg., vol. 35, Iss. 4, pp. 374-380, (Oct. 1995).
Schmidt, C. et al., Acellular vascular tissues: natural biomaterials for tissue repair and tissue engineering, Biomaterials, 21, (2000), p. 2215-2231.
Sekiya, S. et al., Bioengineered cardiac cell sheet grafts have intrinsic angiogenic potential, Biochemical and Biophysical Research Communications, 341, pp. 573-582, (2006).
Takasaki, S. et al., Human type VI collagen: purification from human subcutaneous fat tissue and an immunohistochemical study of morphea and systemic sclerosis, J Dermatol, 22, 7, (Jul. 1995), p. 480-485.
Ueda, Y. et al., Antigen clearing from porcine heart valves with preservation of structural integrity, The International Journal of Artificial Organs, vol. 29, No. 8, pp. 781-789, (2006).
Wang, L. et al., Combining decellularized human adipose tissue extracellular matrix and adipose-derived stem cells for adipose tissue engineering, Acta Biomater, 9, 11, (2013), p. 8921-8931.
Wellisz, T. et al., Ostene, a new water-soluble bone hemostasis agent, J. Craniofac. Surg., vol. 17, Iss. 3, pp. 420-425, (May 2006).
Wilshaw, S. et al., Production of an Acellular Amniotic Membrane Matrix for Use in Tissue Engineering, Tissue Engineering, vol. 12, No. 8, pp. 2117-2129, (2006).
U.S. Appl. No. 15/217,409 entitled "Acellular Soft Tissue-Derived Matrices and Methods for Preparing Same", filed Jul. 22, 2016.
Office Action for Columbian Patent Application No. 16-049.384, dated Apr. 19, 2016.
Translation of Office Action for Columbian Patent Application No. 16-049.384, dated Apr. 19, 2016.
U.S. Appl. No. 61/345,057, filed May 14, 2010.
U.S. Appl. No. 62/071,946, filed Nov. 7, 2014.
U.S. Appl. No. 14/537,253, filed Nov. 10, 2014.
U.S. Appl. No. 16/229,650, filed Dec. 21, 2018.
Restriction Requirement issued for U.S. Appl. No. 16/121,969, dated Oct. 8, 2019.
Final Office Action for U.S. Appl. No. 15/217,409, dated Feb. 22, 2019.
Restriction Requirement for U.S. Appl. No. 13/108,856, dated Aug. 9, 2012.
Non-Final Office Action for U.S. Appl. No. 13/108,856, dated Feb. 27, 2014.
Restriction Requirement for U.S. Appl. No. 13/690,542, dated Jul. 3, 2014.
Final Office Action for U.S. Appl. No. 13/690,542, dated Jul. 2, 2015.
Oh, 2002, Cryobiology, 44: 279-287.
Non-Final Office Action for U.S. Appl. No. 13/948,798, dated Nov. 27, 2013.
Non-Final Office Action for U.S. Appl. No. 14/933,176, dated Jul. 12, 2016.
Final Office Action for U.S. Appl. No. 14/933,176, dated Mar. 3, 2017.
Final Office Action for U.S. Appl. No. 14/933,176, dated Mar. 27, 2018.
U.S. Appl. No. 15/159,174, filed May 19, 2016.
Non-Final Office Action for U.S. Appl. No. 15/159,174, dated Jul. 9, 2018.
Mulliken (1981, Ann. Surg. 194: 366-372.
Van der Donk, 2003, Clinical Orthopaedics and Related Research 408: 302-310.
Non-Final Office Action for U.S. Appl. No. 14/446,629, dated Sep. 22, 2016.
International Search Report for PCT/US2014/048797—WO2015/017500, dated Feb. 5, 2015.
IPRP for PCT/US2014/048797—WO2015/017500, dated Feb. 2, 2016.
Written Opinion for WO2015017500—PCT/US2014/048797, dated Feb. 5, 2015.
Examination Report for AU2014296259, dated Jun. 2, 2016.
Examination Report No. 2, for AU2014296259, dated Jan. 9, 2017.

(56) References Cited

OTHER PUBLICATIONS

Wang L., et al., "Combining decellularized human adipose tissue extracellular matrix and adipose-derived stem cells for adipose tissue engineering." Acta Biometer., 9/11, pp. 8921-8931, Nov. 1, 2013.
Office Action for EP 3027235, dated May 23, 2017.
Office Action for EP 3027235, dated Mar. 6, 2018.
Office Action for EP 3027235, dated Nov. 30, 2018.
Restriction Requirement issued for U.S. Appl. No. 14/378,523 dated Mar. 31, 2016.
Non-Final Office Action for U.S. Appl. No. 14/378,523, dated Sep. 30, 2016.
Restriction Requirement for U.S. Appl. No. 15/388,428, dated Jul. 18, 2017.
Non-Final Office Action for U.S. Appl. No. 15/388,428, dated Sep. 15, 2017.
U.S. Appl. No. 62/214,109, filed Sep. 3, 2015.
Poon C. et al. Preparation of an Adipogenic Hydrogel from Subcutaneous Adipose Tissue. Acta Biomaterialia 9(3) 5609-5620, Mar. 2013. (Year: 2013).
U.S. Appl. No. 16/428,505, filed May 31, 2019.
U.S. Appl. No. 62/845,015, filed May 8, 2019.
U.S. Appl. No. 61/863,346, filed Aug. 7, 2013.
U.S. Appl. No. 62/032,255, filed Aug. 1, 2014.
U.S. Appl. No. 62/008,513, filed Jun. 6, 2014.

\* cited by examiner

CARTILAGE-DERIVED IMPLANTS AND METHODS OF MAKING AND USING SAME

CROSS-REFERENCE TO RELATED APPLICATIONS

The present application claims the benefit of U.S. Provisional Application No. 62/207,146, filed Aug. 19, 2015, the entire disclosure of which is hereby incorporated by reference herein.

TECHNICAL FIELD OF THE INVENTION

The present invention relates to compositions for repairing damaged or defective tissues, to methods for making such compositions, and to surgical methods for making such repairs.

BACKGROUND OF THE INVENTION

Articular cartilage in a joint acts as a lubricating smooth surface and shock absorber between joint members. Articular cartilage ranges from 1-4 mm in thickness, and is located on the mating surfaces of joints. Articular cartilage is an anatomical tissue that wears out with age, or tears due to excess loading such as in sport or other trauma related activities.

Damaged or worn articular cartilage does not heal without surgical intervention. It can be repaired in several ways using both autograft and allograft techniques. These repairs fall into two categories: Osteochondral (OC) repair that addresses both the damaged cartilage and damaged subchondral bone and chondral repair that address only damaged cartilage.

Current autograft surgical repair techniques include microfracture, osteoarticular transfer system (OATS) surgery, and autologous chondrocyte implantation (ACI). Of these only OATS addresses damage to the bone. Microfracture consists of drilling holes within the subchondral bone to provide blood flow to the damaged areas of cartilage. OATS utilizes small plugs of cartilage harvested from non-load bearing portions of the knee joint to replace damaged areas of load-bearing cartilage. These plugs can also be used in the ankle. ACI utilizes lab-grown chondrocytes generated from harvested cells within the patient's non-load-bearing cartilage. The developed cells are placed within the damaged cartilage area and held so that they can produce new cartilage-like tissue within the defect.

Current allograft surgical repair techniques include OC transplant utilizing donor cartilage and subchondral bone, and, cartilage-only grafts made from minced or milled cartilage. OC allograft tissues are provided as a whole or portion of the OC region of a long bone from which the surgeon selects and prepares an appropriately sized transplant specimen. The tissue is selected from available donated tissue to match the patients defect.

When utilizing donor cartilage and subchondral bone, worn or damaged articular cartilage and subchondral bone is removed from the patient. The damaged site is then prepared to receive the transplant, while the allograft specimen is sized and shaped. Finally the allograft specimen is press-fit in the prepared site.

Minced or milled donor cartilage is provided ready to use. The damaged cartilage area is prepared to receive the transplant and the minced or milled cartilage is placed in the prepared area either by itself or mixed with/covered by saline or biologic liquid (blood, platelet rich plasma (PRP), fibrin glue, etc.).

While current autologous and allograft cartilage therapies are, on the whole, beneficial, each suffers from its own limitations. Microfracture techniques damage the subchondral bone. Other autograft procedures generate donor sites which experience morbidity and subsequent osteoarthritis. ACI is only successful if the transplanted cells develop into cartilage-like tissue. ACI is also a two-step procedure that requires two surgeries, thus posing greater risk to the patient. OC allograft procedures require on-site preparation of the donor specimen. In addition, OC allografts are limited by the availability of suitably-sized tissues from tissue banks. Current minced and milled allograft products are limited by challenges posed by the available surgical techniques, such as tedious application or limited adhesion of the allograft product to the prepared surgical site.

SUMMARY OF THE INVENTION

In an embodiment, a cartilage-derived implant includes cartilage fibers. In an embodiment, the cartilage fibers include viable native chondrocytes. In an embodiment, the cartilage fibers include non-viable native chondrocytes. In an embodiment, the cartilage fibers include viable non-native chondrocytes. In an embodiment, the cartilage fibers include non-native non-viable chondrocytes. In an embodiment, the cartilage fibers are substantially free of chondrocytes and their components. In an embodiment, the cartilage fibers are freeze-dried. In an embodiment, the cartilage-derived implant consists of cartilage fibers. In an embodiment, the cartilage-derived implant consists of cartilage fibers and cartilage particles. In an embodiment, the cartilage particles are freeze-dried. In an embodiment, the cartilage particles are from about 0.1 millimeter (mm) to about 1 mm. In an embodiment, the cartilage-derived implant includes a biologically-compatible material other than cartilage. In an embodiment, the cartilage-derived implant is a putty-like material. In an embodiment, the cartilage-derived implant is a pre-shaped form. In an embodiment, the cartilage-derived implant is a pre-shaped form that may be reshaped by a surgeon to fit an articular cartilage defect.

In an embodiment, the cartilage fibers are prepared by a method including the step of separating the cartilage fibers, by mechanical techniques such as, without limitation, grating, scraping, slicing, cutting, or combinations thereof, from recovered cartilage, then recovering cartilage fibers having desired dimensions, and storing the recovered fibers in a growth media. In an embodiment, the selected cartilage fibers are lyophilized instead of being stored in a growth media. In an embodiment, unwanted material such as, without limitation, bone fragments and tissue fragments, are separated from the cartilage fibers after they are separated from recovered cartilage. In an embodiment, measured portions of the cartilage fibers are eventually placed in containers for storage and shipping.

In an embodiment, cartilage particles are prepared by a method including the steps of freezer-milling strips of cartilage, sieving the cartilage particles to separate cartilage particles of a desired size range, then lyophilizing the separated cartilage particles. Various suitable methods for preparing the cartilage particles are described for example, without limitation, in U.S. Patent Application Publication No. US2006/0210643, published Sep. 21, 2006, which is incorporated herein by reference in its entirety.

In an embodiment, cartilage fibers and cartilage particles are packaged separately from each other and provided to a surgeon as part of a kit. In such an embodiment, the surgeon mixes the cartilage fibers and cartilage particles to form the cartilage-derived implant. The surgeon may further mix the cartilage fibers and cartilage particles with a biologically-compatible carrier. In an embodiment, the cartilage-derived implant is provided to the surgeon in a pre-mixed form, as a putty-like material, as a pre-shaped form, or as a pre-shaped form that may be reshaped by the surgeon.

BRIEF DESCRIPTION OF THE FIGURES

For a more complete understanding of the present invention, reference is made to the following detailed description of exemplary embodiments considered in conjunction with the accompanying figures, in which.

Figure 6A:
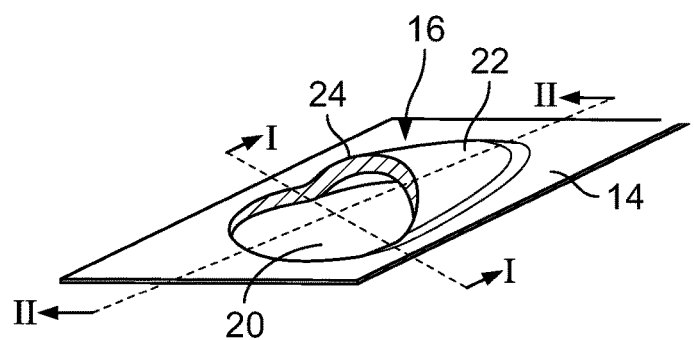
FIG. 6A is a perspective view of an exemplary embodiment of a cutting feature of a grater suitable for use in an embodiment of the present invention.
Figure 6B:
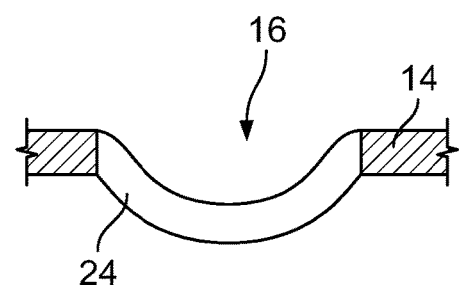
FIG. 6B is a cross-sectional view of the cutting feature of FIG. 6A.
Figure 6C:
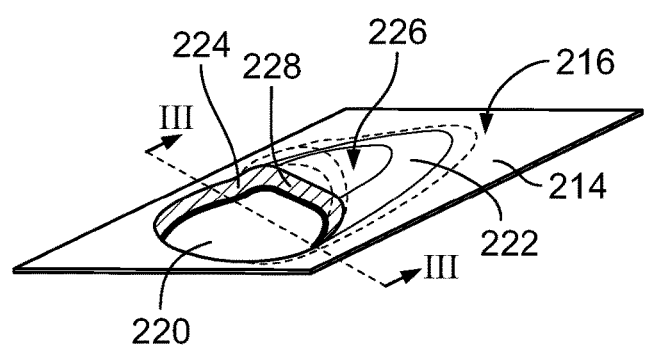
FIG. 6C is a perspective view of a cutting feature similar to that of FIG. 6A but which has been modified.
Figure 7:
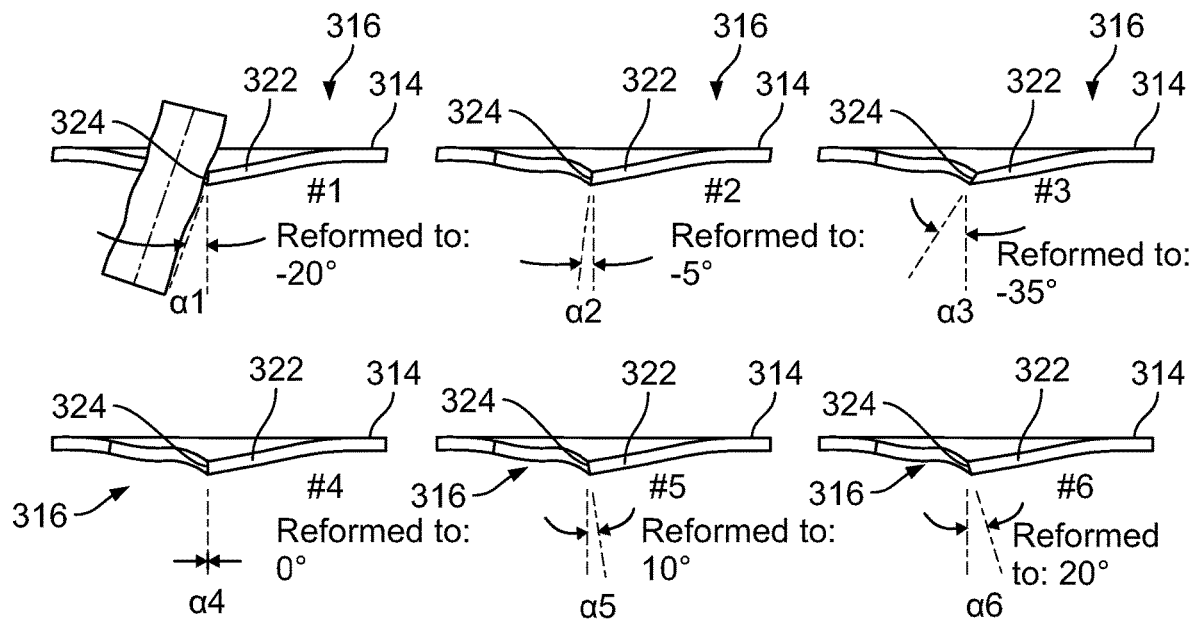
Figure 8A:
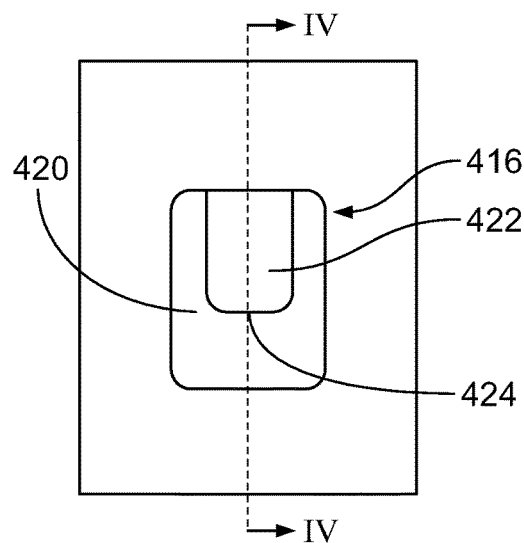
Figure 8B:
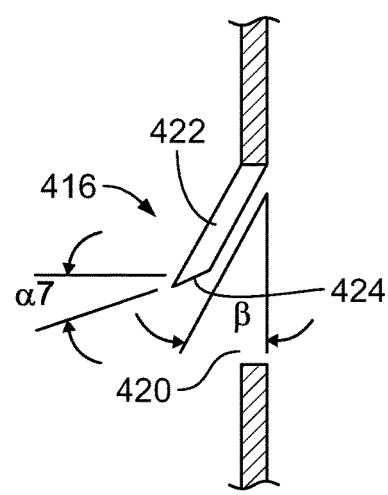
Figure 9A:
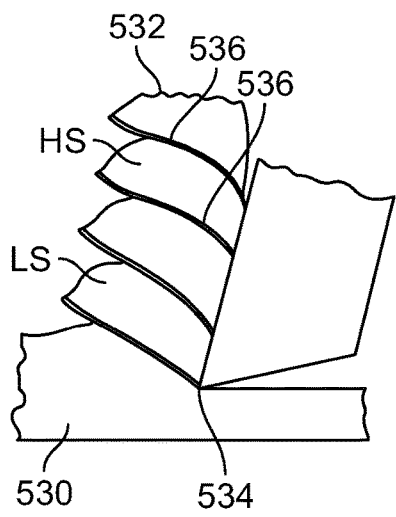
Figure 9B:
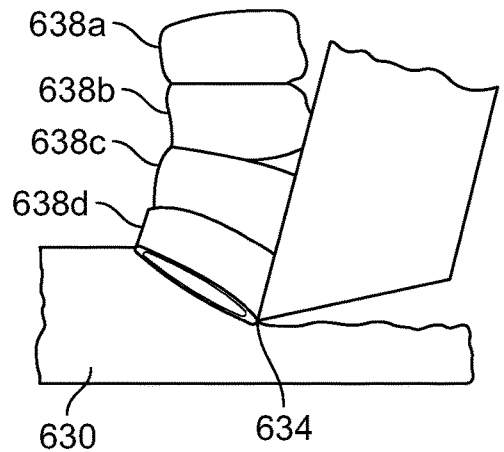
Figures 10A, 10B, 10C:
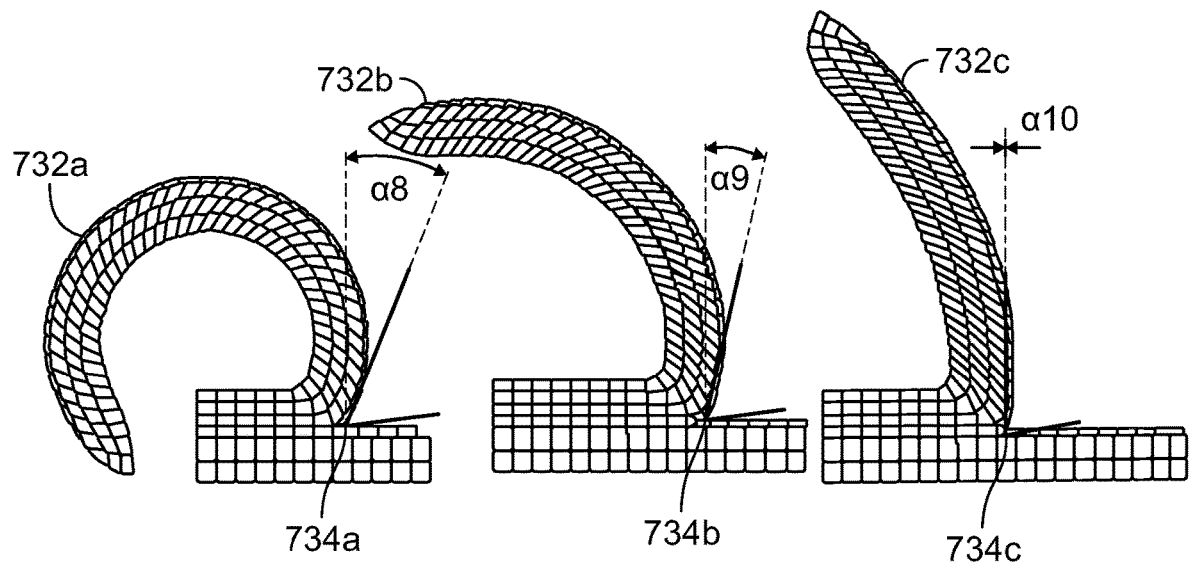
Figure 11A:
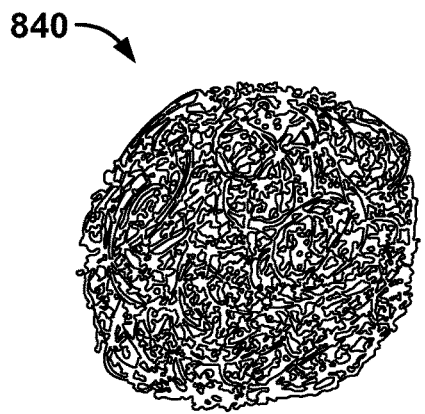
Figure 11B:
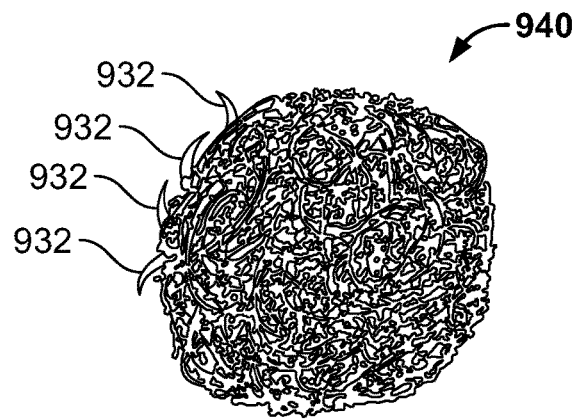
Figure 12A:
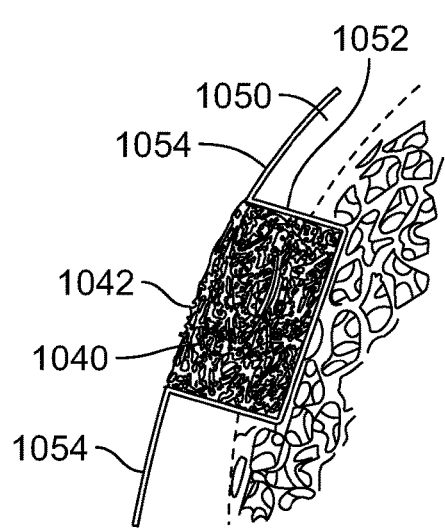
Figure 12B:
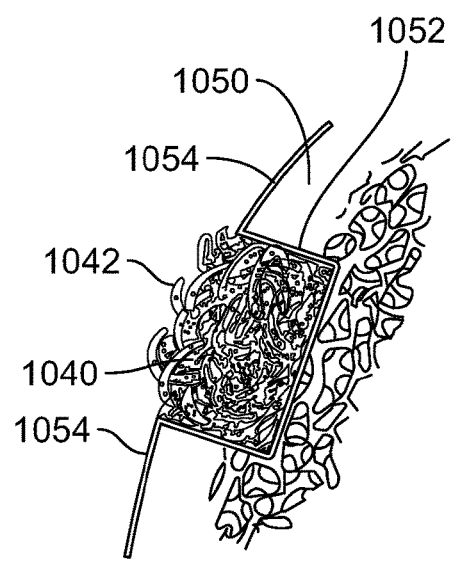

6D is a cross-sectional view of the modified cutting feature of FIG. 6C;

FIG. 7 is a series of cross-sectional views of a cutting feature similar to that of FIG. 6A, but having differently sized cutting angles;

FIG. 8A is a top view of another exemplary embodiment of a cutting feature of a grater suitable for use in an embodiment of the present invention FIG. 8B is a cross-sectional view of the cutting feature of FIG. 8A;

FIG. 9A is a schematic diagram showing the formation of a cartilage fiber having striations by a cutting edge;

FIG. 9B is a schematic diagram showing the formation of discontinuous pieces of cartilage by a cutting edge;

FIGS. 10A, 10B and 10C are a series of diagrams showing how cutting edges having smaller cutting angles will produce less curved cartilage fibers;

FIGS. 11A-11B are schematic diagrams showing an exemplary embodiment of a cartilage-derived implant in accordance with the present invention, with and without protruding cartilage fibers, respectively; and FIGS. 12A-12B are schematic diagrams showing the use of the cartilage-derived implant of FIG. 11A, where FIG. 12B shows swelling of the cartilage-derived implant upon rehydration.

DETAILED DESCRIPTION OF THE INVENTION

An embodiment of the present invention comprises a cartilage-derived implant including cartilage fibers. In an embodiment, the cartilage fibers include viable native chondrocytes. In an embodiment, the cartilage fibers are freeze-dried, and do not contain measurable amounts of viable chondrocytes. In an embodiment, the cartilage-derived implant includes cartilage fibers and cartilage particles. Embodiments of the present invention include methods for producing cartilage fibers from recovered cartilage, including without limitation one or more condyles. Embodiments of the present invention also include methods of making the aforementioned cartilage-derived implants. Embodiments of the present invention also include methods of using the aforesaid cartilage-derived implants for the repair of cartilage defects. Non-limiting exemplary embodiments of the cartilage-derived implants of the present invention, and methods of making and using same, are discussed herein.

The cartilage-derived implants of the present invention have uses in the repair of defects in articular cartilage, costal cartilage, or other types of cartilage in a patient. The cartilage-derived implants of the present invention have uses in meniscal repair, sternotomy repair, the repair of subchondral bone, the repair of articulating joints, and the repair or replacement of cartilaginous anatomical features, including, but not limited to, nasal and auricular cartilage.

In an embodiment of the present invention, the cartilage-derived implant is a scaffold for the delivery of growth-inductive factors. In an embodiment, the cartilage-derived implant is growth-inductive. In an embodiment, the cartilage-derived implant is a scaffold for the delivery of cells. In an embodiment, the cartilage-derived implant is a scaffold for the migration of cells. In an embodiment, the cartilage-derived implant is a growth-conductive medium for the in-growth of tissue. In an embodiment, the cartilage-derived implant is a tissuegenic matrix.

I. CARTILAGE FIBER IMPLANTS

Cartilage fibers according to some embodiments of the present invention are derived from cartilage which is allogeneic to the patient. In an embodiment, cartilage fibers are derived from cartilage which is autologous to the patient. In an embodiment, cartilage fibers are derived from cartilage which is xenogeneic to the patient. In an embodiment, the cartilage includes articular cartilage. In an embodiment, the cartilage includes costal cartilage. In an embodiment of a method of making such cartilage fibers, cartilage is recovered from deceased human donors, and the tissue is treated to reduce bioburden according to methods known in the art. In an embodiment, the donor is a mature adult human donor. In an embodiment, the donor is a mature adult human donor having an age in the range of 20 to 55 years. In an embodiment, the donor is a human donor having an age of less than 20 years. In an embodiment, the donor is a juvenile human donor. Methods of selecting, recovering, and treating cartilage are known in the art, and exemplary methods are disclosed in co-owned U.S. Pat. Nos. RE 42,208, RE 43,258, 8,292,968, 8,834,928, and 8,883,210, the disclosures of which are incorporated by reference herein.

In embodiments of the present invention, cartilage fibers are obtained by a dissection of the recovered cartilage so as to obtain fibers therefrom (e.g., by grating, scraping, slicing, or cutting) and collecting the fibers, as described in further detail hereinafter. The cartilage fibers are then stored in media. The cartilage fibers are cleaned by means of buffered saline rinses (e.g., phosphate buffered saline (PBS) solution) or other rinses that would remove or reduce the potential for antigenic reactions in a patient receiving the cartilage fibers. In an embodiment of the present invention, the cartilage fibers are cleaned by means that conserve the viability of chondrocytes within the cartilage fibers. The cartilage fibers may then be sieved or filtered to collect fibers having desirable dimensions for use in making the cartilage-derived implant.

In embodiments of the present invention, the cartilage fibers have lengths in the range of about 0.2 mm to about 50 mm. In an embodiment of the present invention, at least one of the cartilage fibers has a length in the range of about 0.2 mm to about 0.5 mm. In an embodiment of the present invention, at least one of the cartilage fibers has a length in the range of about 0.5 mm to about 1.0 mm. In an embodiment of the present invention, at least one of the cartilage fibers has a length in the range of about 1.0 mm to about 1.5 mm. In an embodiment of the present invention, at least one of the cartilage fibers has a length in the range of about 1.5 mm to about 2.0 mm. In an embodiment of the present invention, at least one of the cartilage fibers has a length in the range of about 2.0 mm to about 2.5 mm. In an embodiment of the present invention, at least one of the cartilage fibers has a length in the range of about 2.5 mm to about 3.0 mm. In an embodiment of the present invention, at least one of the cartilage fibers has a length in the range of about 3.0 mm to about 3.5 mm. In an embodiment of the present invention, at least one of the cartilage fibers has a length in the range of about 3.5 mm to about 4.0 mm. In an embodiment of the present invention, at least one of the cartilage fibers has a length in the range of about 4.0 mm to about 4.5 mm. In an embodiment of the present invention, at least one of the cartilage fibers has a length in the range of about 4.5 mm to about 5.0 mm. In an embodiment of the present invention, at least one of the cartilage fibers has a length in the range of about 5.0 mm to about 5.5 mm. In an embodiment of the present invention, at least one of the cartilage fibers has a length in the range of about 5.5 mm to about 6.0 mm. In an embodiment of the present invention, at least one of the cartilage fibers has a length in the range of about 6.0 mm to about 6.5 mm. In an embodiment of the present invention, at least one of the cartilage fibers has a length in the range of about 6.5 mm to about 7.0 mm. In an embodiment of the present invention, at least one of the cartilage fibers has a length in the range of about 7.0 mm to about 7.5 mm. In an embodiment of the present invention, at least one of the cartilage fibers has a length in the range of about 7.5 mm to about 8.0 mm. In an embodiment of the present invention, at least one of the cartilage fibers has a length in the range of about 8.0 mm to about 8.5 mm. In an embodiment of the present invention, at least one of the cartilage fibers has a length in the range of about 8.5 mm to about 9.0 mm. In an embodiment of the present invention, at least one of the cartilage fibers has a length in the range of about 9.0 mm to about 9.5 mm. In an embodiment of the present invention, at least one of the cartilage fibers has a length in the range of about 9.5 mm to about 10.0 mm. In an embodiment of the present invention, at least one of the cartilage fibers has a length in the range of about 10 mm to about 11 mm. In an embodiment of the present invention, at least one of the cartilage fibers has a length in the range of about 11 mm to about 12 mm. In an embodiment of the present invention, at least one of the cartilage fibers has a length in the range of about 12 mm to about 13 mm. In an embodiment of the present invention, at least one of the cartilage fibers has a length in the range of about 13 mm to about 14 mm. In an embodiment of the present invention, at least one of the cartilage fibers has a length in the range of about 14 mm to about 15 mm. In an embodiment of the present invention, at least one of the cartilage fibers has a length in the range of about 15 mm to about 16 mm. In an embodiment of the present invention, at least one of the cartilage fibers has a length in the range of about 16 mm to about 17 mm. In an embodiment of the present invention, at least one of the cartilage fibers has a length in the range of about 17 mm to about 18 mm. In an embodiment of the present invention, at least one of the cartilage fibers has a length in the range of about 18 mm to about 19 mm. In an embodiment of the present invention, at least one of the cartilage fibers has a length in the range of about 19 mm to about 20 mm. In an embodiment of the present invention, at least one of the cartilage fibers has a length in the range of about 20 mm to about 25 mm. In an embodiment of the present invention, at least one of the cartilage fibers has a length in the range of about 25 mm to about 30 mm. In an embodiment of the present invention, at least one of the cartilage fibers has a length in the range of about 30 mm to about 35 mm. In an embodiment of the present invention, at least one of the cartilage fibers has a length in the range of about 35 mm to about 40 mm. In an embodiment of the present invention, at least one of the cartilage fibers has a length in the range of about 40 mm to about 45 mm. In an embodiment of the present invention, at least one of the cartilage fibers has a length in the range of about 45 mm to about 50 mm.

In embodiments of the present invention, the cartilage fibers have an average length in the range of about 1 mm to about 20 mm. In an embodiment, the cartilage fibers have an average length of about 1 mm. In an embodiment, the cartilage fibers have an average length of about 2 mm. In an embodiment, the cartilage fibers have an average length of about 3 mm. In an embodiment, the cartilage fibers have an average length of about 4 mm. In an embodiment, the cartilage fibers have an average length of about 5 mm. In an embodiment, the cartilage fibers have an average length of about 6 mm. In an embodiment, the cartilage fibers have an average length of about 7 mm. In an embodiment, the cartilage fibers have an average length of about 8 mm. In an embodiment, the cartilage fibers have an average length of about 9 mm. In an embodiment, the cartilage fibers have an average length of about 10 mm. In an embodiment, the cartilage fibers have an average length of about 12 mm. In an embodiment, the cartilage fibers have an average length of about 14 mm. In an embodiment, the cartilage fibers have an average length of about 16 mm. In an embodiment, the cartilage fibers have an average length of about 18 mm. In an embodiment, the cartilage fibers have an average length of about 20 mm.

In an embodiment, the cartilage fibers have an average length of at least 1 mm. In an embodiment, the cartilage fibers have an average length of at least 2 mm. In an embodiment, the cartilage fibers have an average length of at least 3 mm. In an embodiment, the cartilage fibers have an average length of at least 4 mm. In an embodiment, the cartilage fibers have an average length of at least 5 mm. In an embodiment, the cartilage fibers have an average length of at least 6 mm. In an embodiment, the cartilage fibers have an average length of at least 7 mm. In an embodiment, the cartilage fibers have an average length of at least 8 mm. In an embodiment, the cartilage fibers have an average length of about at least 9 mm. In an embodiment, the cartilage fibers have an average length of at least 10 mm. In an embodiment, the cartilage fibers have an average length of at least 12 mm. In an embodiment, the cartilage fibers have an average length of at least 14 mm. In an embodiment, the cartilage fibers have an average length of at least 16 mm. In an embodiment, the cartilage fibers have an average length of at least 18 mm. In an embodiment, the cartilage fibers have an average length of at least 20 mm.

In an embodiment, the cartilage fibers have an average length in the range of about 1 mm to about 3 mm. In an embodiment, the cartilage fibers have an average length in the range of about 2 mm to about 4 mm. In an embodiment, the cartilage fibers have an average length in the range of about 3 mm to about 5 mm. In an embodiment, the cartilage fibers have an average length in the range of about 4 mm to about 6 mm. In an embodiment, the cartilage fibers have an average length in the range of about 5 mm to about 7 mm. In an embodiment, the cartilage fibers have an average length in the range of about 6 mm to about 8 mm. In an embodiment, the cartilage fibers have an average length in the range of about 7 mm to about 9 mm. In an embodiment, the cartilage fibers have an average length in the range of about 8 mm to about 10 mm. In an embodiment, the cartilage fibers have an average length in the range of about 9 mm to about 11 mm. In an embodiment, the cartilage fibers have an average length in the range of about 10 mm to about 12 mm. In an embodiment, the cartilage fibers have an average length in the range of about 12 mm to about 14 mm. In an embodiment, the cartilage fibers have an average length in the range of about 14 mm to about 16 mm. In an embodiment, the cartilage fibers have an average length in the range of about 16 mm to about 18 mm. In an embodiment, the cartilage fibers have an average length in the range of about 18 mm to about 20 mm.

In embodiments of the present invention, the cartilage fibers have widths or thicknesses in the range of about 0.01 mm to about 5 mm. In an embodiment of the present invention, at least one of the cartilage fibers has a width in the range of about 0.01 mm to about 0.05 mm. In an embodiment of the present invention, at least one of the cartilage fibers has a width in the range of about 0.05 mm to about 0.10 mm. In an embodiment of the present invention, at least one of the cartilage fibers has a width in the range of about 0.10 mm to about 0.15 mm. In an embodiment of the present invention, at least one of the cartilage fibers has a width in the range of about 0.15 mm to about 0.20 mm. In an embodiment of the present invention, at least one of the cartilage fibers has a width in the range of about 0.20 mm to about 0.25 mm. In an embodiment of the present invention, at least one of the cartilage fibers has a width in the range of about 0.25 mm to about 0.30 mm. In an embodiment of the present invention, at least one of the cartilage fibers has a width in the range of about 0.30 mm to about 0.35 mm. In an embodiment of the present invention, at least one of the cartilage fibers has a width in the range of about 0.35 mm to about 0.40 mm. In an embodiment of the present invention, at least one of the cartilage fibers has a width in the range of about 0.40 mm to about 0.45 mm. In an embodiment of the present invention, at least one of the cartilage fibers has a width in the range of about 0.45 mm to about 0.50 mm. In an embodiment of the present invention, at least one of the cartilage fibers has a width in the range of about 0.50 mm to about 0.55 mm. In an embodiment of the present invention, at least one of the cartilage fibers has a width in the range of about 0.55 mm to about 0.60 mm. In an embodiment of the present invention, at least one of the cartilage fibers has a width in the range of about 0.60 mm to about 0.65 mm. In an embodiment of the present invention, at least one of the cartilage fibers has a width in the range of about 0.65 mm to about 0.70 mm. In an embodiment of the present invention, at least one of the cartilage fibers has a width in the range of about 0.70 mm to about 0.75 mm. In an embodiment of the present invention, at least one of the cartilage fibers has a width in the range of about 0.75 mm to about 0.80 mm. In an embodiment of the present invention, at least one of the cartilage fibers has a width in the range of about 0.80 mm to about 0.85 mm. In an embodiment of the present invention, at least one of the cartilage fibers has a width in the range of about 0.85 mm to about 0.90 mm. In an embodiment of the present invention, at least one of the cartilage fibers has a width in the range of about 0.90 mm to about 0.95 mm. In an embodiment of the present invention, at least one of the cartilage fibers has a width in the range of about 0.95 mm to about 1.0 mm. In an embodiment of the present invention, at least one of the cartilage fibers has a width in the range of about 1.0 mm to about 1.1 mm. In an embodiment of the present invention, at least one of the cartilage fibers has a width in the range of about 1.1 mm to about 1.2 mm. In an embodiment of the present invention, at least one of the cartilage fibers has a width in the range of about 1.2 mm to about 1.3 mm. In an embodiment of the present invention, at least one of the cartilage fibers has a width in the range of about 1.3 mm to about 1.4 mm. In an embodiment of the present invention, at least one of the cartilage fibers has a width in the range of about 1.4 mm to about 1.5 mm. In an embodiment of the present invention, at least one of the cartilage fibers has a width in the range of about 1.5 mm to about 1.6 mm. In an embodiment of the present invention, at least one of the cartilage fibers has a width in the range of about 1.6 mm to about 1.7 mm. In an embodiment of the present invention, at least one of the cartilage fibers has a width in the range of about 1.7 mm to about 1.8 mm. In an embodiment of the present invention, at least one of the cartilage fibers has a width in the range of about 1.8 mm to about 1.9 mm. In an embodiment of the present invention, at least one of the cartilage fibers has a width in the range of about 1.9 mm to about 2.0 mm. In an embodiment of the present invention, at least one of the cartilage fibers has a width in the range of about 2.0 mm to about 2.5 mm. In an embodiment of the present invention, at least one of the cartilage fibers has a width in the range of about 2.5 mm to about 3.0 mm. In an embodiment of the present invention, at least one of the cartilage fibers has a width in the range of about 3.0 mm to about 3.5 mm. In an embodiment of the present invention, at least one of the cartilage fibers has a width in the range of about 3.5 mm to about 4.0 mm. In an embodiment of the present invention, at least one of the cartilage fibers has a width in the range of about 4.0 mm to about 4.5 mm. In an embodiment of the present invention, at least one of the cartilage fibers has a width in the range of about 4.5 mm to about 5.0 mm.

In embodiments of the present invention, the cartilage fibers have an average width in the range of about 0.1 mm to about 2 mm. In an embodiment, the cartilage fibers have an average width of about 0.1 mm. In an embodiment, the cartilage fibers have an average width of about 0.2 mm. In an embodiment, the cartilage fibers have an average width of about 0.3 mm. In an embodiment, the cartilage fibers have an average width of about 0.4 mm. In an embodiment, the cartilage fibers have an average width of about 0.5 mm. In an embodiment, the cartilage fibers have an average width of about 0.6 mm. In an embodiment, the cartilage fibers have an average width of about 0.7 mm. In an embodiment, the cartilage fibers have an average width of about 0.8 mm. In an embodiment, the cartilage fibers have an average width of about 0.9 mm. In an embodiment, the cartilage fibers have an average width of about 1.0 mm. In an embodiment, the cartilage fibers have an average width of about 1.2 mm. In an embodiment, the cartilage fibers have an average width of about 1.4 mm. In an embodiment, the cartilage fibers have an average width of about 1.6 mm. In an embodiment, the cartilage fibers have an average width of about 1.8 mm. In an embodiment, the cartilage fibers have an average width of about 2 mm.

In an embodiment, the cartilage fibers have an average width of at least 0.1 mm. In an embodiment, the cartilage fibers have an average width of at least 0.2 mm. In an embodiment, the cartilage fibers have an average width of at least 0.3 mm. In an embodiment, the cartilage fibers have an average width of at least 0.4 mm. In an embodiment, the cartilage fibers have an average width of at least 0.5 mm. In an embodiment, the cartilage fibers have an average width of at least 0.6 mm. In an embodiment, the cartilage fibers have an average width of at least 0.7 mm. In an embodiment, the cartilage fibers have an average width of at least 0.8 mm. In an embodiment, the cartilage fibers have an average width of at least 0.9 mm. In an embodiment, the cartilage fibers have an average width of at least 1.0 mm. In an embodiment, the cartilage fibers have an average width of at least 1.2 mm. In an embodiment, the cartilage fibers have an average width of at least 1.4 mm. In an embodiment, the cartilage fibers have an average width of at least 1.6 mm. In an embodiment, the cartilage fibers have an average width of at least 1.8 mm. In an embodiment, the cartilage fibers have an average width of at least 2.0 mm.

In an embodiment, the cartilage fibers have an average width in the range of about 0.1 mm to about 0.3 mm. In an embodiment, the cartilage fibers have an average width in the range of about 0.2 mm to about 0.4 mm. In an embodiment, the cartilage fibers have an average width in the range of about 0.3 mm to about 0.5 mm. In an embodiment, the cartilage fibers have an average width in the range of about 0.4 mm to about 0.6 mm. In an embodiment, the cartilage fibers have an average width in the range of about 0.5 mm to about 0.7 mm. In an embodiment, the cartilage fibers have an average width in the range of about 0.6 mm to about 0.8 mm. In an embodiment, the cartilage fibers have an average width in the range of about 0.7 mm to about 0.9 mm. In an embodiment, the cartilage fibers have an average width in the range of about 0.8 mm to about 1.0 mm. In an embodiment, the cartilage fibers have an average width in the range of about 0.9 mm to about 1.1 mm. In an embodiment, the cartilage fibers have an average width in the range of about 1.0 mm to about 1.2 mm. In an embodiment, the cartilage fibers have an average width in the range of about 1.2 mm to about 1.4 mm. In an embodiment, the cartilage fibers have an average width in the range of about 1.4 mm to about 1.6 mm. In an embodiment, the cartilage fibers have an average width in the range of about 1.6 mm to about 1.8 mm. In an embodiment, the cartilage fibers have an average width in the range of about 1.8 mm to about 2.0 mm.

In embodiments of the present invention, the cartilage fibers have individual volumes in the range of about 0.1 $mm^3$ to about 200 $mm^3$. In an embodiment, at least one of the cartilage fibers has a volume in the range of about 0.1 $mm^3$ to about 0.5 $mm^3$. In an embodiment, at least one of the cartilage fibers has a volume in the range of about 0.5 $mm^3$ to about 1.0 $mm^3$. In an embodiment, at least one of the cartilage fibers has a volume in the range of about 1.0 $mm^3$ to about 1.2 $mm^3$. In an embodiment, at least one of the cartilage fibers has a volume in the range of about 1.2 $mm^3$ to about 1.4 $mm^3$. In an embodiment, at least one of the cartilage fibers has a volume in the range of about 1.4 $mm^3$ to about 1.6 $mm^3$. In an embodiment, at least one of the cartilage fibers has a volume in the range of about 1.6 $mm^3$ to about 1.8 $mm^3$. In an embodiment, at least one of the cartilage fibers has a volume in the range of about 1.8 $mm^3$ to about 2.0 $mm^3$. In an embodiment, at least one of the cartilage fibers has a volume in the range of about 2.0 $mm^3$ to about 2.2 $mm^3$. In an embodiment, at least one of the cartilage fibers has a volume in the range of about 2.2 $mm^3$ to about 2.4 $mm^3$. In an embodiment, at least one of the cartilage fibers has a volume in the range of about 2.4 $mm^3$ to about 2.6 $mm^3$. In an embodiment, at least one of the cartilage fibers has a volume in the range of about 2.6 $mm^3$ to about 2.8 $mm^3$. In an embodiment, at least one of the cartilage fibers has a volume in the range of about 2.8 $mm^3$ to about 3.0 $mm^3$. In an embodiment, at least one of the cartilage fibers has a volume in the range of about 3.0 $mm^3$ to about 3.2 $mm^3$. In an embodiment, at least one of the cartilage fibers has a volume in the range of about 3.2 $mm^3$ to about 3.4 $mm^3$. In an embodiment, at least one of the cartilage fibers has a volume in the range of about 3.4 $mm^3$ to about 3.6 $mm^3$. In an embodiment, at least one of the cartilage fibers has a volume in the range of about 3.6 $mm^3$ to about 3.8 $mm^3$. In an embodiment, at least one of the cartilage fibers has a volume in the range of about 3.8 $mm^3$ to about 4.0 $mm^3$. In an embodiment, at least one of the cartilage fibers has a volume in the range of about 4.0 $mm^3$ to about 4.2 $mm^3$. In an embodiment, at least one of the cartilage fibers has a volume in the range of about 4.2 $mm^3$ to about 4.4 $mm^3$. In an embodiment, at least one of the cartilage fibers has a volume in the range of about 4.4 $mm^3$ to about 4.6 $mm^3$. In an embodiment, at least one of the cartilage fibers has a volume in the range of about 4.6 $mm^3$ to about 4.8 $mm^3$. In an embodiment, at least one of the cartilage fibers has a volume in the range of about 4.8 $mm^3$ to about 5.0 $mm^3$. In an embodiment, at least one of the cartilage fibers has a volume in the range of about 5.0 $mm^3$ to about 5.5 $mm^3$. In an embodiment, at least one of the cartilage fibers has a volume in the range of about 5.5 $mm^3$ to about 6.0 $mm^3$. In an embodiment, at least one of the cartilage fibers has a volume in the range of about 6.0 $mm^3$ to about 6.5 $mm^3$. In an embodiment, at least one of the cartilage fibers has a volume in the range of about 6.5 $mm^3$ to about 7.0 $mm^3$. In an embodiment, at least one of the cartilage fibers has a volume in the range of about 7.0 $mm^3$ to about 7.5 $mm^3$. In an embodiment, at least one of the cartilage fibers has a volume in the range of about 7.5 $mm^3$ to about 8.0 $mm^3$. In an embodiment, at least one of the cartilage fibers has a volume in the range of about 8.0 $mm^3$ to about 8.5 $mm^3$. In an embodiment, at least one of the cartilage fibers has a volume in the range of about 8.5 $mm^3$ to about 9.0 $mm^3$. In an embodiment, at least one of the cartilage fibers has a volume in the range of about 9.5 $mm^3$ to about 10 $mm^3$. In an embodiment, at least one of the cartilage fibers has a volume in the range of about 10 $mm^3$ to about 12 $mm^3$. In an embodiment, at least one of the cartilage fibers has a volume in the range of about 12 $mm^3$ to about 14 $mm^3$. In an embodiment, at least one of the cartilage fibers has a volume in the range of about 14 $mm^3$ to about 16 $mm^3$. In an embodiment, at least one of the cartilage fibers has a volume in the range of about 16 $mm^3$ to about 18 $mm^3$. In an embodiment, at least one of the cartilage fibers has a volume in the range of about 18 $mm^3$ to about 20 $mm^3$. In an embodiment, at least one of the cartilage fibers has a volume in the range of about 20 $mm^3$ to about 25 $mm^3$. In an embodiment, at least one of the cartilage fibers has a volume in the range of about 25 $mm^3$ to about 30 $mm^3$. In an embodiment, at least one of the cartilage fibers has a volume in the range of about 30 $mm^3$ to about 35 $mm^3$. In an embodiment, at least one of the cartilage fibers has a volume in the range of about 35 $mm^3$ to about 40 $mm^3$. In an embodiment, at least one of the cartilage fibers has a volume in the range of about 40 mm³ to about 45 mm³. In an embodiment, at least one of the cartilage fibers has a volume in the range of about 45 mm³ to about 50 mm³. In an embodiment, at least one of the cartilage fibers has a volume in the range of about 50 mm³ to about 60 mm³. In an embodiment, at least one of the cartilage fibers has a volume in the range of about 60 mm³ to about 70 mm³. In an embodiment, at least one of the cartilage fibers has a volume in the range of about 70 mm³ to about 80 mm³. In an embodiment, at least one of the cartilage fibers has a volume in the range of about 80 mm³ to about 90 mm³. In an embodiment, at least one of the cartilage fibers has a volume in the range of about 90 mm³ to about 100 mm³. In an embodiment, at least one of the cartilage fibers has a volume in the range of about 100 mm³ to about 120 mm³. In an embodiment, at least one of the cartilage fibers has a volume in the range of about 120 mm³ to about 140 mm³. In an embodiment, at least one of the cartilage fibers has a volume in the range of about 140 mm³ to about 160 mm³. In an embodiment, at least one of the cartilage fibers has a volume in the range of about 160 mm³ to about 180 mm³. In an embodiment, at least one of the cartilage fibers has a volume in the range of about 180 mm³ to about 200 mm³.

In embodiments of the present invention, the cartilage fibers have an average volume in the range of about 1 mm³ to about 20 mm³. In an embodiment, the cartilage fibers have an average volume of about 1 mm³. In an embodiment, the cartilage fibers have an average volume of about 1.2 mm³. In an embodiment, the cartilage fibers have an average volume of about 1.4 mm³. In an embodiment, the cartilage fibers have an average volume of about 1.6 mm³. In an embodiment, the cartilage fibers have an average volume of about 1.8 mm³. In an embodiment, the cartilage fibers have an average volume of about 2.0 mm³. In an embodiment, the cartilage fibers have an average volume of about 2.2 mm³. In an embodiment, the cartilage fibers have an average volume of about 2.4 mm³. In an embodiment, the cartilage fibers have an average volume of about 2.6 mm³. In an embodiment, the cartilage fibers have an average volume of about 2.8 mm³. In an embodiment, the cartilage fibers have an average volume of about 3.0 mm³. In an embodiment, the cartilage fibers have an average volume of about 3.2 mm³. In an embodiment, the cartilage fibers have an average volume of about 3.4 mm³. In an embodiment, the cartilage fibers have an average volume of about 3.6 mm³. In an embodiment, the cartilage fibers have an average volume of about 3.8 mm³. In an embodiment, the cartilage fibers have an average volume of about 4.0 mm³. In an embodiment, the cartilage fibers have an average volume of about 4.5 mm³. In an embodiment, the cartilage fibers have an average volume of about 5.0 mm³. In an embodiment, the cartilage fibers have an average volume of about 5.5 mm³. In an embodiment, the cartilage fibers have an average volume of about 6.0 mm³. In an embodiment, the cartilage fibers have an average volume of about 6.5 mm³. In an embodiment, the cartilage fibers have an average volume of about 7.0 mm³. In an embodiment, the cartilage fibers have an average volume of about 7.5 mm³. In an embodiment, the cartilage fibers have an average volume of about 8.0 mm³. In an embodiment, the cartilage fibers have an average volume of about 8.5 mm³. In an embodiment, the cartilage fibers have an average volume of about 9.0 mm³. In an embodiment, the cartilage fibers have an average volume of about 9.5 mm³. In an embodiment, the cartilage fibers have an average volume of about 10 mm³. In an embodiment, the cartilage fibers have an average volume of about 12 mm³. In an embodiment, the cartilage fibers have an average volume of about 14 mm³. In an embodiment, the cartilage fibers have an average volume of about 16 mm³. In an embodiment, the cartilage fibers have an average volume of about 18 mm³. In an embodiment, the cartilage fibers have an average volume of about 20 mm³.

In an embodiment, the cartilage fibers have an average volume of at least 1 mm³. In an embodiment, the cartilage fibers have an average volume of at least 1.2 mm³. In an embodiment, the cartilage fibers have an average volume of at least 1.4 mm³. In an embodiment, the cartilage fibers have an average volume of at least 1.6 mm³. In an embodiment, the cartilage fibers have an average volume of at least 1.8 mm³. In an embodiment, the cartilage fibers have an average volume of at least 2.0 mm³. In an embodiment, the cartilage fibers have an average volume of at least 2.2 mm³. In an embodiment, the cartilage fibers have an average volume of at least 2.4 mm³. In an embodiment, the cartilage fibers have an average volume of at least 2.6 mm³. In an embodiment, the cartilage fibers have an average volume of at least 2.8 mm³. In an embodiment, the cartilage fibers have an average volume of at least 3.0 mm³. In an embodiment, the cartilage fibers have an average volume of at least 3.2 mm³. In an embodiment, the cartilage fibers have an average volume of at least 3.4 mm³. In an embodiment, the cartilage fibers have an average volume of at least 3.6 mm³. In an embodiment, the cartilage fibers have an average volume of at least 3.8 mm³. In an embodiment, the cartilage fibers have an average volume of at least 4.0 mm³. In an embodiment, the cartilage fibers have an average volume of at least 4.5 mm³. In an embodiment, the cartilage fibers have an average volume of at least 5.0 mm³. In an embodiment, the cartilage fibers have an average volume of at least 5.5 mm³. In an embodiment, the cartilage fibers have an average volume of at least 6.0 mm³. In an embodiment, the cartilage fibers have an average volume of at least 6.5 mm³. In an embodiment, the cartilage fibers have an average volume of at least 7.0 mm³. In an embodiment, the cartilage fibers have an average volume of at least 7.5 mm³. In an embodiment, the cartilage fibers have an average volume of at least 8.0 mm³. In an embodiment, the cartilage fibers have an average volume of at least 8.5 mm³. In an embodiment, the cartilage fibers have an average volume of at least 9.0 mm³. In an embodiment, the cartilage fibers have an average volume of at least 9.5 mm³. In an embodiment, the cartilage fibers have an average volume of at least 10 mm³. In an embodiment, the cartilage fibers have an average volume of at least 12 mm³. In an embodiment, the cartilage fibers have an average volume of at least 14 mm³. In an embodiment, the cartilage fibers have an average volume of at least 16 mm³. In an embodiment, the cartilage fibers have an average volume of at least 18 mm³. In an embodiment, the cartilage fibers have an average volume of at least 20 mm³.

In an embodiment, the cartilage fibers have an average volume in the range of about 1 mm³ to about 1.4 mm³. In an embodiment, the cartilage fibers have an average volume in the range of about 1.2 mm³ to about 1.6 mm³. In an embodiment, the cartilage fibers have an average volume in the range of about 1.4 mm³ to about 1.8 mm³. In an embodiment, the cartilage fibers have an average volume in the range of about 1.6 mm³ to about 2.0 mm³. In an embodiment, the cartilage fibers have an average volume in the range of about 1.8 mm³ to about 2.2 mm³. In an embodiment, the cartilage fibers have an average volume in the range of about 2.0 mm³ to about 2.4 mm³. In an embodiment, the cartilage fibers have an average volume in the range of about 2.2 mm³ to about 2.6 mm³. In an embodiment, the cartilage fibers have an average volume in the range of about 2.4 mm$^3$ to about 2.8 mm$^3$. In an embodiment, the cartilage fibers have an average volume in the range of about 2.6 mm$^3$ to about 3.0 mm$^3$. In an embodiment, the cartilage fibers have an average volume in the range of about 2.8 mm$^3$ to about 3.2 mm$^3$. In an embodiment, the cartilage fibers have an average volume in the range of about 3.0 mm$^3$ to about 3.4 mm$^3$. In an embodiment, the cartilage fibers have an average volume in the range of about 3.2 mm$^3$ to about 3.6 mm$^3$. In an embodiment, the cartilage fibers have an average volume in the range of about 3.4 mm$^3$ to about 3.8 mm$^3$. In an embodiment, the cartilage fibers have an average volume in the range of about 3.6 mm$^3$ to about 4.0 mm$^3$. In an embodiment, the cartilage fibers have an average volume in the range of about 3.8 mm$^3$ to about 4.2 mm$^3$. In an embodiment, the cartilage fibers have an average volume in the range of about 4.0 mm$^3$ to about 4.4 mm$^3$. In an embodiment, the cartilage fibers have an average volume in the range of about 4.2 mm$^3$ to about 5.0 mm$^3$. In an embodiment, the cartilage fibers have an average volume in the range of about 4.5 mm$^3$ to about 5.5 mm$^3$. In an embodiment, the cartilage fibers have an average volume in the range of about 5.0 mm$^3$ to about 6.0 mm$^3$. In an embodiment, the cartilage fibers have an average volume in the range of about 5.5 mm$^3$ to about 6.5 mm$^3$. In an embodiment, the cartilage fibers have an average volume in the range of about 6.0 mm$^3$ to about 7.0 mm$^3$. In an embodiment, the cartilage fibers have an average volume in the range of about 6.5 mm$^3$ to about 7.5 mm$^3$. In an embodiment, the cartilage fibers have an average volume in the range of about 7.0 mm$^3$ to about 8.0 mm$^3$. In an embodiment, the cartilage fibers have an average volume in the range of about 7.5 mm$^3$ to about 9.5 mm$^3$. In an embodiment, the cartilage fibers have an average volume in the range of about 8.0 mm$^3$ to about 10.0 mm$^3$. In an embodiment, the cartilage fibers have an average volume in the range of about 8.5 mm$^3$ to about 10.5 mm$^3$. In an embodiment, the cartilage fibers have an average volume in the range of about 9.0 mm$^3$ to about 11.0 mm$^3$. In an embodiment, the cartilage fibers have an average volume in the range of about 9.5 mm$^3$ to about 11.5 mm$^3$. In an embodiment, the cartilage fibers have an average volume in the range of about 10 mm$^3$ to about 14 mm$^3$. In an embodiment, the cartilage fibers have an average volume in the range of about 12 mm$^3$ to about 16 mm$^3$. In an embodiment, the cartilage fibers have an average volume in the range of about 14 mm$^3$ to about 18 mm$^3$. In an embodiment, the cartilage fibers have an average volume in the range of about 16 mm$^3$ to about 20 mm$^3$.

In embodiments of the present invention, at least some of the cartilage fibers have an aspect ratio (length/width) in the range of about 1:1 to about 50:1. In an embodiment, at least some of the cartilage fibers have an aspect ratio in the range of about 1:1 to about 2:1. In an embodiment, at least some of the cartilage fibers have an aspect ratio in the range of about 2:1 to about 3:1. In an embodiment, at least some of the cartilage fibers have an aspect ratio in the range of about 3:1 to about 4:1. In an embodiment, at least some of the cartilage fibers have an aspect ratio in the range of about 4:1 to about 5:1. In an embodiment, at least some of the cartilage fibers have an aspect ratio in the range of about 5:1 to about 6:1. In an embodiment, at least some of the cartilage fibers have an aspect ratio in the range of about 6:1 to about 7:1. In an embodiment, at least some of the cartilage fibers have an aspect ratio in the range of about 7:1 to about 8:1. In an embodiment, at least some of the cartilage fibers have an aspect ratio in the range of about 8:1 to about 9:1. In an embodiment, at least some of the cartilage fibers have an aspect ratio in the range of about 9:1 to about 10:1. In an embodiment, at least some of the cartilage fibers have an aspect ratio in the range of about 10:1 to about 12:1. In an embodiment, at least some of the cartilage fibers have an aspect ratio in the range of about 12:1 to about 14:1. In an embodiment, at least some of the cartilage fibers have an aspect ratio in the range of about 14:1 to about 16:1. In an embodiment, at least some of the cartilage fibers have an aspect ratio in the range of about 16:1 to about 18:1. In an embodiment, at least some of the cartilage fibers have an aspect ratio in the range of about 18:1 to about 20:1. In an embodiment, at least some of the cartilage fibers have an aspect ratio in the range of about 20:1 to about 25:1. In an embodiment, at least some of the cartilage fibers have an aspect ratio in the range of about 25:1 to about 30:1. In an embodiment, at least some of the cartilage fibers have an aspect ratio in the range of about 30:1 to about 35:1. In an embodiment, at least some of the cartilage fibers have an aspect ratio in the range of about 35:1 to about 40:1. In an embodiment, at least some of the cartilage fibers have an aspect ratio in the range of about 40:1 to about 45:1. In an embodiment, at least some of the cartilage fibers have an aspect ratio in the range of about 45:1 to about 50:1.

In an embodiment, at least some of the cartilage fibers have an aspect ratio of at least 1:1. In an embodiment, at least some of the cartilage fibers have an aspect ratio of at least 2:1. In an embodiment, at least some of the cartilage fibers have an aspect ratio of at least 3:1. In an embodiment, at least some of the cartilage fibers have an aspect ratio of at least 4:1. In an embodiment, at least some of the cartilage fibers have an aspect ratio of at least 5:1. In an embodiment, at least some of the cartilage fibers have an aspect ratio of at least 6:1. In an embodiment, at least some of the cartilage fibers have an aspect ratio of at least 7:1. In an embodiment, at least some of the cartilage fibers have an aspect ratio of at least 8:1. In an embodiment, at least some of the cartilage fibers have an aspect ratio of at least 9:1. In an embodiment, at least some of the cartilage fibers have an aspect ratio of at least 10:1. In an embodiment, at least some of the cartilage fibers have an aspect ratio of at least 12:1. In an embodiment, at least some of the cartilage fibers have an aspect ratio of at least 14:1. In an embodiment, at least some of the cartilage fibers have an aspect ratio of at least 16:1. In an embodiment, at least some of the cartilage fibers have an aspect ratio of at least 18:1. In an embodiment, at least some of the cartilage fibers have an aspect ratio of at least 20:1. In an embodiment, at least some of the cartilage fibers have an aspect ratio of at least 30:1. In an embodiment, at least some of the cartilage fibers have an aspect ratio of at least 35:1. In an embodiment, at least some of the cartilage fibers have an aspect ratio of at least 40:1. In an embodiment, at least some of the cartilage fibers have an aspect ratio of at least 45:1.

In an embodiment of the present invention, at least some of the cartilage fibers are ribbon-like, having, for example, a width/thickness ratio in the range of about 10:1 to about 500:1. In an embodiment, at least some of the ribbon-like cartilage fibers have a width/thickness ratio in the range of about 10:1 to about 20:1. In an embodiment, at least some of the ribbon-like cartilage fibers have a width/thickness ratio in the range of about 20:1 to about 40:1. In an embodiment, at least some of the ribbon-like cartilage fibers have a width/thickness ratio in the range of about 40:1 to about 60:1. In an embodiment, at least some of the ribbon-like cartilage fibers have a width/thickness ratio in the range of about 60:1 to about 80:1. In an embodiment, at least some of the ribbon-like cartilage fibers have a width/thickness ratio in the range of about 80:1 to about 100:1. In an embodiment, at least some of the ribbon-like cartilage fibers have a width/thickness ratio in the range of about 100:1 to about 150:1. In an embodiment, at least some of the ribbon-like cartilage fibers have a width/thickness ratio in the range of about 150:1 to about 200:1. In an embodiment, at least some of the ribbon-like cartilage fibers have a width/thickness ratio in the range of about 200:1 to about 250:1. In an embodiment, at least some of the ribbon-like cartilage fibers have a width/thickness ratio in the range of about 250:1 to about 300:1. In an embodiment, at least some of the ribbon-like cartilage fibers have a width/thickness ratio in the range of about 300:1 to about 350:1. In an embodiment, at least some of the ribbon-like cartilage fibers have a width/thickness ratio in the range of about 350:1 to about 400:1. In an embodiment, at least some of the ribbon-like cartilage fibers have a width/thickness ratio in the range of about 450:1 to about 500:1.

In an embodiment of the present invention, at least some of the cartilage fibers are ribbon-like, having, for example, a width/thickness ratio in the range of about 10:1 to about 500:1. In an embodiment, at least some of the ribbon-like cartilage fibers have a width/thickness ratio of at least 10:1. In an embodiment, at least some of the ribbon-like cartilage fibers have a width/thickness ratio of at least 20:1. In an embodiment, at least some of the ribbon-like cartilage fibers have a width/thickness ratio of at least 40:1. In an embodiment, at least some of the ribbon-like cartilage fibers have a width/thickness ratio of at least 60:1. In an embodiment, at least some of the ribbon-like cartilage fibers have a width/thickness ratio of at least 80:1. In an embodiment, at least some of the ribbon-like cartilage fibers have a width/thickness ratio of at least 100:1. In an embodiment, at least some of the ribbon-like cartilage fibers have a width/thickness ratio of at least 150:1. In an embodiment, at least some of the ribbon-like cartilage fibers have a width/thickness ratio of at least 200:1. In an embodiment, at least some of the ribbon-like cartilage fibers have a width/thickness ratio of at least 250:1. In an embodiment, at least some of the ribbon-like cartilage fibers have a width/thickness ratio of at least 300:1. In an embodiment, at least some of the ribbon-like cartilage fibers have a width/thickness ratio of at least 350:1. In an embodiment, at least some of the ribbon-like cartilage fibers have a width/thickness ratio of at least 450:1.

In an embodiment of the present invention, at least some of the cartilage fibers are thread-like, having, for example, a width/thickness ratio in the range of about 1:1 to about 10:1. In an embodiment, at least some of the thread-like cartilage fibers have a width/thickness ratio in the range of about 1:1 to about 2:1. In an embodiment, at least some of the thread-like cartilage fibers have a width/thickness ratio in the range of about 2:1 to about 3:1. In an embodiment, at least some of the thread-like cartilage fibers have a width/thickness ratio in the range of about 3:1 to about 4:1. In an embodiment, at least some of the thread-like cartilage fibers have a width/thickness ratio in the range of about 4:1 to about 5:1. In an embodiment, at least some of the thread-like cartilage fibers have a width/thickness ratio in the range of about 5:1 to about 6:1. In an embodiment, at least some of the thread-like cartilage fibers have a width/thickness ratio in the range of about 6:1 to about 7:1. In an embodiment, at least some of the thread-like cartilage fibers have a width/thickness ratio in the range of about 7:1 to about 8:1. In an embodiment, at least some of the thread-like cartilage fibers have a width/thickness ratio in the range of about 8:1 to about 9:1. In an embodiment, at least some of the thread-like cartilage fibers have a width/thickness ratio in the range of about 9:1 to about 10:1.

In an embodiment, at least some of the thread-like cartilage fibers have a width/thickness ratio of at least 1:1. In an embodiment, at least some of the thread-like cartilage fibers have a width/thickness ratio of at least 2:1. In an embodiment, at least some of the thread-like cartilage fibers have a width/thickness ratio of at least 3:1. In an embodiment, at least some of the thread-like cartilage fibers have a width/thickness ratio of at least 4:1. In an embodiment, at least some of the thread-like cartilage fibers have a width/thickness ratio of at least 5:1. In an embodiment, at least some of the thread-like cartilage fibers have a width/thickness ratio of at least 6:1. In an embodiment, at least some of the thread-like cartilage fibers have a width/thickness ratio of at least 7:1. In an embodiment, at least some of the thread-like cartilage fibers have a width/thickness ratio of at least 8:1. In an embodiment, at least some of the thread-like cartilage fibers have a width/thickness ratio of at least 9:1. In an embodiment, at least some of the thread-like cartilage fibers have a width/thickness ratio of at least 10:1.

In embodiments of the present invention, the cartilage fibers may have cross-sections of virtually any shape. In an embodiment, at least some of the cartilage fibers have cross-sectional shapes that are similar to each other. In an embodiment, at least some of the cartilage fibers have a cross-sectional shape having at least one straight edge. In an embodiment, at least some of the cartilage fibers have a cross-sectional shape having at least two straight edges. In an embodiment, at least some of the cartilage fibers have a cross-sectional shape having at least two straight edges that intersect each other at an angle. In an embodiment, at least some of the cartilage fibers have a polygonal cross-sectional shape. In an embodiment, at least some of the cartilage fibers have a cross-sectional shape with at least one curved edge. In an embodiment, at least some of the cartilage fibers have a semi-circular cross-sectional shape. In an embodiment, at least some of the cartilage fibers have a semi-elliptical cross-sectional shape. In an embodiment, at least some of the cartilage fibers have a circular cross-sectional shape. In an embodiment, at least some of the cartilage fibers have a crescent cross-sectional shape. In an embodiment, at least some of the cartilage fibers have an irregular cross-sectional shape.

In an embodiment, at least some of the cartilage fibers are similar to each other in their respective dimensions. In an embodiment, at least some of the cartilage fibers are a mixture of ribbon-like and thread-like cartilage fibers. In an embodiment, at least some of the cartilage fibers have selected dimensions and/or cross-sectional shapes. In an embodiment, the cartilage fibers have various lengths. In an embodiment, the cartilage fibers have various widths and thicknesses. In an embodiment, some of the cartilage fibers have long lengths and some of the cartilage fibers have short lengths. In an embodiment, at least some of the cartilage fibers have one cross-sectional shape and at least some of the cartilage fibers have a different cross-sectional shape. In an embodiment, the dimensions and/or cross-sectional shape of a cartilage fiber are generated by the tool selected to perform the blunt dissection of the recovered cartilage.

In an embodiment, the cartilage fibers are substantially free of cells and their components. In an embodiment, the cartilage fibers include viable native cells. In an embodiment, the cartilage fibers include non-viable native cells. Non-viable native cells may, for example without limitation, be present in the cartilage fibers when the cartilage fibers are produced from recovered cartilage that has been frozen. In an embodiment, the cartilage fibers include viable non-native cells. In an embodiment, the cartilage fibers include non-native non-viable cells. Cartilage fibers may, for example without limitation, include non-native cells (viable or non-viable) when they have been added or cultured on the cartilage fibers after production of the cartilage fibers. Native and non-native cells include, without limitation, chondrocytes and other types of cells.

In an embodiment, the cartilage fibers are in the form of a mass of cartilage fibers, which are then used to prepare implants that may be used to fill a cartilage defect in a patient. Such implants may be used as a standalone treatment device or be applied in combination with one or more of a variety of bioactive materials or cells that facilitate the reconstruction and healing of cartilage. The cartilage fibers serve as a matrix or scaffold for the remodeling of chondral tissue, resulting in the growth of new cartilage or of collagen fibrous material that fills spaces in the defect. Remodeling occurs along the edges of the fibers, which provide a greater number of remodeling sites relative to the number provided by other types of cartilage pieces.

In an embodiment, the cartilage fibers are manipulated to form a putty without adding a carrier or other biologically-compatible material. In an embodiment, the cartilage fibers are combined with a carrier or other biologically-compatible material to form a paste, putty or gel. In an embodiment, the cartilage fibers are combined with a carrier or other biologically-compatible material such that the resulting mixture may be injected into a cartilage defect site in a patient. In an embodiment, the paste, putty, gel, or injectable mixture is used to fill a defect site, or are otherwise applied to a defect site or to a site of a diseased or defective cartilage, or to other tissues in a patient in need of such a paste, putty, gel, or injectable mixture.

In an embodiment, suitable carriers for forming a putty or an injectable mixture include, but are not necessarily limited to, the following: an aqueous buffer, an isotonic solution; a sodium chloride solution at a concentration of about 0.1% to about 1%, more particularly, about 0.9%; a lactated Ringer's solution, with or without D5LR (dextrose); phosphate buffered saline ("PBS"); platelet rich plasma (PRP); glycerin; lecithin; alginate; hyaluronic acid (HA); a derivative of HA; or sodium hyaluronate; or other suitable carriers known in the art. The carrier may also comprise "biological components" added to the carrier, such as, but not limited to, DNA, RNA, short hairpin RNA (shRNA), small interfering RNA (siRNA), micro RNA (mRNA), polysaccharides, peptides, matrix proteins, glycosaminoglycans (e.g, hyaluronic acid), viral vectors, and liposomes. The carrier further should maintain the stability and bioavailability of an active agent, if such an active agent is added to the carrier. Biologically-compatible materials that are suitable for combination with the cartilage fibers include, but are not necessarily limited to, bone marrow aspirate (BMA), platelet rich plasma (PRP), growth factors, blood, synovial fluid, fibrin glue, and acellular bulking agents derived from soft tissues such as fascia, adipose tissue, placental tissues, or other soft tissues. In an embodiment, exogenous viable cells are added to the cartilage fibers, or to the putty, paste, gel, or injectable mixture. Such exogenous viable cells may include, but are not necessarily limited to, autologous or allogeneic chondrocytes, autologous cells such as those obtained from the patient's bone marrow or stromal vascular fraction (SVF); allogeneic cells such as those obtained from a cell bank (e.g., stem cells, progenitor cells or other cell types available from cell banks), or bone marrow and bone marrow components including bone marrow cells (both autologous and allogeneic).

II. PRODUCING CARTILAGE FIBERS

As already mentioned, methods for preparing cartilage fibers suitable for use in producing cartilage-derived implants as described and contemplated herein include separating cartilage fibers by mechanical techniques selected from grating, scraping, slicing, cutting, or combinations thereof, from recovered cartilage, such as without limitation one or more condyles. The grating, scraping, slicing or cutting of the recovered cartilage may be performed using any suitable tools or devices, known now or in the future, that are capable of separating cartilage fibers from the recovered cartilage that have the desired dimensions and shapes. In some embodiments, for example without limitation, a grater is used to prepare the cartilage fibers from recovered cartilage held in a vice. As grating proceeds, the position of the recovered cartilage in the vice may be changed so as to allow the grater better access to the cartilage without bumping against the vice. Such graters are commercially available from various sources for performing the desired grating operation, including: Kitchen Aid of Benton Harbor, Mich., U.S.A.; Oxo located Chambersburg, Pa., U.S.A.; Microplane of McAllen, Tex., U.S.A.; Chen, a division of Taylor Precision Products located in Las Cruces, N. Mex., U.S.A.; and Cuisinart of East Windsor, N.J., U.S.A. In some embodiments, commercially available graters are modified to perform the desired grating operation. In some embodiments, the graters are custom designed and fabricated to perform the desired grating operation. The characteristics (e.g., size, shape, degree of pliability or stiffness, degree of curling, quantity of viable chondrocytes, etc.) of cartilage fibers appear to be related to the type of grater used, as well as the characteristics of the cutting features of the grater, as will be discussed in further detail hereinafter.

Different techniques may be employed to form the cutting features of graters such as, without limitation, die stamping, acid etching, microplaning, laser etching, and electroforming, regardless of the type of grater. Applicants have surprisingly discovered that differences in cutting feature forming techniques affect certain characteristics of the resulting cartilage fibers. For example, Applicants have surprisingly discovered that cartilage fibers prepared using a grater having cutting features formed by die stamping techniques are rougher and have more striations, are more curled, more pliable, and swell less upon hydration. Similarly, Applicants have surprisingly found that cartilage fibers prepared using a grater having cutting features formed by acid etching techniques are smoother (fewer or no striations), less curled, more stiff (less pliable), and swell more upon hydration. Additionally, Applicants have surprisingly found that cartilage fibers prepared using a grater having cutting features formed by acid etching techniques have a greater quantity of viable chondrocytes, while cartilage fibers prepared using a grater having cutting features formed by die stamping techniques have a fewer viable chondrocytes. While cartilage fibers produced with acid etched cutting features are easier to cut and contain more viable chondrocytes, they also swell more upon rehydration. It is preferred, when the fibers are formed into an implant and implanted in a cartilage defect, that the implant remains substantially flush with the native surface of the cartilage having the defect. "Substantially flush" as used herein means that the implant swells less than 2 millimeters beyond or above the native surface of the cartilage having the defect after the implant is implanted therein. Cartilage fibers produced with die stamping techniques have better handling characteristics, but fewer viable chondrocytes. Thus, persons of ordinary skill in the art will recognize that selection and balancing among the various possible characteristics of cartilage fibers is possible and may be advantageous when selecting the type of cutting tool to use.

Figure 4:
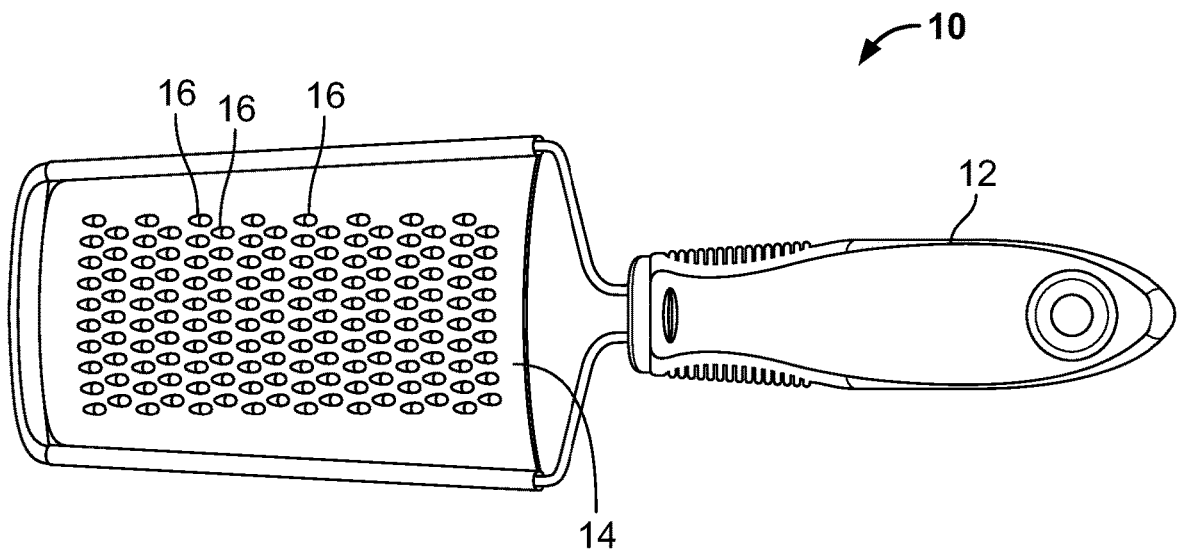
FIG. 4 is a top view of a planar grater suitable for use in an embodiment of the present invention.
Figure 5:
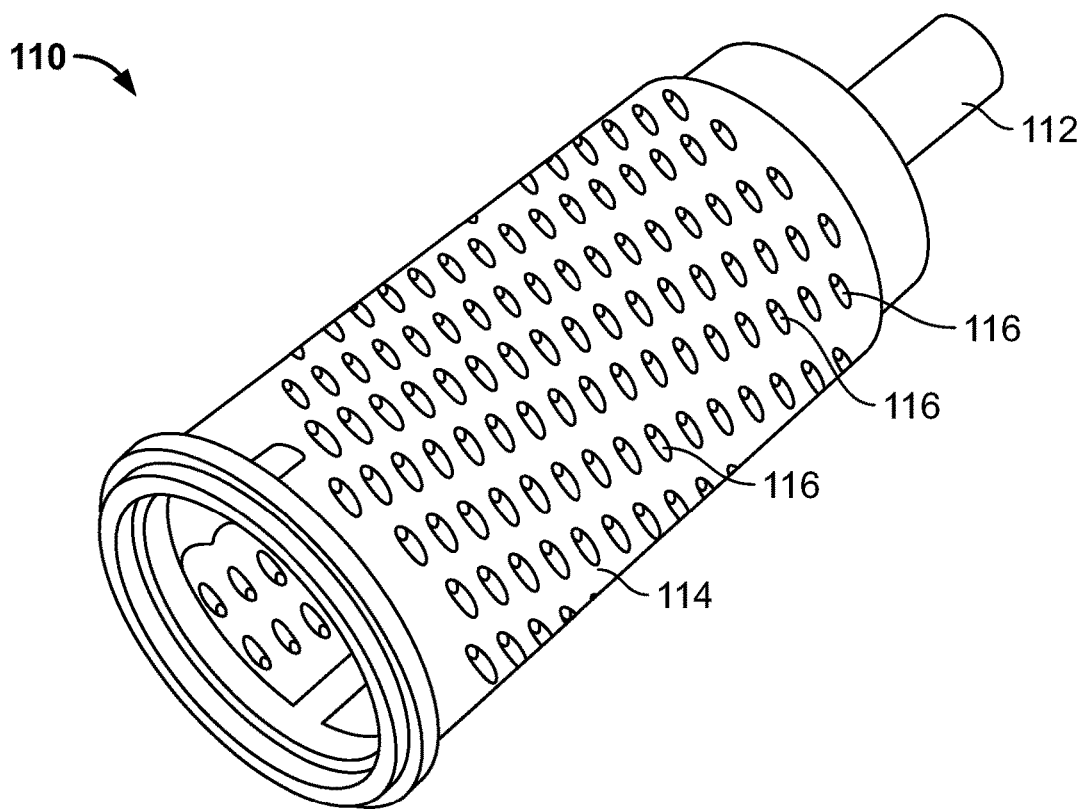
FIG. 5 is a perspective view of a rotary grater suitable for use in an embodiment of the present invention.

FIGS. 4 and 5 show two exemplary types of graters suitable for performing the methods for preparing cartilage fibers described and contemplated herein. FIG. 4 shows the top view of a planar grater 10 having a handle 12, a convex planar body 14, and a plurality of cutting features 16 on the planar body 14. Another type of grater, i.e., a rotary grater 110, is shown in FIG. 5 having a handle 112 adapted for connection with a drill device (not shown) and a cylindrical body 114 with a plurality of cutting features 116 on the cylindrical body 114. As easily determinable by persons of ordinary skill in the art, other types of graters are also suitable for preparing cartilage fibers from recovered cartilage according to the methods described and contemplated herein. The cutting features 16, 116 shown on the graters 10, 110 of FIGS. 4 and 5 were formed by a die stamping technique, which is common and well-known in the industry of grater manufacture. However, the cutting features could have been made by any technique known now or in the future, such as those mentioned above. Applicants have surprisingly found that using a rotary type of grater produces cartilage fibers having a more consistent fiber length compared to cartilage fibers produced using a planar grater.

With reference now to FIGS. 6A and 6B, FIG. 6A shows a perspective view of an individual cutting feature 16 and FIG. 6B shows a front cross-sectional view of that cutting feature 16 taken along line I-I and looking in the direction of the arrows. Each individual cutting feature 16 has a configuration which includes an opening 20 and a raised cutting surface 22 with a cutting edge 24. As shown, the cutting surface 22 and cutting edge 24 of this cutting feature 16 have a curved or arced shape, which produces cartilage fibers having a commensurately sized fiber thickness.

Figure 6D:
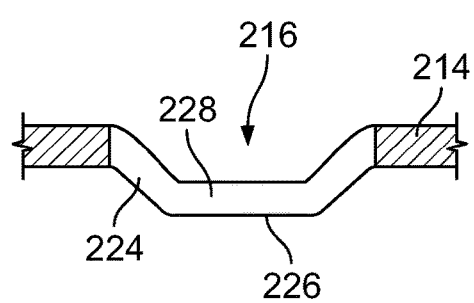

Applicants have also explored modifications to the cutting features 216 to create modified cutting surfaces 222 and cutting edges 224, as shown for example in FIGS. 6C and 6D, in which the cutting surface 222 has a flattened portion 226. FIG. 6D shows a front cross-sectional view of the cutting feature 216 of FIG. 6C taken along line III-III and looking in the direction of the arrows. As shown in FIG. 6D, the cutting edge 224 of such modified cutting features 216 also has a flattened portion 228 which produces cartilage fibers having a commensurately smaller sized fiber thickness than those produced with the unmodified cutting features 16. Although not shown per se, other modifications may be made to the cutting features 16 such as making the cutting surface 22 smaller, which in turn makes the opening 20 larger and the cutting edge 24 shorter and less curved, which produced cartilage fibers having a commensurately smaller sized fiber thickness than those produced with the unmodified cutting features 16.

With reference to FIG. 7, Applicants also explored modifications to the cutting edge 324 of cutting features 316 whereby cutting angles ($\alpha 1$, $\alpha 2$, $\alpha 3$, $\alpha 4$, $\alpha 5$, $\alpha 6$) of different sizes are created on the cutting edge 324. Various cutting angle sizes were created and investigated. FIG. 7 shows a series of lateral cross-sectional views (#1, #2, #3, #4, #5, #6) of a cutting feature 316, of the type shown in FIG. 6A, taken along line II-II and looking in the direction of the arrows. As shown, the cutting edges 324 of various cutting features 316 were modified to have cutting angles ($\alpha 1$, $\alpha 2$, $\alpha 3$, $\alpha 4$, $\alpha 5$, $\alpha 6$) of various sizes. More particularly, in one embodiment (#1), the cutting edge 24 has a cutting angle $\alpha 1$ of $-20°$. In another embodiment (#2), the cutting edge 24 has a cutting angle $\alpha 2$ of $-5°$. In another embodiment (#3), the cutting edge 24 has a cutting angle $\alpha 3$ of $-35°$. In another embodiment (#4), the cutting edge 24 has a cutting angle $\alpha 4$ of $0°$. In another embodiment (#5), the cutting edge 24 has a cutting angle $\alpha 5$ of $10°$. In another embodiment (#6), the cutting edge 24 has a cutting angle $\alpha 6$ of $20°$. Of course, as will be recognized by persons of ordinary skill in the art, the exemplary embodiments shown in FIG. 7 are not the only possible configurations, and cutting angles ($\alpha 1$, $\alpha 2$, $\alpha 3$, $\alpha 4$, $\alpha 5$, $\alpha 6$) of other sizes are possible and suitable for use in the methods described and contemplated herein.

With reference now to FIGS. 8A-8B, other configurations of cutting features 416 are possible. FIG. 8A shows a top plan view of a cutting feature 416 having an alternative configuration and FIG. 8B shows a front cross-sectional view of the cutting feature 216 of FIG. 6C taken along line IV-IV and looking in the direction of the arrows. More particularly, in some embodiments, individual cutting features 416 each comprise an opening 420 with a planar cutting surface, such as a blade 422, and a linear cutting edge 424 on the blade 422. For cutting features such as these 416, the size of the blade angle $\beta$ may be varied, which will commensurately change the size of the cartilage fibers produced. For example, a cutting feature 416 having a smaller blade angle $\beta$ is expected to produce cartilage fibers having a smaller fiber thickness than a cutting feature 416 having a larger blade angle $\beta$. Additionally, the cutting angle $\alpha 7$ of these cutting features 416 may be modified to be any one of various sizes, in the manner of the modifications to the cutting angle ($\alpha 1$, $\alpha 2$, $\alpha 3$, $\alpha 4$, $\alpha 5$, $\alpha 6$) of the cutting features 316 described above in connection with FIG. 7.

It has been discovered that aspects of the cutting process have an effect on how curled the resulting cartilage fibers become during production. It is important, for example, to keep the recovered cartilage moist during production of cartilage fibers using cutting tools. With reference to FIG. 9A, when the recovered cartilage 530 is kept moist during the fiber production process by periodic or continuous addition of water or another biocompatible solvent or solution, including but not limited to saline or buffered saline, the cartilage fibers 532 produced using a cutting tool (not shown) with a cutting edge 534 will be continuous or semi-continuous, often with striations 536 and curled, as shown in FIG. 9A. During the cutting of the cartilage fiber 532 from the recovered cartilage 530 by the action of the cutting edge 534 of the cutting tool, a high shear strain zone HS is created in the fiber 532 first, followed by a low shear strain zone LS. As shown in FIG. 9B, if the recovered cartilage 630 is too dry, discontinuous cartilage pieces 638a, 638b, 638c, 638d will likely be created by the action of the cutting edge 634. Also, as shown in FIGS. 10A, 10B and 10C, the smaller the cutting angle $\alpha 8$, $\alpha 9$, $\alpha 10$ of the cutting edge 734a, 734b, 734c, respectively, of the cutting tool (not shown), the less curled the cartilage fibers 732a, 732b, 732c will be. Continuous or semi-continuous cartilage fibers 532 having striations 536 and being curled are generally preferred over discontinuous pieces and cartilage fibers that are more curled are generally preferred over less curled ones, for reasons discussed below in connection with formation of implants comprising the cartilage fibers.

As mentioned previously, the cartilage fibers are generally in the form of a mass of cartilage fibers which is then manipulated, with or without carrier or other biologically-compatible material, into a paste, putty, or gel that may then be used to fill a cartilage defect in a patient. For example, a mass of cartilage fibers may be manipulated into a more cohesive cartilage-derived implant 840, such as shown in FIG. 11A Such a cartilage-derived implant 840 behaves like a paste, putty, or gel in that it is deformable to different shapes, but the fibers remain intertwined with one another and cohesive, so the cartilage-derived implant can be applied to a defect site or to a site of diseased or defective cartilage without coming apart or falling out of the defect. It is preferred that after manipulation to form the cartilage-derived implant, no cartilage fibers protrude from the surface of the implant. For example, FIG. 11B shows a cartilage-derived implant 940 having cartilage fibers 932 undesirably protruding from its surface. A smooth and substantially homogenous surface is most beneficial for the cartilage-derived implants (as shown in FIG. 11A). It has been surprisingly found by Applicants that cartilage fibers that have striations and are curled perform better in this respect to form a cartilage-derived implant without fibers protruding from its surface.

FIG. 12A provides a schematic side cross-sectional view of cartilage 1050 having a defect 1052 which has been filled with a cartilage-derived implant 1040 according to the methods described and contemplated herein. Generally the implant 1040 is pushed into the defect until its outward facing surface 1042 is flush or level with the native surface 1054 of the healthy or undamaged portion cartilage 1050. If the implant is thereafter hydrated either by exposure to biological fluids of the patient or purposeful addition of fluids by a surgeon or other user of the implant 1040, the implant 1040 may swell, as shown in FIG. 12B, and the outward facing surface 1042 of the implant 1040 may undesirably protrude from the native surface 1054 of the cartilage 1050. Thus, the swelling of the implant 1040 after rehydration is generally not preferred. As mentioned above, Applicants have determined that cartilage fibers produced using a grater having cutting features formed by die stamping techniques have better handling characteristics, including more curling and having striations, which features are believed to minimize the protrusion of individual cartilage fibers from the surface of a cartilage-derived implant comprising such fibers.

III. CARTILAGE FIBERS HAVING VIABLE CELLS

Figure 1:
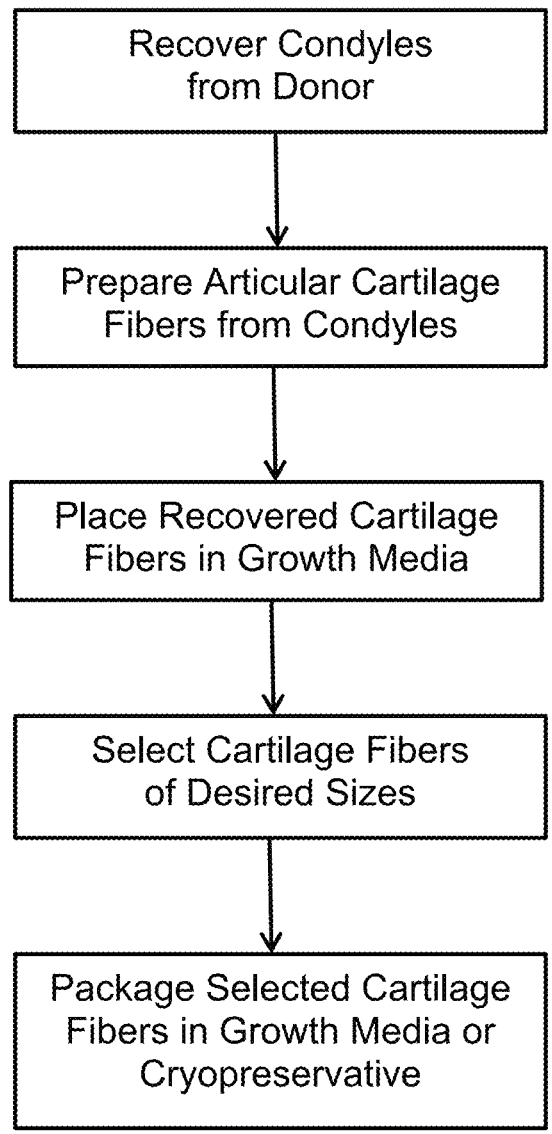
FIG. 1 is a block diagram of a process for preparing cartilage fibers having viable native chondrocytes, according to an embodiment of the present invention.

In an embodiment of the present invention, the aforementioned dissection of the recovered cartilage to produce cartilage fibers is performed so as to preserve viable cells within the cartilage fibers (hereinafter referred to as "fresh cartilage fibers"). For example, in an embodiment of the present invention, a cutting tool having cutting features formed by acid etching techniques is used to produce cartilage fibers having viable cells. In an embodiment, about 90-100% of the cells in the fresh cartilage fibers are viable. Fresh cartilage fibers are those which include viable cells and have not been subjected to lyophilizing or freezing. The fresh cartilage fibers may then be used in the operating room to prepare a cartilage-derived implant, or packaged in such a way that the viability of the cells in the cartilage fibers is maintained. The packaged fibers may then be recovered for use in a cartilage-derived implant, as described elsewhere herein. In an embodiment, more than 50% of the cells in the recovered fresh cartilage fibers are viable. In an embodiment, about 50% to about 70% of the cells in the recovered fresh cartilage fibers are viable. In an embodiment, more than 85% of the cells in the recovered fresh cartilage fibers are viable. In an embodiment, about 85% to about 95% of the cells in the recovered fresh cartilage fibers are viable. FIG. 1 is a block diagram of steps in a process for preparing fresh cartilage fibers, which may be understood with reference to Sections I and II of the present disclosure.

Turning to methods of packaging and storing the fresh cartilage fibers, various conditions are possible. For example, in an embodiment, fresh cartilage fibers may be stored in a growth media or other media that is suitable for maintaining the viability of the cells within the fresh cartilage fibers. In an embodiment, the fresh cartilage fibers are stored with a serum. In an embodiment, the fresh cartilage fibers are stored without a serum. In an embodiment, the fresh cartilage fibers are stored at room temperature, such as from about 15° C. to about 30° C. In an embodiment, the fresh cartilage fibers are stored at a refrigeration temperature, such as from about 2° C. to less than 15° C., such as, without limitation, from about 4° C. to about 10° C. In an embodiment, the fresh cartilage fibers are stored for a period of time from about 1 hour to less than about 7 days. In an embodiment, the fresh cartilage fibers are stored for a period of time from about 7 days to about 3 months. In an embodiment, the fresh cartilage fibers are stored for a period of time from greater than about 3 months to about 6 months. In an embodiment, the fresh cartilage fibers are stored for a period of time from greater than about 6 months to about 9 months. In an embodiment, the fresh cartilage fibers are stored for a period of time from greater than about 9 months to about 12 months. In an embodiment, the fresh cartilage fibers are stored for a period of time greater than about 12 months.

In an embodiment, the fresh cartilage fibers are stored under cryogenic conditions. In an embodiment, cryogenic conditions are achieved using controlled-rate freezing. In an embodiment, cryogenic conditions are achieved using freezing at an un-controlled rate. In an embodiment, the fresh cartilage fibers are stored under cryogenic conditions in at least one cryopreservative. In an embodiment, the at least one cryopreservative is a solution. According to an embodiment, the cryopreservative is dimethylsulfoxide (DMSO). According to an embodiment, the cryopreservative is basal media solution comprising about 5% DMSO. According to an embodiment, the cryopreservative is basal media solution comprising about 10% DMSO. According to an embodiment, the cryopreservative is basal media solution comprising about 15% DMSO. According to an embodiment, the cryopreservative is fetal bovine serum comprising about 5% DMSO. According to an embodiment, the cryopreservative is fetal bovine serum comprising about 10% DMSO. According to an embodiment, the cryopreservative is a human serum comprising about 15% DMSO. According to an embodiment, the cryopreservative is human serum comprising about 5% DMSO. According to an embodiment, the cryopreservative is human serum comprising about 10% DMSO. According to an embodiment, the cryopreservative includes ethylene glycol. According to an embodiment, the cryopreservative includes propylene glycol. According to an embodiment, the cryopreservative includes glycerol. In an embodiment, the cryopreservative is another cryopreservative known in the art for maintaining the viability of cells at cryogenic or other subfreezing temperatures (i.e., a temperature below 0° C. or below). In an embodiment, the fresh cartilage fibers are cooled to a subfreezing temperature. In an embodiment, the fresh cartilage fibers are stored cryogenically at the temperature of liquid nitrogen (e.g., at a temperature of about −196 C). In an embodiment, the fresh cartilage fibers are stored cryogenically at a temperature in the range of about −20° C. to about −90° C.

The packaged fresh cartilage fibers may be recovered according to methods that preserve the viability of the cells in the fresh cartilage fibers and are appropriate to the media in which they are stored. In an embodiment, the packaged fresh cartilage fibers are brought to room temperature in the media. In an embodiment, the frozen or cryogenically-preserved fresh cartilage fibers and the media are thawed. In an embodiment, the fresh cartilage fibers are separated from the media by sedimentation. In an embodiment, the fresh cartilage fibers are separated from the media by centrifugation. In an embodiment, the fresh cartilage fibers are separated from the media by decantation. In an embodiment, the fresh cartilage fibers are separated from the media by filtration. In an embodiment, the fresh cartilage fibers are separated from the media by gravity filtration. In an embodiment, the fresh cartilage fibers are separated from the media by vacuum filtration. In an embodiment, the fresh cartilage fibers are separated from the media by capturing the fresh cartilage fibers in a sieve.

In an embodiment, the separated fresh cartilage fibers are rinsed to remove media from the fibers. In an embodiment, the separated fresh cartilage fibers are rinsed with a liquid. In an embodiment, the liquid comprises a physiological saline solution. In an embodiment, the liquid comprises a buffered isotonic solution. In an embodiment, the physiological saline solution is a phosphate-buffered saline (PBS) solution. In an embodiment, the fresh cartilage fibers are rinsed at a temperature in the range from about 4° C. to about 10° C. In an embodiment, the fresh cartilage fibers are rinsed at a temperature in the range from about 10° C. to about 20° C. In an embodiment, the fresh cartilage fibers are rinsed at a temperature in the range from about 20° C. to about 30° C. In an embodiment, the fresh cartilage fibers are rinsed at a temperature in the range from about 30° C. to about 45° C. In an embodiment, the fresh cartilage fibers are rinsed at a temperature of about 25° C. In an embodiment, the fresh cartilage fibers are rinsed at an ambient temperature. In an embodiment, the fresh cartilage fibers are rinsed at body temperature (i.e., from about 35° C. to about 45° C.).

IV. DEHYDRATED OR LYOPHILIZED CARTILAGE FIBERS

In an embodiment of the present invention, the fresh cartilage fibers are dehydrated or lyophilized before being packaged or used. In an embodiment, dehydration or lyophilization devitalizes the cartilage fibers (i.e., viable cells are removed or killed). In an embodiment, the dehydrated or lyophilized cartilage fibers have an amount of residual moisture that maintains the integrity of the tissue, but does not permit biological activity.

In an embodiment, the fresh cartilage fibers are dehydrated without being frozen. In an embodiment, the fresh cartilage fibers are air-dried. In an embodiment, the fresh cartilage fibers are dehydrated under vacuum. In an embodiment, the fresh cartilage fibers are dehydrated at a temperature in the range from about 4° C. to about 10° C. In an embodiment, the fresh cartilage fibers are dehydrated at a temperature in the range from about 10° C. to about 20° C. In an embodiment, the fresh cartilage fibers are dehydrated at a temperature in the range from about of about 20° C. to about 30° C. In an embodiment, the fresh cartilage fibers are dehydrated at a temperature of about 25° C. In an embodiment, the fresh cartilage fibers are dehydrated at a temperature that is no greater than 35° C. In an embodiment, the fresh cartilage fibers are dehydrated at a temperature that is no greater than 40° C. In an embodiment, the fresh cartilage fibers are dehydrated at a temperature that is no greater than 50° C. In an embodiment, the fresh cartilage fibers are dehydrated at an ambient temperature. In an embodiment, the fresh cartilage fibers are dehydrated at body temperature (i.e., from about 35° C. to about 45° C.). In an embodiment, the dehydrated cartilage fibers have residual moisture in the range of about 0% to about 20%. In an embodiment, the dehydrated cartilage fibers have residual moisture in the range of about 6% to about 15%.

In an embodiment, the fresh cartilage fibers are dried in a frozen state (i.e., "freeze-dried" or "lyophilized"). Lyophilization methods suitable for use in the present invention are those known now or in the future to persons of ordinary skill in the relevant art. In an embodiment, the lyophilized cartilage fibers have residual moisture of about 6% or less, such as about 5% or less, or about 4% or less, or about 3% or less, by weight based on the total weight of the lyophilized cartilage fibers.

In an embodiment, the dehydrated or lyophilized cartilage fibers are packaged in a container without the addition of other materials. In an embodiment, the dehydrated or lyophilized cartilage fibers are stored at a temperature in the range from about 2° C. to about 15° C., such as, without limitation, from about 4° C. to about 10° C. In an embodiment, the dehydrated or lyophilized cartilage fibers are stored at an ambient temperature.

In an embodiment, the dehydrated or lyophilized cartilage fibers are rehydrated, then manipulated to form a putty without adding a carrier or other biologically-compatible material. In an embodiment, the dehydrated or lyophilized cartilage fibers are rehydrated using a rehydration solution known in the art. In an embodiment, the dehydrated or lyophilized cartilage fibers are rehydrated with a biologically compatible buffer solution. In an embodiment, the dehydrated or lyophilized cartilage fibers are rehydrated with PBS. In an embodiment, the dehydrated or lyophilized cartilage fibers are rehydrated with Ringer solution. In an embodiment, the rehydration solution includes a preservative, which may include, but is not necessarily limited to, mannitol, ascorbic acid, and glucose.

V. IMPLANTS COMPRISING CARTILAGE FIBERS AND CARTILAGE PARTICLES

Figure 2:
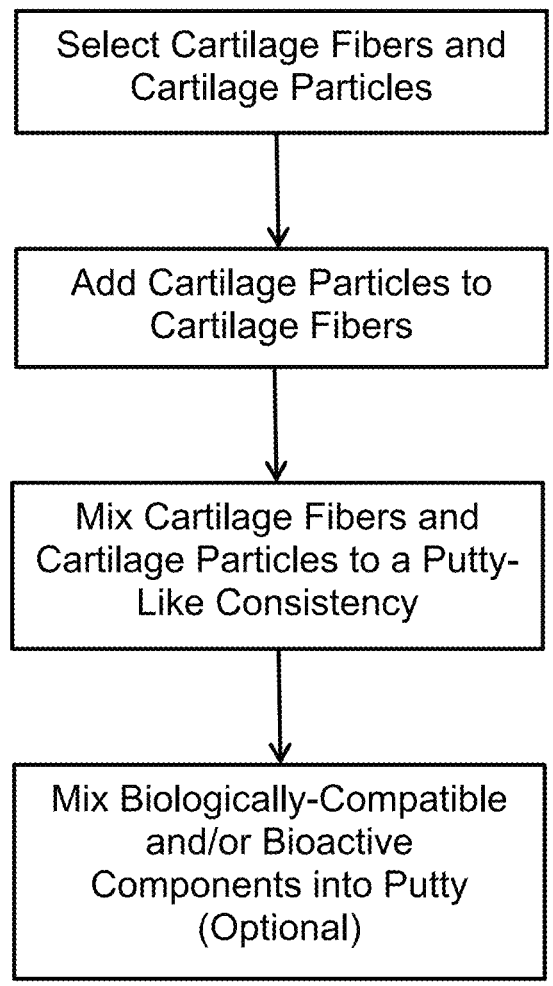
FIG. 2 is a block diagram of a process for preparing a cartilage-derived implant having viable native chondrocytes.

In an embodiment of the present invention, a cartilage-derived implant includes both cartilage fibers and cartilage particles. In an embodiment, the cartilage fibers are fresh cartilage fibers, as described in Section III above. In an embodiment, the cartilage fibers are dehydrated, lyophilized, or rehydrated cartilage fibers, as described in Section IV above. FIG. 2 is a block diagram of steps in a method of preparing a cartilage-derived implant from fresh cartilage fibers and lyophilized cartilage particles, which may be understood in conjunction with FIGS. 1 and 3 and Sections I, II, III and IV of the present disclosure. In an embodiment, the cartilage fibers and the cartilage particles are from the same donor. In an embodiment, the cartilage fibers and the cartilage particles are from different donors. In an embodiment, the cartilage fibers and the cartilage particles are from the same species. In an embodiment, the cartilage fibers and the cartilage particles are from different species. In an embodiment, the cartilage fibers and the cartilage particles are from the same species but the recipient is a different species.

In an embodiment of the present invention, the cartilage particles are derived from articular cartilage recovered from a human donor. In an embodiment, the cartilage particles are derived from meniscal cartilage recovered from a human donor. In an embodiment, the cartilage particles are derived from costal cartilage recovered from a human donor. In an embodiment, the cartilage particles are derived from hyaline cartilage recovered from a human donor. In an embodiment, the cartilage particles are derived from other cartilage recovered from a human donor. In an embodiment, the donor is a mature adult human donor having an age in the range of 20 to 55 years. In an embodiment, the donor is a human donor having an age of less than 20 years. In an embodiment, the donor is a juvenile human donor.

Figure 3:
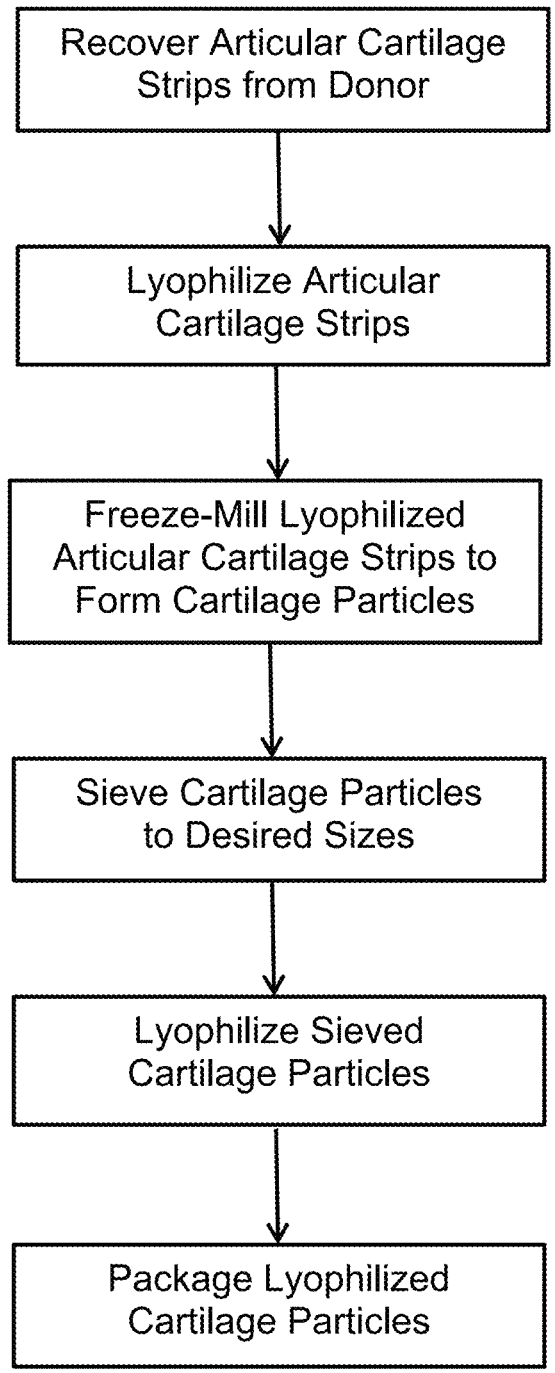
FIG. 3 is a block diagram of a process for preparing cartilage particles, according to an embodiment of the present invention.

FIG. 3 is a block diagram of steps in a method of preparing cartilage particles useful in the present invention. Additional methods of selecting, recovering, and treating cartilage are known in the art, and exemplary methods are disclosed in co-owned U.S. Pat. Nos. RE 42,208, RE 43,258, 8,292,968, 8,834,928, and 8,883,210, the disclosures of which are incorporated by reference herein. Methods of reducing cartilage to particulate form are also known in the art, and exemplary methods are disclosed in the aforesaid patents. Additionally, methods for making and using cartilage particles are also disclosed in U.S. Patent Application Publication Nos. 2006/0210643, 2008/0133008, 2011/0070271 and 2011/0196508, each of which is hereby incorporated herein.

In an embodiment of the present invention, the cartilage particles include viable cells (hereinafter, "fresh cartilage particles"). In an embodiment, the cartilage particles are dehydrated cartilage particles having residual moisture in the range of about 6% to about 15%. In an embodiment, the cartilage particles are lyophilized cartilage particles having residual moisture of about 6% or less.

In an embodiment of the present invention, the cartilage particles have sizes in the range of 212 µm and less. In an embodiment, the cartilage particles have sizes in the range of 500 µm and less. In an embodiment, the cartilage particles have sizes in the range of about 50 µm to about 212 µm.

In an embodiment of the present invention, the cartilage-derived implant comprises only cartilage fibers and no cartilage particles (i.e., a fiber:particle ratio of about 100/0 (w/w)). In an embodiment, the cartilage-derived implant comprises cartilage fibers and cartilage particles in a ratio of about 95/5 (w/w), a ratio of about 90/10 (w/w), a ratio of about 85/15 (w/w), a ratio of about 80/20 (w/w), a ratio of about 75/25 (w/w), a ratio of about 70/30 (w/w), a ratio of about 65/35 (w/w), a ratio of about 60/40 (w/w), a ratio of about 55/45 (w/w), a ratio of about 50/50 (w/w), a ratio of about 45/55 (w/w), a ratio of about 40/60 (w/w), a ratio of about 35/65 (w/w), a ratio of about 30/70 (w/w), a ratio of about 25/75 (w/w), a ratio of about 20/80 (w/w), a ratio of about 15/85 (w/w), a ratio of about 10/90 (w/w), a ratio of about 5/95 (w/w), or at some other ratio between 100/0 (w/w) and less 0/100 (w/w), where the w/w ratio is the ratio of the weight of the cartilage fibers to the weight of the cartilage particles.

In an embodiment of the present invention, the cartilage-derived implant consists of cartilage fibers and cartilage particles. In an embodiment of the present invention, the cartilage-derived implant comprises cartilage fibers, cartilage particles, and at least one additional component. In an embodiment, the at least one additional component is a carrier or another biologically-compatible material. In an embodiment, suitable carriers and biologically-compatible materials include, but are not necessarily limited to, the following: an aqueous buffer, an isotonic solution; a sodium chloride solution at a concentration of about 0.1% to about 1%, more particularly, about 0.9%; a lactated Ringer's solution, with or without D5LR (dextrose); phosphate buffered saline ("PBS"); platelet rich plasma (PRP); glycerin; lecithin; alginate; hyaluronic acid (HA); a derivative of HA; or sodium hyaluronate; or other suitable carriers known in the art. The carrier may also comprise "biological components" added to the carrier, such as, but not limited to, DNA, RNA, short hairpin RNA (shRNA), small interfering RNA (siRNA), micro RNA (mRNA), polysaccharides, peptides, matrix proteins, glycosaminoglycans (e.g., hyaluronic acid), viral vectors, and liposomes. Biologically-compatible materials that are not necessarily inert, but are also suitable for combination with the cartilage fibers and cartilage particles include, but are not necessarily limited to, bone marrow aspirate (BMA), platelet rich plasma (PRP), growth factors, blood, synovial fluid, fibrin glue, and acellular bulking agents derived from soft tissues such as fascia, adipose tissue, placental tissues, or other soft tissues. In an embodiment, exogenous viable cells are added to the cartilage fibers and cartilage particles. Such exogenous viable cells may include, but are not necessarily limited to, autologous or allogeneic chondrocytes, autologous cells such as those obtained from the patient's bone marrow or stromal vascular fraction (SVF) allogeneic cells such as those obtained from a cell bank (e.g., stem cells, progenitor cells or other cell types available from cell banks), or bone marrow and bone marrow components including bone marrow cells (both autologous and allogeneic).

In an embodiment of the present invention, the cartilage fibers are provided separately from the cartilage particles (e.g., in a kit). In an embodiment, the cartilage fibers and cartilage particles are provided separately from each other, and are combined to make the cartilage-derived implant in the operating room prior to being administered to a patient in need thereof. In an embodiment, the cartilage fibers and cartilage particles are combined with a carrier or other biologically-compatible material to make a paste. In an embodiment, the cartilage fibers and cartilage particles are combined with a carrier or other biologically-compatible material to make a putty. In an embodiment, the cartilage fibers are combined with a carrier or other biologically-compatible material to make a paste. In an embodiment, the cartilage fibers are combined with a carrier or other biologically-compatible material to make a strip. In an embodiment, the cartilage fibers are combined with a carrier or other biologically-compatible material to make a gel. In an embodiment, the cartilage fibers and cartilage particles are combined with a carrier or other biologically-compatible material to make a mixture that is injectable into a cartilage defect.

In an embodiment of the present invention, the cartilage-derived implant is prepared, and then stored under conditions that preserve the viability of native or added cells. The cartilage-derived implant is then thawed and warmed to ambient or physiological temperatures before being administered to a patient in need thereof. Suitable storage conditions include those discussed in Section III of the present disclosure with respect to fresh cartilage fibers.

VI. SHAPED CARTILAGE-DERIVED IMPLANTS

In an embodiment of the present invention, shaped cartilage-derived implants include three-dimensional shaped structures formed by a process in which articular cartilage is broken into fibers, then reformed into a three-dimensional structure. Suitable cartilage fibers may be prepared using methods disclosed in Sections I and II of the present application or by other methods that may be known in the art. Suitable cartilage fibers may be fresh cartilage fibers, dehydrated cartilage fibers, frozen cartilage fibers, cartilage fibers including non-viable cells, lyophilized cartilage fibers, or rehydrated cartilage fibers.

In an embodiment of the present invention, cartilage fibers are suspended in a liquid (e.g., water or a buffer solution) to form a flowable mass, such as a slurry. The flowable mass may be poured into a mold of a desired shape, in which it may form a porous or sponge-like shaped acellular tissue upon dehydration or lyophilization. In an embodiment, a mass of cartilage fibers is manipulated to form a putty, which can then be molded into a desired shape. In an embodiment, the cartilage fibers are manipulated with a liquid to form a paste. In an embodiment, the cartilage fibers are mixed with a polymer to form a paste or a putty. In an embodiment, a shaped cartilage-derived implant is formed by dehydrating the slurry, paste or gel. In an embodiment, a shaped cartilage-derived implant is formed by lyophilizing the slurry, paste or gel. In an embodiment, the density or porosity of a shaped cartilage-derived implant is controlled by selecting the amount of carrier or other liquid relative to the amount of cartilage fiber. In an embodiment, the shaped cartilage-derived implant is a solid piece that conforms to the shape of a mold after being dehydrated or lyophilized. In an embodiment, a shaped cartilage-derived implant may be provided in a lyophilized, dehydrated, cryopreserved, or frozen form.

In embodiments of the present invention, the liquids added to tissue before and/or during the molding process could optionally contain therapeutic factors, cytokines, growth factors, pharmaceuticals, antibiotics, free-radical scavengers, sugars, vitamins including, but not limited to, riboflavin and ascorbic acid, surfactants, DMEM medium, human or animal serum, or other additives. The addition or removal of liquid from the tissue also allows the density of the final implant to be controlled.

In an embodiment of the present invention, the shaped cartilage-derived implant includes cartilage fibers that have been aligned to form a sheet. In an embodiment, the shaped cartilage-derived implant includes cartilage fibers that have been interwoven to form a sheet. In an embodiment, the shaped cartilage-derived implant includes a mass of cartilage fibers that have been pressed to form a sheet. In an embodiment, the shaped cartilage-derived implant includes cartilage fibers that have been placed into a mold to form a pre-shaped implant. In an embodiment, the pre-shaped implant is a sheet. In an embodiment, the pre-shaped implant is a block. In an embodiment, the pre-shaped implant is a disk. In an embodiment, the pre-shaped implant is a dome. In an embodiment, the pre-shaped implant is sphere. In an embodiment, the pre-shaped implant is portion of a sphere.

In an embodiment, shaped cartilage-derived implants may be used to surgically repair cartilage defects in a patient or worn or damaged cartilage in a patient. In an embodiment, shaped cartilage-derived implants are used alone or after being seeded or cultured with appropriate exogenous cells, such as the exogenous cells identified with respect to the cartilage-derived implants of Sections I, II and V of the present disclosure. In an embodiment, the shaped cartilage-derived implants are provided with bioactive components such as growth factors, proteins, angiogenic factors, and other bioactive components such as those discussed with respect to the cartilage-derived fiber implants of Sections I, II and V of the present disclosure. In an embodiment, one or more biologically-compatible substances are added to the shaped cartilage-derived implant, such as carriers or other biologically-compatible substances that are discussed with respect to the cartilage-derived implants of Sections I, II and V of the present disclosure. In an embodiment, the exogenous cells, bioactive components, or biologically-compatible substances are added to the slurry, putty, paste, gel, or cartilage fiber mass or sheet before the shaped cartilage-derived implant is formed. In an embodiment, the exogenous cells, bioactive components, or biologically-compatible substances are added to the shaped cartilage-derived implant after it is shaped, but before it is lyophilized, dehydrated, cryopreserved, or frozen. In an embodiment, the degradation profile of the shaped cartilage-derived implant and a substance added thereto cause the substance to be released at an appropriate time for growth or healing of tissues to occur.

In an embodiment of the present invention, the shaped cartilage-derived implant has a simple shape. In an embodiment, the shaped cartilage-derived implant has a complex shape. In an embodiment, the shaped cartilage-derived implant has a symmetrical shape. In an embodiment, the shaped cartilage-derived implant has an asymmetrical shape.

In an embodiment of the present invention, the shaped cartilage-derived implant has a porosity customized for its intended use. In an embodiment, the shaped cartilage-derived implant has a pH customized for its intended use. In an embodiment, the shaped cartilage-derived implant includes cross-linked collagen. In an embodiment, the shaped cartilage-derived implant includes cross-linked non-collagen components. In an embodiment, the shaped cartilage-derived implant has biological polymers that are cross-linked with non-biological (i.e., synthetic) polymers.

In an embodiment of the present invention, a method of forming a shaped cartilage-derived implant includes a step of scanning or imaging a cartilaginous portion of a patient's body (e.g., a nose or an ear), then making shaped cartilage-derived implants to replace those anatomical structures. In an embodiment, a shaped cartilage-derived implant is made to restore the shape of a cartilaginous anatomical structure. In an embodiment, a shaped cartilage-derived implant is made to provide a substitute for a cartilaginous anatomical structure. Methods of making such a shaped cartilage-derived implant include any method of forming a putty, a paste, a gel, a slurry, or a mass of cartilage fibers into a three-dimensional object, and include, but are not necessarily limited to, casting, molding, and three-dimensional printing.

In an embodiment of the present invention, the shaped cartilage-derived implant is formed, then cultured in vitro with exogenous cells. When the cells reach a sufficient number, the shaped cartilage-derived implant is implanted for orthopedic, plastic, reconstructive or regenerative surgery or used in cartilage repair procedures.

In an embodiment of the present invention, the shaped cartilage-derived implant is formed, then cultured in vitro with cells. When the cells reach a sufficient number, the shaped cartilage-derived implant is cryopreserved, and then reconstituted when needed for use.

In an embodiment of the present invention, mesenchymal stem cells are harvested from a patient in need of a nasal graft, cultured onto a shaped cartilage-derived implant resembling the patient's own nasal structure. In an embodiment of the present invention, mesenchymal stem cells are harvested from a patient in need of an ear graft, cultured onto a shaped cartilage-derived implant resembling the patient's own ear. The shaped cartilage-derived implant could optionally resemble other structures natural to patient's own body, for example but not limited to nasal septum, sternum, trachea, bronchea, articular cartilage, osteroarticular cartilage, costal cartilage. After the cells have differentiated into a sufficient number of chondrocytes, the shaped cartilage-derived implant can be provided to the patient as a viable graft.

In an embodiment of the present invention, a shaped cartilage-derived implant is provided in a lyophilized form. The lyophilized shaped cartilage-derived implant is rehydrated in the operating room, where it may be combined with such substances as the patient's platelet-rich plasma (PRP), autologous cells such as those obtained from the patient's bone marrow or stromal vascular fraction (SVF) (e.g., SVF from adipose tissue obtained by liposuction), allogeneic cells such as those obtained from a cell bank (e.g., stem cells, progenitor cells or other cell types available from cell banks), or bone marrow and bone marrow components including bone marrow cells (both autologous and allogeneic).

In an embodiment of the present invention, a shaped cartilage-derived implant is provided in a dehydrated form. The dehydrated shaped cartilage-derived implant is rehydrated in the operating room, where it may be combined with such substances as the patient's platelet-rich plasma (PRP), autologous cells such as those obtained from the patient's bone marrow or stromal vascular fraction (SVF) (e.g., SVF from adipose tissue obtained by liposuction), allogeneic cells such as those obtained from a cell bank (e.g., stem cells, progenitor cells or other cell types available from cell banks), or bone marrow and bone marrow components including bone marrow cells (both autologous and allogeneic).

VII. OTHER FORMS OF CARTILAGE

In embodiments of the present invention, the cartilage-derived implant may include cartilage tissue forms other than cartilage fibers and cartilage particles. For example, minced cartilage or sheets of cartilage cut from recovered intact body parts may be used in place of, or in combination with, cartilage fibers and cartilage particles in the implants discussed in the present disclosure. Such minced cartilage or cartilage sheets may be in fresh, dehydrated, or lyophilized form, and may be processed or used in similar fashion to the cartilage fibers and cartilage particles.

VIII. EXAMPLES

The following examples are put forth so as to provide those of ordinary skill in the art with a disclosure and description of exemplary embodiments of the described invention, and are not intended to limit the scope of what the inventors regard as their invention nor are they intended to represent that the experiments below are all or the only experiments performed. Efforts have been made to ensure accuracy with respect to numbers used (e.g., amounts, temperatures, etc.) but some experimental errors and deviations should be accounted for. Unless indicated otherwise, parts are parts by weight, molecular weight is weight average molecular weight, temperature is in degrees centigrade (° C.), and pressure is at or near atmospheric.

Example 1

Viability of Fresh Cartilage Fibers

Fresh cartilage fibers were assayed for viable cells. Viability was determined by total cell counts and live/dead cell counts. Alternative means can be used to assess cell viability of intact fibers, such as standard methods utilizing the adenosine triphosphate (ATP) assays or routine cell viability reagents (e.g., PrestoBlue®; ThermoFisher Scientific, Waltham, Mass.) as described in the literature, although such methods were not used in the present example.

Femoral condyles were recovered from an adult human donor, cut into hemi-condyles, and stored in growth media. The recovered hemi-condyles were submerged in growth media, and separated into two groups: Group A and Group B. Fresh cartilage fibers from Group A were obtained by grating the cartilage of the hemi-condyles while the hemi-condyles were totally submerged in growth media. Fresh cartilage fibers from Group B were obtained by grating the cartilage of the hemi-condyles outside of the growth media, and depositing the fibers into the growth media. Fresh cartilage fibers were then separated from the growth media, placed into separate vials, and covered with growth media, after which the vials were sealed and stored in sealed Kapak® pouches until the fibers were tested for viability.

Fresh cartilage fibers from Group A and Group B were tested separately for viability. Prior to testing, the fresh cartilage fibers were separated from the growth media by settling. Cells were recovered from the fresh cartilage fibers by digestion with Pronase® and collagenase II, following protocols known in the art. Cell counts were performed on the resulting cell suspensions using Trypan Blue, following protocols known in the art. Fluorescent live/dead counts were performed on cells plated from the suspensions, following protocols known in the art. Cartilage digestion and cell recovery for Group A and Group B were completed on the same day that the condyles were recovered from the human donor. All viability tests were performed promptly thereafter.

The total number of cells counted for fresh cartilage fibers from Group A and Group B were $2.44 \times 10^6$/mL suspension and $3.09 \times 10^6$/mL suspension, respectively. The live/dead counts indicated that 94.5% of the cells of Group A and 93.0% of the cells from Group B were viable.

Example 2

Viability of Fresh and Cryopreserved Cartilage Fibers

Fresh and cryopreserved cartilage fibers were assayed for viable cells. Cryopreserved fibers were assayed at 0 hours and 48 hours after cryopreservation. Viability was determined by total cell counts and live/dead cell counts.

Femoral condyles were recovered from an adult human donor, cut into hemi-condyles, and stored in growth media. Each recovered hemi-condyle was removed from the growth media, and securely mounted onto a vise. Fresh cartilage fibers were harvested from the hemi-condyle using a grater, and periodically transferred from the grater to a container of growth media.

When a sufficient amount of fresh cartilage fibers had been collected, the cartilage fibers were separated from the growth media, and divided among vials with growth media and jars with a cryopreservation solution (100 mL DMSO/1 L Hyclone™ media). The vials and jars were immediately sealed in foil pouches, and transferred to a laboratory for viability testing.

Digestion of the fresh cartilage fibers from the vials (Group A) was started immediately upon receipt at the laboratory. Fresh cartilage fibers from one group of jars (Group B) were subjected to a cryopreservation cycle, and the cartilage digestion was started immediately after the cryopreservation cycle. Fresh cartilage fibers from another group of jars (Group C) were cryopreserved, and the cartilage digestion was started at about 48 hours after the cryopreservation cycle. All viability tests were performed promptly after the cells were recovered.

Prior to testing, the fresh cartilage fibers were separated from the growth media and cryopreserved cartilage fibers were separated from both growth media and cryopreservation solution. Cells were recovered from the cartilage fibers by digestion with Pronase® and collagenase II, following protocols known in the art. Cell counts were performed on the resulting cell suspensions using Trypan Blue, following protocols known in the art. Fluorescent live/dead counts were performed on cells plated from the suspensions, following protocols known in the art.

The total number of cells counted for cartilage fibers from Groups A, B, and C were $3.85 \times 10^6$/mL suspension, $0.8 \times 10^6$/mL suspension, and $0.91 \times 10^6$/mL suspension, respectively. The live/dead counts indicated that the percentages of viable cells for Groups A, B, and C were 92.0%, 66.6%, and 70.0%, respectively.

Example 3

Viability of Fresh and Cryopreserved Cartilage Fibers

Fresh and cryopreserved cartilage fibers were assayed for viable cells. Cryopreserved fibers were assayed at 0 hours and 48 hours after cryopreservation. Viability was determined by total cell counts, and live/dead cell counts.

Femoral condyles were recovered from an adult human donor, cut into hemi-condyles, and stored in growth media. Each recovered hemi-condyle was removed from the growth media, and securely mounted onto a vise. Fresh cartilage fibers were harvested from the hemi-condyle using a grater, and periodically transferred from the grater to a container of growth media.

When a sufficient amount of fresh cartilage particles had been collected, the cartilage fibers were separated from the growth media, and divided among vials with growth media and jars with a cryopreservation solution (100 mL DMSO/1 L Hyclone™ media). The vials and jars were immediately sealed in foil pouches, and transferred to a laboratory for viability testing.

Digestion of the fresh cartilage fibers from the vials (Group A) was started immediately upon receipt at the laboratory. Fresh cartilage fibers from one group of jars (Group B) were subjected to a cryopreservation cycle, and the cartilage digestion was started immediately after the cryopreservation process. Fresh cartilage fibers from another group of jars (Group C) were cryopreserved, and the cartilage digestion was started at about 48 hours after the cryopreservation cycle. All viability tests were performed promptly after the cells were recovered.

Prior to testing, the fresh cartilage fibers were separated from the growth media and cryopreserved cartilage fibers were separated from both growth media and cryopreservation solution. Cells were recovered from the cartilage fibers by digestion with Pronase® and collagenase II, following protocols known in the art. Cell counts were performed on the resulting cell suspensions using Trypan Blue, following protocols known in the art. Fluorescent live/dead counts were performed on cells plated from the suspensions, following protocols known in the art.

The total number of cells counted for cartilage fibers from Groups A, B, and C were $3.38 \times 10^6$/mL suspension, $1.52 \times 10^6$/mL suspension, and $1.05 \times 10^6$/mL suspension, respectively. The live/dead counts indicated that the percentages of viable cells for Groups A, B, and C were 88.1%, 62.0%, and 66.4%, respectively.

Example 4

Viability of Fresh and Cryopreserved Cartilage Fibers

Fresh and cryopreserved cartilage fibers were assayed for viable cells. Cryopreserved fibers were assayed at 48 hours after cryopreservation. Viability was determined by total cell counts and live/dead cell counts.

Femoral condyles were recovered from an adult human donor, cut into hemi-condyles, and stored in growth media. Each recovered hemi-condyle was removed from the growth media, and securely mounted onto a vise. Fresh cartilage fibers were harvested from the hemi-condyle using a grater, and periodically transferred from the grater to a container of growth media.

When a sufficient amount of fresh cartilage particles had been collected, the cartilage fibers were separated from the growth media, and divided among vials with growth media and jars with a cryopreservation solution (100 mL DMSO/1 L Hyclone™ media). The vials and jars were immediately sealed in foil pouches, and transferred to a laboratory for viability testing.

Digestion of the fresh cartilage fibers from the vials (Group A) was started immediately upon receipt at the laboratory. Fresh cartilage fibers from the group of jars (Group B) were cryopreserved, and the cartilage digestion was started at about 48 hours after the cryopreservation cycle. All viability tests were performed promptly after the cells were recovered.

Prior to testing, the fresh cartilage fibers were separated from the growth media and cryopreserved cartilage fibers were separated from both growth media and cryopreservation solution. Cells were recovered from the cartilage fibers by digestion with Pronase® and collagenase II, following protocols known in the art. Cell counts were performed on the resulting cell suspensions using Trypan Blue, following protocols known in the art. Fluorescent live/dead counts were performed on cells plated from the suspensions, following protocols known in the art.

The total number of cells counted for cartilage fibers from Group A and Group B were $2.86 \times 10^6$/mL suspension and $0.71 \times 10^6$/mL suspension, respectively. The live/dead counts indicated that the percentages of viable cells for Group A and Group B were 91.1% and 69.2%, respectively.

Example 5

Viability of Fresh and Cryopreserved Cartilage Fibers

Fresh and cryopreserved cartilage fibers were assayed for viable cells. Cryopreserved fibers were assayed at 48 hours and 14 days after cryopreservation. Viability was determined by total cell counts and live/dead cell counts.

Femoral condyles were recovered from an adult human donor, cut into hemi-condyles, and stored in growth media. Each recovered hemi-condyle was removed from the growth media, and securely mounted onto a vise. Fresh cartilage fibers were harvested from the hemi-condyle using a grater, and periodically transferred from the grater to a container of growth media.

When a sufficient amount of fresh cartilage particles had been collected, the cartilage fibers were separated from the growth media, and divided among vials with growth media and jars with a cryopreservation solution (100 mL DMSO/1 L Hyclone™ media). The vials and jars were immediately sealed in foil pouches, and transferred to a laboratory for viability testing.

Digestion of the fresh cartilage fibers from the vials (Group A) was started immediately upon receipt at the laboratory. Fresh cartilage fibers from one group of jars (Group B) were cryopreserved, and the cartilage digestion was started at about 48 hours after the cryopreservation cycle. Fresh cartilage fibers from another group of jars (Group C) were cryopreserved, and the cartilage digestion was started on day 14 after the cryopreservation cycle. All viability tests were performed promptly after the cells were recovered.

Prior to testing, the fresh cartilage fibers were separated from the growth media and cryopreserved cartilage fibers were separated from both growth media and cryopreservation solution. Cells were recovered from the cartilage fibers by digestion with Pronase® and collagenase II, following protocols known in the art. Cell counts were performed on the resulting cell suspensions using Trypan Blue, following protocols known in the art. Fluorescent live/dead counts were performed on cells plated from the suspensions, following protocols known in the art.

The total number of cells counted for cartilage fibers from Groups A, B, and C were $1.61\times10^6$/mL suspension, $0.625\times10^6$/mL suspension, and $0.29\times10^6$/mL suspension, respectively. The live/dead counts indicated that the percentages of viable cells for Groups A, B, and C were 87.6%, 66.1%, and 68.1%, respectively.

Example 6

Viability of Fresh and Cryopreserved Cartilage Fibers

Fresh and cryopreserved cartilage fibers were assayed for viable cells. Cryopreserved fibers were assayed at 0 hours and 35 days after cryopreservation. Viability was determined by total cell counts and live/dead cell counts.

Femoral condyles were recovered from an adult human donor, cut into hemi-condyles, and stored in growth media. Each recovered hemi-condyle was removed from the growth media, and securely mounted onto a vise. Fresh cartilage fibers were harvested from the hemi-condyle using a grater, and periodically transferred from the grater to a container of growth media.

When a sufficient amount of fresh cartilage particles had been collected, the cartilage fibers were separated from the growth media, and divided among vials with growth media and jars with a cryopreservation solution (100 mL DMSO/1 L Hyclone™ media). The vials and jars were immediately sealed in foil pouches, and transferred to a laboratory for viability testing.

Digestion of the fresh cartilage fibers from the vials (Group A) was started immediately upon receipt at the laboratory. Fresh cartilage fibers from one group of jars (Group B) were subjected to a cryopreservation cycle, and the cartilage digestion was started at about two hours after receipt at the laboratory. Fresh cartilage fibers from another group of jars (Group C) were cryopreserved, and the cartilage digestion was started at about 35 days after the cryopreservation cycle. All viability tests were performed promptly after the cells were recovered.

Prior to testing, the fresh cartilage fibers were separated from the growth media and cryopreserved cartilage fibers were separated from both growth media and cryopreservation solution. Cells were recovered from the cartilage fibers by digestion with Pronase® and collagenase II, following protocols known in the art. Cell counts were performed on the resulting cell suspensions using Trypan Blue, following protocols known in the art. Fluorescent live/dead counts were performed on cells plated from the suspensions, following protocols known in the art.

The total number of cells counted for cartilage fibers from Groups A, B, and C were $3.42\times10^6$/mL suspension, $0.735\times10^6$/mL suspension, and $0.615\times10^6$/mL suspension, respectively. The live/dead counts indicated that the percentages of viable cells for Groups A, B, and C were 88.1%, 66.8%, and 71.4%, respectively.

Example 7

Handling Characteristics of Mixtures of Fresh Cartilage Fibers with Lyophilized Cartilage Particles Fresh articular cartilage fibers were mixed at various ratios with lyophilized cartilage particles having sizes of less than 212 microns to assess the handling characteristics of the mixture. It was found that the fresh fibers provided sufficient moisture to bind with the lyophilized particles and form a cohesive putty that was easily handled. Mixtures that included more than about 35% to about 45% particles by weight were not as cohesive as mixtures having particle contents of less than about 35% by weight.

Example 8

Rehydration of Lyophilized Cartilage Fibers

Fresh cartilage fibers were collected by grating articular cartilage from intact hemi-condyles. The following fluids were added to samples of the fresh cartilage fibers: synovial fluid, blood, platelet rich plasma (PRP), growth media, Sorenson's buffer, and standard saline. One sample of fresh cartilage fibers received no fluids. Each sample of the fresh cartilage fibers was then lyophilized. All of the lyophilized samples were found to be stiff when handled.

The lyophilized samples of cartilage fibers treated with saline, growth media, and no liquid were then rehydrated. Each sample formed a cohesive putty.

Lyophilized cartilage fibers which had received no fluids were soaked overnight in growth media. The rehydrated fibers looked and felt like fresh cartilage fibers, and had the same handling properties as fresh cartilage fibers.

Example 9

Formulations of Cartilage Fibers and Cartilage Particles

Fresh cartilage fibers were collected by grating articular cartilage from thawed hemi-condyles. The fresh cartilage fibers were soaked for up to 4 hours in growth media, then drained in a 212 μm sieve. Lyophilized cartilage fibers, prepared without adding a fluid, and lyophilized cartilage particles were previously prepared according to methods discussed in the present disclosure.

In a first formulation, lyophilized cartilage fibers (0.12 g) were mixed with lyophilized cartilage particles (0.2 g) and defibrinated sheep blood (0.7 mL). The formulation mixed readily into a cohesive mass. A portion of the mixture was placed in a cartilage defect in a knee-en-bloc, where it stuck well. The mixture remained firm in the defect after the knee-en-bloc had been articulated 20 times with a saline drip In a second formulation, lyophilized cartilage fibers (0.3 g) were mixed with defibrinated sheep blood (0.7 mL). The formulation was difficult to mix, but gradually improved. A portion of the mixture was placed in a cartilage defect in a knee-en-bloc, where it stuck well. The mixture remained in the defect after the knee-en-bloc had been articulated 20 times without a saline drip. The mixture began to swell after the knee-en-bloc was articulated 20 times with a saline drip.

In a third formulation, fresh cartilage fibers (0.5 g) were mixed with lyophilized cartilage fibers (0.5 g). The formulation did not mix well, and was dry and crumbly.

In a fourth formulation, fresh cartilage fibers (0.6 g) were mixed with lyophilized cartilage fibers (0.4 g). The formulation was dry and did not mix well, but formed a cohesive mass upon further manipulation. A portion of the mixture was placed in a cartilage defect in a knee-en-bloc, where it stuck well. The mixture remained in the defect after the knee-en-bloc had been articulated 20 times with a saline drip.

In a fifth formulation, fresh cartilage fibers (0.8 g) were mixed with lyophilized cartilage particles (0.2 g). The formulation mixed easily into a cohesive putty-like mass. A portion of the mixture was placed in a cartilage defect in a knee-en-bloc, where it stuck well. The mixture remained firm in the defect after approximately 20 articulations with a saline drip.

In a sixth formulation, fresh cartilage fibers (0.85 g) were mixed with lyophilized cartilage particles (0.15 g). The formulation mixed easily into a cohesive putty-like mass. A portion of the mixture was placed in a cartilage defect in a knee-en-bloc, where it stuck well. The mixture remained firm in the defect after approximately 20 articulations with a saline drip.

In a seventh formulation, fresh cartilage fibers (0.75 g) were mixed with lyophilized cartilage particles (0.25 g). The formulation mixed easily into a cohesive putty-like mass. A portion of the mixture was placed in a cartilage defect in a knee-en-bloc, where it stuck well. The mixture remained firm in the defect after approximately 20 articulations with a saline drip.

Example 10

Viability of Cryopreserved Cartilage Fibers

Cryopreserved cartilage fibers were assayed for viable cells. Cryopreserved fibers were assayed approximately 6 months after cryopreservation. Viability was determined by total cell counts and live/dead cell counts.

Femoral condyles were recovered from an adult human donor, cut into hemi-condyles, and stored in growth media. Each recovered hemi-condyle was removed from the growth media, and securely mounted onto a vise. Fresh cartilage fibers were harvested from the hemi-condyle using a grater, and periodically transferred from the grater to a container of growth media.

When a sufficient amount of fresh cartilage particles had been collected, the cartilage fibers were separated from the growth media, and divided among vials with a cryopreservation solution (100 mL DMSO/1 L Hyclone™ media) to form Group A. The vials were immediately sealed in foil pouches and cryopreserved using controlled rate freezing. Following cryopreservation, samples were stored in a Liquid Nitrogen (LN) tank until time of testing.

Digestion of the cryopreserved cartilage fibers from the vials (Group A) was started about 6 months after cryopreservation and storage in LN tanks. All viability tests were performed promptly after the cells were recovered.

Prior to testing, the cryopreserved cartilage fibers were separated from the cryopreservation solution. Cells were recovered from the cryopreserved cartilage fibers by digestion with Pronase® and collagenase II, following protocols known in the art. Cell counts were performed on the resulting cell suspensions using Trypan Blue, following protocols known in the art. Fluorescent live/dead counts were performed on cells plated from the suspensions, following protocols known in the art.

The total number of cells counted for cryopreserved cartilage fibers from Group A was $0.220 \times 10^6$/mL suspension. The live/dead counts indicated that the percentage of viable cells for Groups A was 71.1%.

Example 11

Viability of Cryopreserved Cartilage Fibers and Storage Conditions

Cryopreserved cartilage fibers were assayed for viable cells. Cryopreserved fibers were assayed approximately 6 months after cryopreservation. Viability was determined by total cell counts and live/dead cell counts.

Femoral condyles were recovered from an adult human donor, cut into hemi-condyles, and stored in growth media. Each recovered hemi-condyle was removed from the growth media, and securely mounted onto a vise. Fresh cartilage fibers were harvested from the semi-condyle using a grater, and periodically transferred from the grater to a container of growth media.

When a sufficient amount of fresh cartilage particles had been collected, the cartilage fibers were separated from the growth media, and divided among vials with a cryopreservation solution (100 mL DMSO/1 L Hyclone™ media). The vials were immediately sealed in foil pouches and cryopreserved using controlled rate freezing. Following cryopreservation, samples were split into two groups. Group A samples were stored in the LN tank and Group B samples were stored in a −70 C freezer until time of testing.

Digestion of the cryopreserved cartilage fibers from the vials of Group A and Group B were started about 6 months after cryopreservation and storage in either an LN tank (Group A) or −70 C freezer (Group B). All viability tests were performed promptly after the cells were recovered.

Prior to testing, the cryopreserved cartilage fibers were separated from the cryopreservation solution. Cells were recovered from the cryopreserved cartilage fibers by digestion with Pronase® and collagenase II, following protocols known in the art. Cell counts were performed on the resulting cell suspensions using Trypan Blue, following protocols known in the art. Fluorescent live/dead counts were performed on cells plated from the suspensions, following protocols known in the art.

The total number of cells counted for cryopreserved cartilage fibers from Group A and Group B were $0.205 \times 10^6$/mL suspension and $0.145 \times 10^6$/mL suspension, respectively. The live/dead counts indicated that the percentage of viable cells for Groups A and Group B were 65.5% and 68.1%, respectively.

IX. GLOSSARY

The term "acellular" as used herein means substantially free of cells and their components (including DNA).

The term "ambient temperature" as used herein refers to the temperature of the immediate, unaltered surroundings. Ambient temperature is between about 15° C. and about 30° C. According to some embodiments, ambient temperature is room temperature.

The term "adherent" in all of its grammatical forms, as used herein refers to the act of sticking to, clinging, or staying attached.

The term "administer" as used herein means to give or to apply.

The term "allogeneic" as used herein refers to being genetically different although belonging to or obtained from the same species. The term "allogeneic" may be used interchangeably herein with the term "allogenic".

The term "allogenic graft", "allogeneic graft" or "allograft" as used herein refers to a tissue that is recovered from one individual and implanted into different individual of the same species.

The term "attached" as used herein refers to being fastened, fixed, joined, connected, bound, adhered to or assembled with.

The term "autologous" as used herein means derived from the same organism.

The term "autologous graft" or "autograft" as used herein refers to a tissue that is grafted into a new position in or on the body of the same individual.

The term "biocompatible" as used herein refers to causing no clinically relevant tissue irritation, injury, toxic reaction, or immunological reaction to living tissue.

The term "buffer" or "buffer solution" as used herein refers to a compound, usually a salt, which, when dissolved in an aqueous medium, serves to maintain the free hydrogen ion concentration of the solution within a certain pH range when hydrogen ions are added or removed from the solution. A salt or solution is said to have a "buffering capacity" or to buffer the solution over such a range, when it provides this function. Generally a buffer will have adequate buffering capacity over a range that is within ±0.1 pH unit of its pK.

The term "buffered isotonic solution" as used herein refers to any buffer that is commonly used in biological research or the commercial biotechnology field. Exemplary buffered isotonic solutions include but are not limited to balanced salt solution (BSS), Hank's Balanced Salt Solution, Grey's Balanced Salt Solution, Hank's Buffered Salt Solution, Phosphate Buffered Saline, Tris-Buffered Saline, etc. The term "isotonic solution" as used herein refers to a solution whose osmolarity and ion concentrations closely match those within normal cells of the body and the blood.

The term "carrier" as used herein refer to a pharmaceutically acceptable inert agent or vehicle for delivering one or more biological components or active agents to a subject, and often is referred to as an "excipient." The carrier must be of sufficiently high purity and of sufficiently low toxicity to render it suitable for administration to the subject being treated. The carrier further should maintain the stability and bioavailability of the biological component or active agent The term "cell" is used herein to refer to the structural and functional unit of living organisms and is the smallest unit of an organism classified as living.

The term "chondrocytes" as used herein refers to cells found in cartilage that produce and maintain the cartilaginous matrix for, for example, joints, ear canals, trachea, epiglottis, larynx, the discs between vertebrae and the ends of ribs. From least to terminally differentiated, the chondrocytic lineage is (i) Colony-forming unit-fibroblast (CFU-F); (ii) mesenchymal stem cell/marrow stromal cell (MSC); (iii) chondrocyte.

The term "chondrogenesis" as used herein refers to the formation of new cartilage from cartilage forming or chondrocompetent cells.

The term "chondrogenic" as used herein refers to a potential of precursor cells to differentiate into cartilage forming or chondrocompetent cells.

The term "compatible" as used herein means that the components of a composition are capable of being combined with each other in a manner such that there is no interaction that would substantially reduce the efficacy of the composition under ordinary use conditions.

The term "component" as used herein refers to a constituent part, element or ingredient.

The term "condition", as used herein, refers to a variety of health states and is meant to include disorders or diseases caused by any underlying mechanism or disorder, injury, and the promotion of healthy tissues and organs.

The term "condyle" as used herein means the rounded protuberance or projection at the end of a bone forming an articulation with another bone.

The term "contact" and its various grammatical forms as used herein refers to a state or condition of touching or of immediate or local proximity. Contacting a composition to a target destination may occur by any means of administration known to the skilled artisan.

"Decellularization", as used herein in all of its grammatical forms, is any process by which at least some of the endogenous cells and cellular components (including DNA) are removed from a tissue, thereby leaving the extracellular matrix (ECM) which may be essentially free of such cells and cellular components.

The term "dehydrate", as used herein in all of its grammatical forms, means removal of at least a portion of water that is initially present.

The term "devitalization", as used herein in all of its grammatical forms, is any process which renders a tissue substantially or essentially free from reproductively or metabolically viable cells, without necessarily leaving the tissue essentially free of such cells and cellular components. In other words, a devitalized tissue is a tissue in which less than 5%, by weight, of its native cells remain metabolically viable, compared to the total weight of the metabolically viable cells originally present in the tissue.

The term "endogenous" as used herein refers to that which is naturally occurring, incorporated within, housed within, adherent to, attached to or resident in.

The term "extracellular matrix" as used herein refers to a scaffold in a cell's external environment with which the cell interacts via specific cell surface receptors. The extracellular matrix serves many functions, including, but not limited to, providing support and anchorage for cells, segregating one tissue from another tissue, and regulating intracellular communication. The extracellular matrix is composed of an interlocking mesh of fibrous proteins and glycosaminoglycans (GAGs). Examples of fibrous proteins found in the extracellular matrix include collagen, elastin, fibronectin, and laminin. Examples of GAGs found in the extracellular matrix include proteoglycans (e.g., heparin sulfate), chondroitin sulfate, keratin sulfate, and non-proteoglycan polysaccharide (e.g., hyaluronic acid). The term "proteoglycan" refers to a group of glycoproteins that contain a core protein to which is attached one or more glycosaminoglycans.

The term "factors" as used herein refers to nonliving components that have a chemical or physical effect. For example, a "paracrine factor" is a diffusible signaling molecule that is secreted from one cell type that acts on another cell type in a tissue. A "transcription factor" is a protein that binds to specific DNA sequences and thereby controls the transfer of genetic information from DNA to mRNA.

The term "fiber" as used herein refers to an elongated piece of tissue having a thread-like or ribbon-like shape.

The term "fluorescence" as used herein refers to the result of a three-state process that occurs in certain molecules, generally referred to as "fluorophores" or "fluorescent dyes," when a molecule or nanostructure relaxes to its ground state after being electrically excited. Stage 1 involves the excitation of a fluorophore through the absorption of light energy; Stage 2 involves a transient excited lifetime with some loss of energy; and Stage 3 involves the return of the fluorophore to its ground state accompanied by the emission of light.

The term "graft" as used herein refers to a tissue or organ transplanted from a donor to a recipient. It includes, but is not limited to, a tissue transferred from one body site to another in the same individual ("autologous graft"), a tissue transferred between genetically identical individuals or sufficiently immunologically compatible to allow tissue transplant ("syngeneic graft"), a tissue transferred between genetically different members of the same species ("allogeneic graft" or "allograft"), and a tissue transferred between different species ("xenograft").

The term "growth" as used herein refers to a process of becoming larger, longer or more numerous, or an increase in size, number, or volume.

The term "growth conduction" as used herein refers to a process by which a tissue is directed to regenerate or grow so as to conform to a material's surface. A growth-conductive surface is one that permits tissue growth on its surface or down into pores, channels or pipes. Growth-conductive material facilitates the spontaneous formation of a tissue by furnishing a microenvironment that supports deposition or adhesion of tissuegenic cells and optionally, vascularization. Examples of growth-conductive materials, include, but are not limited to, processed human bone (e.g., allograft bone, which may be an osteoconductive material), purified collagen, calcium phosphate ceramics, synthetic polymers, tissue-derived matrices, BMP-2 and 4, VEGF, bFGF, TGF-$\beta$, and PDGF.

The term "growth-conductive matrix" as used herein refers to a matrix that may be inert in and of itself but which supports three-dimensional tissue formation. For example, allograft bone tissue may be an osteoconductive matrix.

The term "growth factor" as used herein refers to extracellular polypeptide molecules that bind to a cell-surface receptor triggering an intracellular signaling pathway, leading to proliferation, differentiation, or other cellular response. Growth factors include, but are not limited to, cytokines and hormones.

The term "growth induction" as used herein refers to a process by which primitive, undifferentiated and tissuegenic cells are stimulated to develop into an ensemble of cells, not necessarily identical, that together carry out a specific function. This ensemble of cells is termed a tissue.

The term "growth-inductive matrix" as used herein refers to a matrix containing a substance or substances capable of recruiting or stimulating local tissuegenic cells so that the cells are induced (meaning to cause, bring about, bring about, or trigger) to differentiate and/or produce a tissue.

The terms "growth-inductive components" or "growth-inductive factors" or "tissuegenic factors" are used interchangeably to refer to the plethora of mediators associated with tissue development and repair.

The terms "growth medium", "growth media", "culture medium", and "culture media" refer to liquids or gels designed to support the growth of microorganisms or cells. There are different types of media for growing different types of cells, and the selection of appropriate media for certain cell types will be understood by those having ordinary skill in the art.

The term "implant" refers to any device or material inserted or placed, permanently or temporarily, into or onto a subject as well as those used for the administration or delivery of a therapeutic agent(s) or substance.

The term "improve" (or improving) as used herein refers to bring into a more desirable or excellent condition.

The terms "in the body", "void volume", "resection pocket", "excavation", "injection site", "deposition site" or "implant site" as used herein are meant to include all tissues of the body without limit, and may refer to spaces formed therein from injections, surgical incisions, tumor or tissue removal, tissue injuries, abscess formation, or any other similar cavity, space, or pocket formed thus by action of clinical assessment, treatment or physiologic response to disease or pathology as non-limiting examples thereof.

The term "injury," as used herein, refers to damage or harm to a structure or function of the body caused by an outside agent or force, which may be physical or chemical.

The terms "length", "width", and "thickness" refer to dimensions of an object measured along three axes which respectively extend in different, non-parallel directions (e.g., in the x-y-z system of three orthogonal axes). As used herein, the thickness of an object (e.g., a fiber or a particle) is equal to or less than the width of the object, which is, in turn, equal to or less than the length of the object.

The term "lyophilize", as used herein in all its grammatical forms, means tissue dehydrated for storage by conversion of the water content of frozen tissue to a gaseous state under vacuum that extracts moisture. Lyophilization is also known as freeze-drying and these terms are used interchangeable herein.

The term "matrix" refers to a surrounding substance within which something is contained or embedded.

The term "mill," and its various grammatical forms, as used herein refers to operations performed to grind, to cut, to shred, to chip, or to pulverize a substance, or equipment for performing such operations on a substance. The terms "freezer-mill", "freeze-mill", and their various grammatical forms, as used herein refer to milling a substance in a frozen state, or equipment for performing such operations.

The term "particle" as used herein refers to a chip, fragment, slice, fiber or other small constituent of a larger body (e.g., picoparticles, nanoparticles, microparticles, milliparticle, centiparticle, deciparticle; fractions thereof, or, in some instances, a larger segment or piece).

The term "piece" as used herein refers to a particle, section, strip, chip, fragment, slice, fiber or other part, derived from, cut off, or broken from a larger unit.

The term "recovered cartilage" as used herein means cartilage which is derived from a donor, whether the donor is the same as the patient, another human, a cadaver human, or another species (alive or not) and recovered cartilage may, for example, be any one or more of articular, costal, hyaline, elastic and fibrocartilage types of cartilage.

The term "reduced" or "to reduce", as used herein in all of its grammatical forms, refers to a diminishing, a decrease in, an attenuation or abatement of the degree, intensity, extent, size, amount, density or number of.

The term "regeneration" or "regenerate" as used herein refers to a process of recreation, reconstitution, renewal, revival, restoration, differentiation and growth to form a tissue with characteristics that conform with a natural counterpart of the tissue.

The term "rehydration" as used herein refers to the restoration of water or fluid content to a body, tissue, or substance that has had water or fluid removed via drying processes, including but not limited to dehydration, lyophilization, freeze-drying or any other drying process.

The term "relative" as used herein refers to something having, or standing in, some significant association to something else.

The term "repair" as used herein as a noun refers to any correction, reinforcement, reconditioning, remedy, making up for, making sound, renewal, mending, patching, or the like that restores function. When used as a verb, it means to correct, to reinforce, to recondition, to remedy, to make up for, to make sound, to renew, to mend, to patch or to otherwise restore function. According to some embodiments "repair" includes full repair and partial repair.

The term "resident," and its various grammatical forms, as used herein refers to being present habitually, existing in or intrinsic to or incorporated therein.

The term "rinse," and its various grammatical forms, as used herein refers to wash, to douse with a liquid or liquids or to flow a liquid or liquids over the material being rinsed.

The term "scaffold" as used herein refers to a structure capable of supporting a three-dimensional tissue formation. A three-dimensional scaffold is believed to be critical to replicate the in vivo milieu and to allow the cells to influence their own microenvironment. Scaffolds may serve to promote cell attachment and migration, to deliver and retain cells and biochemical factors, to enable diffusion of vital cell nutrients and expressed products, and to exert certain mechanical and biological influences to modify the behavior of the cell phase. A scaffold utilized for tissue reconstruction has several requisites. Such a scaffold should have a high porosity and an adequate pore size to facilitate cell seeding and diffusion of both cells and nutrients throughout the whole structure. Biodegradability of the scaffold is also an essential requisite. The scaffold should be absorbed by the surrounding tissues without the necessity of a surgical removal, such that the rate at which degradation occurs coincides as closely as possible with the rate of tissue formation. As cells are fabricating their own natural matrix structure around themselves, the scaffold provides structural integrity within the body and eventually degrades leaving the neotissue (newly formed tissue) to assume the mechanical load.

The term "serum" as used herein refers to the clear portion of any physiological liquid separated from its more solid elements. With regard to sera derived from blood, "serum" refers to the clear liquid that separates from blood when it is allowed to clot completely (e.g., blood plasma from which fibrinogen is removed during clotting.

The term "similar" is used interchangeably with the terms analogous, comparable, or resembling, meaning having traits or characteristics in common.

The term "size reduction", as used herein in all of its grammatical forms, refers to a process by which an object, such as a tissue, is divided or reduced in size. Such processes include, without limitation, cutting, slicing, chopping, grinding, milling, freezer-milling, blending, homogenizing, tearing, shredding, fracturing, breaking, crushing, and morselizing.

A "solution" generally is considered as a homogeneous mixture of two or more substances. It is frequently, though not necessarily, a liquid. In a solution, the molecules of the solute (or dissolved substance) are uniformly distributed among those of the solvent. The term "solvent" as used herein refers to a substance capable of dissolving another substance (termed a "solute") to form a uniformly dispersed mixture (solution).

The term "stain" as used herein refers to a composition of a dye(s) or pigment(s) used to make a structure, a material, a cell, a cell component, a membrane, a granule, a nucleus, a cell surface receptor, a peptide, a microorganism, a nucleic acid, a protein or a tissue differentiable.

The phrase "subject in need thereof" as used herein refers to a patient that (i) will be administered at least one graft, (ii) is receiving at least one graft; or (iii) has received at least one graft, unless the context and usage of the phrase indicates otherwise.

The term "substantially free" as used herein means a subject material or composition includes less than 5% of the component or substance of which it is being said to be substantially free, based on the total original native component or substance that was present. For example, cartilage fibers that are substantially free of chondrocytes or their components are cartilage fibers which include less than 5%, by weight, of chondrocytes and their components, based on the original total weight of the native chondrocytes and their components originally present in the cartilage fibers.

The term "substantially similar" as used herein means that a first value, aspect, trait, feature, number, or amount is of at least 70%, at least 75%, at least 80%, at least 85%, at least 90%, or at least 95% of a second value, aspect, trait, feature, number, or amount.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect also may include, directly or indirectly, the arrest reduction or elimination of the progression of a disease manifestation.

The term "tissuegenic" as used herein refers to a potential of a precursor cell to differentiate into a mature cell type and to regenerate a tissue. Exemplary tissuegenic cells include but are not limited to a stem cell, a progenitor cell, a precursor cell, a non-terminally differentiated cell, an immature cell anywhere along its maturation pathway up to the point of terminal differentiation, any cell type with differentiation potential or any combination thereof. The term "osteogenic" refers more specifically to cell differentiation and tissue regeneration with regard to bone. The term "adipogenic" refers more specifically to cell differentiation and tissue regeneration with regard to the adipose compartment.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The term "viable" as used herein refers to having the ability to grow, expand, or develop; capable of living.

The term "xenogenic graft", "xenogeneic graft" or "xenograft" as used herein refers to a tissue that is grafted into an individual of one species from an individual of a different species.

While the disclosed invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the described invention.

The invention claimed is:

1. A cartilage-derived implant for treating a cartilage defect of cartilage, said implant being shapeable and comprising:
   a plurality of milled lyophilized cartilage particles having a size not greater than 1 millimeter and a reduced water content of from 0.1 to 8.0%, by weight based on the weight of the plurality of lyophilized cartilage particles; and
   a plurality of cartilage fibers which are elongated curled pieces of cartilage tissue, each having three or more laterally oriented striations,
   wherein the striations of the cartilage fibers enable the cartilage fibers to entangle with one another to a greater degree than cartilage fibers without such striations and form the implant which retains its shape until reshaped and conforms to and completely fills the cartilage defect when implanted in the cartilage defect.

2. The cartilage-derived implant of claim 1, further comprising a carrier.

3. The cartilage-derived implant of claim 1, further comprising a biologically compatible material.

4. The cartilage-derived implant of claim 1, wherein at least a portion of the cartilage fibers have been lyophilized.

5. The cartilage-derived implant of claim 1, wherein at least a portion of the plurality of cartilage fibers have been cryopreserved.

6. The cartilage-derived implant of claim 1, wherein the plurality of cartilage fibers and the plurality of cartilage particles are present in said implant in a ratio of fibers/particles of from 65/35 to 95/5 (w/w).

7. The cartilage-derived implant of claim 1, wherein the implant is capable of completely filling the cartilage defect when subjected to further shaping during implantation in the cartilage defect.

8. The cartilage-derived implant of claim 1, wherein said implant comprises a paste, a putty, or a gel.

9. The cartilage-derived implant of claim 1, wherein the plurality of cartilage fibers has an average length of at least about 5 millimeters, and an average thickness of from about 0.5 millimeters to about 5 millimeters.

10. The cartilage-derived implant of claim 1, wherein when said implant is implanted in the cartilage defect of cartilage having a native surface, the cartilage fibers do not migrate out of the cartilage defect and the implant remains substantially flush with the native surface after implanting and hydration.

11. The cartilage-derived implant of claim 1, wherein the plurality of cartilage fibers were produced from cartilage which was recovered from one or more donors and contained a population of viable endogenous cells and at least a portion of the plurality of cartilage fibers contain at least a portion of the population of viable endogenous cells.

12. The cartilage-derived implant of claim 1, further comprising a plurality of cartilage fibers which do not have laterally oriented striations.

* * * * *